US009402735B2

(12) United States Patent
McDonough et al.

(10) Patent No.: US 9,402,735 B2
(45) Date of Patent: Aug. 2, 2016

(54) ZERO-PROFILE INTERBODY SPACER AND COUPLED PLATE ASSEMBLY

(71) Applicant: DePuy Synthes Products, Inc., Raynham, MA (US)

(72) Inventors: William P. McDonough, West Chester, PA (US); William L. Strausbaugh, West Chester, PA (US); Christopher Bonner, West Chester, PA (US); Thomas Pepe, West Chester, PA (US); Ralph Meili, Oberdorf (CH); Markus Hunziker, Oberdorf (CH); Michael Jeger, Oberdorf (CH); Thomas Kueenzi, Oberdorf (CH); David Koch, Bubendorf (CH); Rainer Ponzer, Oberdorf (CH); Joern Richter, Oberdorf (CH); Roger Berger, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 219 days.

(21) Appl. No.: 13/901,002

(22) Filed: May 23, 2013

(65) Prior Publication Data
US 2013/0268008 A1    Oct. 10, 2013

Related U.S. Application Data

(63) Continuation of application No. 12/614,082, filed on Nov. 6, 2009, now abandoned.

(60) Provisional application No. 61/112,441, filed on Nov. 7, 2008, provisional application No. 61/139,920, filed on Dec. 22, 2008.

(51) Int. Cl.
*A61B 17/88* (2006.01)
*A61F 2/46* (2006.01)
(Continued)

(52) U.S. Cl.
CPC .......... *A61F 2/4455* (2013.01); *A61B 17/1757* (2013.01); *A61B 17/8033* (2013.01);
(Continued)

(58) Field of Classification Search
CPC .......... A61F 2/4611; A61F 2002/4638; A61F 2002/4642
See application file for complete search history.

(56) References Cited

U.S. PATENT DOCUMENTS 424,836 A    4/1890  Thompson
1,105,105 A  7/1914  Sherman
(Continued)

FOREIGN PATENT DOCUMENTS

AU    2004/232317    11/2010
CA         2317791     8/1999
(Continued)

OTHER PUBLICATIONS

"Jury Trial Demanded", In The United States District Court For The District Of Delaware, Case No. 1:11-cv-00652-LPS, filed Jul. 22, 2011, 8 pages.
(Continued)

*Primary Examiner* — Kevin T Truong
*Assistant Examiner* — Tracy Kamikawa
(74) *Attorney, Agent, or Firm* — Baker & Hostetler LLP

(57) ABSTRACT

An implant for insertion into the disc space between vertebrae. The implant including a spacer portion, a plate portion coupled to the spacer portion, a plurality of bone fixation elements for engaging the vertebrae and a retention mechanism for preventing the bone fixation elements from postoperatively uncoupling from the implant.

19 Claims, 28 Drawing Sheets

(51) Int. Cl.
*A61F 2/44* (2006.01)
*A61B 17/80* (2006.01)
*A61B 17/17* (2006.01)
*A61B 17/86* (2006.01)
*A61F 2/30* (2006.01)

(52) U.S. Cl.
CPC ......... *A61B17/8042* (2013.01); *A61B 17/8052* (2013.01); *A61B 17/88* (2013.01); *A61F 2/4465* (2013.01); *A61F 2/4611* (2013.01); *A61B 17/1728* (2013.01); *A61B 17/8057* (2013.01); *A61B 17/86* (2013.01); *A61F 2/30965* (2013.01); *A61F 2002/305* (2013.01); *A61F 2002/30387* (2013.01); *A61F 2002/30505* (2013.01); *A61F 2002/30507* (2013.01); *A61F 2002/30517* (2013.01); *A61F 2002/30576* (2013.01); *A61F 2002/30604* (2013.01); *A61F 2002/30787* (2013.01); *A61F 2002/30794* (2013.01); *A61F 2002/30841* (2013.01); *A61F 2002/4475* (2013.01); *A61F 2220/0016* (2013.01); *A61F 2220/0025* (2013.01); *A61F 2230/0034* (2013.01); *A61F 2310/00017* (2013.01); *A61F 2310/00023* (2013.01); *A61F 2310/00029* (2013.01); *A61F 2310/00131* (2013.01); *A61F 2310/00407* (2013.01); *A61F 2310/00796* (2013.01)

(56) References Cited

U.S. PATENT DOCUMENTS

| | | |
|---|---|---|
| 1,200,797 A | 10/1916 | Barbe |
| 2,151,919 A | 3/1939 | Jacobson |
| 2,372,888 A | 4/1945 | Edward |
| 2,621,145 A | 12/1952 | Sano |
| 2,782,827 A | 2/1957 | Joseph |
| 2,906,311 A | 9/1959 | Boyd |
| 2,972,367 A | 2/1961 | Wootton |
| 3,062,253 A | 11/1962 | Melvin |
| 3,272,249 A | 9/1966 | Houston |
| 3,350,103 A | 10/1967 | Ahlstone |
| 3,426,364 A | 2/1969 | Lumb et al. |
| 3,561,075 A | 2/1971 | Selinko |
| 3,579,831 A | 5/1971 | Stevens et al. |
| 3,707,303 A | 12/1972 | Petri |
| 3,810,703 A | 5/1974 | Pasbrig |
| 3,867,728 A | 2/1975 | Stubstad et al. |
| 3,899,897 A | 8/1975 | Boerger et al. |
| 3,945,671 A | 3/1976 | Gerlach |
| 4,017,946 A | 4/1977 | Soja |
| 4,056,301 A | 11/1977 | Norden |
| 4,123,132 A | 10/1978 | Hardy |
| 4,135,506 A | 1/1979 | Ulrich |
| 4,278,120 A | 7/1981 | Hart et al. |
| 4,280,875 A | 7/1981 | Werres |
| 4,285,377 A | 8/1981 | Hart |
| 4,288,902 A | 9/1981 | Franz |
| 4,297,063 A | 10/1981 | Hart |
| 4,298,993 A | 11/1981 | Kovaleva et al. |
| 4,299,902 A | 11/1981 | Soma et al. |
| 4,349,921 A | 9/1982 | Kuntz |
| 4,388,921 A | 6/1983 | Sutter et al. |
| 4,394,370 A | 7/1983 | Jefferies |
| 4,450,591 A | 5/1984 | Rappaport |
| 4,484,570 A | 11/1984 | Sutter et al. |
| 4,488,543 A | 12/1984 | Tornier |
| 4,501,269 A | 2/1985 | Bagby |
| 4,503,848 A | 3/1985 | Casper et al. |
| 4,512,038 A | 4/1985 | Alexander et al. |
| 4,545,374 A | 10/1985 | Jacobson |
| 4,553,890 A | 11/1985 | Gulistan |
| 4,599,086 A | 7/1986 | Doty |
| 4,627,853 A | 12/1986 | Campbell et al. |
| 4,640,524 A | 2/1987 | Sedlmair |
| 4,648,768 A | 3/1987 | Hambric |
| 4,678,470 A | 7/1987 | Nashef et al. |
| 4,708,377 A | 11/1987 | Hunting |
| 4,711,760 A | 12/1987 | Blaushild |
| 4,714,469 A | 12/1987 | Kenna |
| 4,717,115 A | 1/1988 | Schmitz et al. |
| 4,743,256 A | 5/1988 | Brantigan |
| 4,781,721 A | 11/1988 | Grundei |
| 4,793,335 A | 12/1988 | Frey et al. |
| 4,804,290 A | 2/1989 | Balsells |
| 4,812,094 A | 3/1989 | Grube |
| 4,829,152 A | 5/1989 | Rostoker et al. |
| 4,834,757 A | 5/1989 | Brantigan |
| 4,858,603 A | 8/1989 | Clemow et al. |
| 4,872,452 A | 10/1989 | Alexson |
| 4,878,915 A | 11/1989 | Brantigan |
| 4,904,261 A | 2/1990 | Dove et al. |
| 4,917,704 A | 4/1990 | Frey et al. |
| 4,936,851 A | 6/1990 | Fox et al. |
| 4,950,296 A | 8/1990 | McIntyre |
| 4,955,908 A | 9/1990 | Frey et al. |
| 4,961,740 A | 10/1990 | Ray et al. |
| 4,976,576 A | 12/1990 | Mahaney |
| 4,978,350 A | 12/1990 | Wagenknecht |
| 4,994,084 A | 2/1991 | Brennan |
| 4,997,432 A | 3/1991 | Keller |
| 5,006,120 A | 4/1991 | Carter |
| 5,010,783 A | 4/1991 | Sparks et al. |
| 5,017,069 A | 5/1991 | Stencel |
| 5,020,949 A | 6/1991 | Davidson et al. |
| 5,026,373 A | 6/1991 | Ray et al. |
| 5,030,220 A | 7/1991 | Howland |
| 5,047,058 A | 9/1991 | Roberts et al. |
| 5,053,049 A | 10/1991 | Campbell |
| 5,062,850 A | 11/1991 | MacMillan et al. |
| 5,071,437 A | 12/1991 | Steffee |
| 5,084,051 A | 1/1992 | Tormala et al. |
| 5,085,660 A | 2/1992 | Lin |
| 5,096,150 A | 3/1992 | Westwood |
| 5,108,438 A | 4/1992 | Stone et al. |
| 5,112,354 A | 5/1992 | Sires |
| 5,116,374 A | 5/1992 | Stone |
| 5,118,235 A | 6/1992 | Dill |
| 5,139,424 A | 8/1992 | Yli-Urpo |
| 5,147,404 A | 9/1992 | Downey |
| 5,180,381 A | 1/1993 | Aust et al. |
| 5,192,327 A | 3/1993 | Brantigan |
| 5,201,736 A | 4/1993 | Strauss |
| 5,207,543 A | 5/1993 | Kirma |
| 5,211,664 A | 5/1993 | Tepic et al. |
| 5,235,034 A | 8/1993 | Bobsein et al. |
| 5,238,342 A | 8/1993 | Stencel |
| 5,258,031 A | 11/1993 | Salib et al. |
| 5,275,601 A | 1/1994 | Gogolewski et al. |
| 5,281,226 A | 1/1994 | Davydov et al. |
| 5,282,861 A | 2/1994 | Kaplan |
| 5,284,655 A | 2/1994 | Bogdansky et al. |
| 5,290,312 A | 3/1994 | Kojimoto et al. |
| 5,298,254 A | 3/1994 | Prewett et al. |
| 5,304,021 A | 4/1994 | Oliver et al. |
| 5,306,308 A | 4/1994 | Gross et al. |
| 5,306,309 A | 4/1994 | Wagner et al. |
| 5,314,476 A | 5/1994 | Prewett et al. |
| 5,314,477 A | 5/1994 | Marnay |
| 5,330,535 A | 7/1994 | Moser et al. |
| 5,348,788 A | 9/1994 | White |
| 5,368,593 A | 11/1994 | Stark |
| 5,380,323 A | 1/1995 | Howland |
| 5,385,583 A | 1/1995 | Cotrel |
| 5,397,364 A | 3/1995 | Kozak et al. |
| 5,405,391 A | 4/1995 | Hednerson et al. |
| 5,411,348 A | 5/1995 | Balsells |
| 5,423,817 A | 6/1995 | Lin |
| 5,425,772 A | 6/1995 | Brantigan |
| 5,431,658 A | 7/1995 | Moskovich |
| 5,439,684 A | 8/1995 | Prewett et al. |
| 5,443,514 A | 8/1995 | Steffee |
| 5,443,515 A | 8/1995 | Cohen et al. |

(56) References Cited

U.S. PATENT DOCUMENTS

| | | |
|---|---|---|
| 5,458,638 A | 10/1995 | Kuslich et al. |
| 5,458,641 A | 10/1995 | Ramirez Jimenez |
| 5,458,643 A | 10/1995 | Oka et al. |
| 5,478,342 A | 12/1995 | Kohrs |
| 5,484,437 A | 1/1996 | Michelson |
| 5,487,744 A | 1/1996 | Howland |
| 5,489,308 A | 2/1996 | Kuslich et al. |
| 5,507,818 A | 4/1996 | McLaughlin |
| 5,514,180 A | 5/1996 | Heggeness et al. |
| 5,520,690 A | 5/1996 | Errico et al. |
| 5,522,899 A | 6/1996 | Michelson |
| 5,531,746 A | 7/1996 | Errico et al. |
| 5,534,030 A | 7/1996 | Navarro et al. |
| 5,534,031 A | 7/1996 | Matsuzaki et al. |
| 5,534,032 A | 7/1996 | Hodorek |
| 5,545,842 A | 8/1996 | Balsells |
| 5,549,612 A | 8/1996 | Yapp et al. |
| 5,549,679 A | 8/1996 | Kuslich |
| 5,550,172 A | 8/1996 | Regula et al. |
| 5,554,191 A | 9/1996 | Lahille et al. |
| 5,556,430 A | 9/1996 | Gendler |
| 5,556,431 A | 9/1996 | Buttner-Janz |
| 5,569,308 A | 10/1996 | Sotosanti |
| 5,570,983 A | 11/1996 | Hollander |
| 5,571,190 A | 11/1996 | Ulrich et al. |
| 5,571,192 A | 11/1996 | Schonhoffer |
| 5,578,034 A | 11/1996 | Estes |
| 5,593,409 A | 1/1997 | Michelson |
| 5,597,278 A | 1/1997 | Peterkort |
| 5,601,553 A | 2/1997 | Trebing et al. |
| 5,601,554 A | 2/1997 | Howland et al. |
| 5,607,428 A | 3/1997 | Lin |
| 5,607,474 A | 3/1997 | Athanasiou et al. |
| 5,609,635 A | 3/1997 | Michelson |
| 5,609,636 A | 3/1997 | Kohrs et al. |
| 5,609,637 A | 3/1997 | Biedermann et al. |
| 5,616,144 A | 4/1997 | Yapp et al. |
| 5,620,448 A | 4/1997 | Puddu |
| 5,642,960 A | 7/1997 | Salice |
| 5,645,596 A | 7/1997 | Kim et al. |
| 5,645,606 A | 7/1997 | Oehy et al. |
| 5,653,708 A | 8/1997 | Howland |
| 5,669,909 A | 9/1997 | Zdeblick et al. |
| 5,674,296 A | 10/1997 | Bryan et al. |
| 5,676,666 A | 10/1997 | Oxland |
| 5,676,699 A | 10/1997 | Gogolewski et al. |
| 5,681,311 A | 10/1997 | Foley et al. |
| 5,683,216 A | 11/1997 | Erbes |
| 5,683,394 A | 11/1997 | Rinner |
| 5,683,463 A | 11/1997 | Godefroy et al. |
| 5,702,449 A | 12/1997 | McKay et al. |
| 5,702,451 A | 12/1997 | Biedermann et al. |
| 5,702,453 A | 12/1997 | Rabbe et al. |
| 5,702,455 A | 12/1997 | Saggar |
| 5,713,899 A | 2/1998 | Marnay et al. |
| 5,713,900 A | 2/1998 | Benzel et al. |
| 5,725,531 A | 3/1998 | Shapiro |
| 5,725,588 A | 3/1998 | Errico et al. |
| 5,728,159 A | 3/1998 | Stroever et al. |
| 5,735,853 A | 4/1998 | Olerud |
| 5,735,905 A | 4/1998 | Parr |
| 5,755,796 A | 5/1998 | Ibo et al. |
| 5,755,798 A | 5/1998 | Papavero et al. |
| 5,766,251 A | 6/1998 | Koshino |
| 5,766,252 A | 6/1998 | Henry et al. |
| 5,766,253 A | 6/1998 | Brosnahan, III |
| 5,772,661 A | 6/1998 | Michelson |
| 5,776,194 A | 7/1998 | Mikol et al. |
| 5,776,196 A | 7/1998 | Matsuzaki et al. |
| 5,776,197 A | 7/1998 | Rabbe et al. |
| 5,776,198 A | 7/1998 | Rabbe et al. |
| 5,776,199 A | 7/1998 | Michelson |
| 5,778,804 A | 7/1998 | Read |
| 5,782,915 A | 7/1998 | Stone |
| 5,782,919 A | 7/1998 | Zdeblick et al. |
| 5,785,710 A | 7/1998 | Michelson |
| 5,800,433 A | 9/1998 | Benzel et al. |
| 5,836,948 A | 11/1998 | Zucherman et al. |
| 5,860,973 A | 1/1999 | Michelson |
| 5,861,041 A | 1/1999 | Tienboon |
| 5,865,845 A | 2/1999 | Thalgott |
| 5,865,849 A | 2/1999 | Stone |
| 5,876,402 A | 3/1999 | Errico et al. |
| 5,876,452 A | 3/1999 | Athanasiou et al. |
| 5,879,389 A | 3/1999 | Koshino |
| 5,885,299 A | 3/1999 | Winslow et al. |
| 5,888,222 A | 3/1999 | Coates et al. |
| 5,888,223 A | 3/1999 | Bray, Jr. |
| 5,888,224 A | 3/1999 | Beckers et al. |
| 5,888,227 A | 3/1999 | Cottle |
| 5,895,426 A | 4/1999 | Scarborough et al. |
| 5,899,939 A | 5/1999 | Boyce et al. |
| 5,902,303 A | 5/1999 | Eckhof et al. |
| 5,902,338 A | 5/1999 | Stone |
| 5,904,683 A | 5/1999 | Pohndorf et al. |
| 5,904,719 A | 5/1999 | Errico et al. |
| 5,906,616 A | 5/1999 | Pavlov et al. |
| 5,910,315 A | 6/1999 | Stevenson et al. |
| 5,911,758 A | 6/1999 | Oehy et al. |
| 5,920,312 A | 7/1999 | Wagner et al. |
| 5,922,027 A | 7/1999 | Stone |
| 5,931,838 A | 8/1999 | Vito |
| 5,944,755 A | 8/1999 | Stone |
| 5,951,558 A | 9/1999 | Fiz |
| 5,954,722 A | 9/1999 | Bono |
| 5,958,314 A | 9/1999 | Draenet |
| 5,964,807 A | 10/1999 | Gan et al. |
| 5,968,098 A | 10/1999 | Winslow |
| 5,972,368 A | 10/1999 | McKay |
| 5,976,141 A | 11/1999 | Haag et al. |
| 5,976,187 A | 11/1999 | Richelsoph |
| 5,980,522 A | 11/1999 | Koros et al. |
| 5,981,828 A | 11/1999 | Nelson et al. |
| 5,984,967 A | 11/1999 | Zdeblick et al. |
| 5,989,289 A | 11/1999 | Coates et al. |
| 6,001,099 A | 12/1999 | Huebner |
| 6,008,433 A | 12/1999 | Stone |
| 6,013,853 A | 1/2000 | Athanasiou et al. |
| 6,017,345 A | 1/2000 | Richelsoph |
| 6,025,538 A | 2/2000 | Yaccarino, III |
| 6,033,405 A | 3/2000 | Winslow et al. |
| 6,033,438 A | 3/2000 | Bianchi et al. |
| 6,039,762 A | 3/2000 | McKay |
| 6,045,579 A | 4/2000 | Hochshuler et al. |
| 6,045,580 A | 4/2000 | Scarborough et al. |
| 6,056,749 A | 5/2000 | Kuslich |
| 6,066,175 A | 5/2000 | Henderson et al. |
| 6,080,158 A | 6/2000 | Lin |
| 6,080,193 A | 6/2000 | Hochshuler et al. |
| 6,086,593 A | 7/2000 | Bonutti |
| 6,086,614 A | 7/2000 | Mumme |
| 6,090,998 A | 7/2000 | Grooms et al. |
| 6,096,080 A | 8/2000 | Nicholson et al. |
| 6,096,081 A | 8/2000 | Grivas et al. |
| 6,099,531 A | 8/2000 | Bonutti |
| 6,110,482 A | 8/2000 | Khouri et al. |
| 6,113,637 A * | 9/2000 | Gill et al. .................. 623/17.15 |
| 6,113,638 A | 9/2000 | Williams et al. |
| 6,120,503 A | 9/2000 | Michelson |
| 6,123,731 A | 9/2000 | Boyce et al. |
| 6,129,763 A | 10/2000 | Chauvin et al. |
| 6,136,001 A | 10/2000 | Michelson |
| 6,139,550 A | 10/2000 | Michelson |
| 6,143,030 A | 11/2000 | Schroder |
| 6,143,033 A | 11/2000 | Paul et al. |
| 6,146,421 A | 11/2000 | Gordon et al. |
| 6,156,070 A | 12/2000 | Incavo et al. |
| 6,193,721 B1 | 2/2001 | Michelson |
| 6,193,756 B1 | 2/2001 | Studer et al. |
| 6,193,757 B1 | 2/2001 | Foley et al. |
| 6,200,347 B1 | 3/2001 | Anderson et al. |
| 6,206,922 B1 | 3/2001 | Zdeblick et al. |
| 6,224,602 B1 | 5/2001 | Hayes |
| 6,231,610 B1 | 5/2001 | Geisler |

(56) References Cited

U.S. PATENT DOCUMENTS

| | | | |
|---|---|---|---|
| 6,235,033 | B1 | 5/2001 | Brace et al. |
| 6,235,034 | B1 | 5/2001 | Bray |
| 6,235,059 | B1 | 5/2001 | Benezech et al. |
| 6,241,731 | B1 | 6/2001 | Fiz |
| 6,241,769 | B1 | 6/2001 | Nicholson et al. |
| 6,245,108 | B1 | 6/2001 | Biscup |
| 6,258,089 | B1 | 7/2001 | Campbell et al. |
| 6,258,125 | B1 | 7/2001 | Paul et al. |
| 6,261,291 | B1 | 7/2001 | Talaber et al. |
| 6,261,586 | B1 | 7/2001 | McKay |
| 6,264,695 | B1 | 7/2001 | Stoy |
| 6,270,528 | B1 | 8/2001 | McKay |
| 6,306,139 | B1 | 10/2001 | Fuentes |
| 6,322,562 | B1 | 11/2001 | Wolter |
| 6,331,179 | B1 | 12/2001 | Freid et al. |
| 6,342,074 | B1 | 1/2002 | Simpson |
| 6,364,880 | B1 | 4/2002 | Michelson |
| 6,371,986 | B1 | 4/2002 | Bagby |
| 6,371,988 | B1 | 4/2002 | Pafford et al. |
| 6,371,989 | B1 | 4/2002 | Chauvin et al. |
| 6,375,681 | B1 | 4/2002 | Truscott |
| 6,383,186 | B1 | 5/2002 | Michelson |
| 6,387,130 | B1 | 5/2002 | Stone et al. |
| 6,395,031 | B1 | 5/2002 | Foley et al. |
| 6,398,811 | B1 | 6/2002 | McKay |
| 6,413,259 | B1 | 7/2002 | Lyons et al. |
| 6,423,063 | B1 | 7/2002 | Bonutti |
| 6,432,106 | B1 | 8/2002 | Fraser |
| 6,443,987 | B1 | 9/2002 | Bryan |
| 6,447,512 | B1 | 9/2002 | Landry et al. |
| 6,447,546 | B1 | 9/2002 | Bramlet et al. |
| 6,454,771 | B1 | 9/2002 | Michelson |
| 6,458,158 | B1 | 10/2002 | Anderson et al. |
| 6,461,359 | B1 | 10/2002 | Tribus et al. |
| 6,468,311 | B2 | 10/2002 | Boyd et al. |
| 6,471,724 | B2 | 10/2002 | Zdeblick et al. |
| 6,482,233 | B1 | 11/2002 | Aebi et al. |
| 6,503,250 | B2 | 1/2003 | Paul |
| 6,511,509 | B1 | 1/2003 | Ford et al. |
| 6,524,312 | B2 | 2/2003 | Landry et al. |
| 6,558,387 | B2 | 5/2003 | Errico et al. |
| 6,558,423 | B1 | 5/2003 | Michelson |
| 6,558,424 | B2 | 5/2003 | Thalgott |
| 6,562,073 | B2 | 5/2003 | Foley |
| 6,569,201 | B2 | 5/2003 | Moumene et al. |
| 6,575,975 | B2 | 6/2003 | Brace et al. |
| 6,576,017 | B2 | 6/2003 | Foley et al. |
| 6,579,290 | B1 | 6/2003 | Hardcastle et al. |
| 6,592,624 | B1 | 7/2003 | Fraser et al. |
| 6,602,291 | B1 | 8/2003 | Ray et al. |
| 6,605,090 | B1 | 8/2003 | Trieu et al. |
| 6,616,671 | B2 | 9/2003 | Landry et al. |
| 6,620,163 | B1 | 9/2003 | Michelson |
| 6,623,486 | B1 | 9/2003 | Weaver et al. |
| 6,629,998 | B1 | 10/2003 | Lin |
| 6,638,310 | B2 | 10/2003 | Lin et al. |
| 6,645,212 | B2 | 11/2003 | Goldhahn et al. |
| 6,652,525 | B1 | 11/2003 | Assaker et al. |
| 6,656,181 | B2 | 12/2003 | Dixon et al. |
| 6,679,887 | B2 | 1/2004 | Nicholson et al. |
| 6,682,561 | B2 | 1/2004 | Songer et al. |
| 6,682,563 | B2 | 1/2004 | Scharf |
| 6,695,846 | B2 | 2/2004 | Richelsoph et al. |
| 6,695,851 | B2 | 2/2004 | Zdeblick et al. |
| 6,706,067 | B2 | 3/2004 | Shimp et al. |
| 6,709,456 | B2 | 3/2004 | Langberg et al. |
| 6,712,818 | B1 | 3/2004 | Michelson |
| 6,730,127 | B2 | 5/2004 | Michelson |
| 6,736,850 | B2 | 5/2004 | Davis |
| 6,761,739 | B2 | 7/2004 | Shepard |
| 6,770,096 | B2 | 8/2004 | Bolger et al. |
| 6,786,909 | B1 | 9/2004 | Dransfeld |
| 6,800,092 | B1 | 10/2004 | Williams et al. |
| 6,805,714 | B2 | 10/2004 | Sutcliffe |
| 6,808,537 | B2 | 10/2004 | Michelson |
| 6,824,564 | B2 | 11/2004 | Crozet |
| 6,833,006 | B2 | 12/2004 | Foley et al. |
| 6,837,905 | B1 | 1/2005 | Lieberman |
| 6,849,093 | B2 | 2/2005 | Michelson |
| 6,855,168 | B2 | 2/2005 | Crozet |
| 5,872,915 | A1 | 3/2005 | Koga et al. |
| 6,863,673 | B2 | 3/2005 | Gerbec et al. |
| 6,884,242 | B2 | 4/2005 | LeHuec et al. |
| 6,890,334 | B2 | 5/2005 | Brace et al. |
| 6,896,701 | B2 | 5/2005 | Boyd et al. |
| 6,899,735 | B2 | 5/2005 | Coates et al. |
| 6,902,578 | B1 | 6/2005 | Anderson et al. |
| 6,916,320 | B2 | 7/2005 | Michelson |
| 6,923,756 | B2 | 8/2005 | Sudakov et al. |
| 6,953,477 | B2 | 10/2005 | Berry |
| 6,962,606 | B2 | 11/2005 | Michelson |
| 6,964,664 | B2 | 11/2005 | Freid et al. |
| 6,964,687 | B1 | 11/2005 | Bernard et al. |
| 6,972,019 | B2 * | 12/2005 | Michelson .................. 606/86 A |
| 6,972,035 | B2 | 12/2005 | Michelson |
| 6,974,479 | B2 | 12/2005 | Trieu |
| 6,984,234 | B2 | 1/2006 | Bray |
| 7,001,385 | B2 | 2/2006 | Bonutti |
| 7,001,432 | B2 | 2/2006 | Keller et al. |
| 7,018,416 | B2 | 3/2006 | Hanson et al. |
| 7,033,394 | B2 | 4/2006 | Michelson |
| 7,041,135 | B2 * | 5/2006 | Michelson .................. 623/17.11 |
| 7,044,972 | B2 | 5/2006 | Mathys et al. |
| 7,048,765 | B1 | 5/2006 | Grooms et al. |
| 7,060,097 | B2 * | 6/2006 | Fraser ...................... A61F 2/442 623/17.11 |
| 7,066,961 | B2 * | 6/2006 | Michelson .................. 623/17.16 |
| 7,077,864 | B2 | 7/2006 | Byrd, III et al. |
| 7,112,222 | B2 | 9/2006 | Fraser et al. |
| 7,112,223 | B2 | 9/2006 | Davis |
| 7,135,024 | B2 | 11/2006 | Cook et al. |
| 7,135,043 | B2 | 11/2006 | Nakahara et al. |
| 7,137,984 | B2 | 11/2006 | Michelson |
| 7,147,665 | B1 | 12/2006 | Bryan et al. |
| 7,163,561 | B2 | 1/2007 | Michelson |
| 7,172,627 | B2 | 2/2007 | Fiere et al. |
| 7,172,672 | B2 | 2/2007 | Silverbrook |
| 7,226,452 | B2 * | 6/2007 | Zubok ...................... A61F 2/442 606/99 |
| 7,226,482 | B2 | 6/2007 | Messerli et al. |
| 7,232,464 | B2 | 6/2007 | Mathieu et al. |
| 7,238,203 | B2 | 7/2007 | Bagga et al. |
| 7,255,698 | B2 | 8/2007 | Michelson |
| 7,276,082 | B2 | 10/2007 | Zdeblick et al. |
| 7,320,708 | B1 | 1/2008 | Bernstein |
| 7,323,011 | B2 | 1/2008 | Shepard et al. |
| 7,442,209 | B2 | 10/2008 | Michelson |
| 7,491,237 | B2 | 2/2009 | Randall et al. |
| 7,534,265 | B1 | 5/2009 | Boyd et al. |
| 7,594,932 | B2 | 9/2009 | Aferzon et al. |
| 7,601,173 | B2 | 10/2009 | Messerli et al. |
| 7,608,107 | B2 | 10/2009 | Michelson |
| 7,618,456 | B2 | 11/2009 | Mathieu et al. |
| 7,621,960 | B2 | 11/2009 | Boyd et al. |
| 7,625,380 | B2 | 12/2009 | Drewry et al. |
| 7,637,951 | B2 | 12/2009 | Michelson |
| 7,655,042 | B2 | 2/2010 | Foley et al. |
| 7,704,279 | B2 | 4/2010 | Moskowitz et al. |
| 7,846,188 | B2 | 12/2010 | Moskowitz et al. |
| 7,846,207 | B2 | 12/2010 | Lechmann et al. |
| 7,862,616 | B2 | 1/2011 | Lechmann |
| 7,875,076 | B2 | 1/2011 | Mathieu et al. |
| 7,942,903 | B2 | 5/2011 | Moskowitz et al. |
| 7,993,403 | B2 | 8/2011 | Foley et al. |
| 8,062,303 | B2 | 11/2011 | Berry et al. |
| 8,128,700 | B2 | 3/2012 | Delurio et al. |
| 8,182,532 | B2 | 5/2012 | Anderson et al. |
| 8,211,148 | B2 | 7/2012 | Zhang et al. |
| 8,273,127 | B2 | 9/2012 | Jones et al. |
| 8,308,804 | B2 | 11/2012 | Kureger |
| 8,328,872 | B2 | 12/2012 | Duffield et al. |
| 8,343,222 | B2 | 1/2013 | Cope |
| 8,353,913 | B2 | 1/2013 | Moskowitz et al. |
| 8,382,768 | B2 | 2/2013 | Berry et al. |

(56) References Cited

U.S. PATENT DOCUMENTS

| | | |
|---|---|---|
| 8,425,607 B2 | 4/2013 | Waugh et al. |
| 8,444,696 B2 | 5/2013 | Michelson |
| 8,465,546 B2 | 6/2013 | Jodaitis et al. |
| 8,540,774 B2 | 9/2013 | Kueenzi et al. |
| 8,545,567 B1 | 10/2013 | Kreuger |
| 8,641,743 B2 | 2/2014 | Michelson |
| 8,641,768 B2 | 2/2014 | Duffield et al. |
| 8,764,831 B2 | 7/2014 | Lechmann et al. |
| 9,005,295 B2 | 4/2015 | Kueenzi et al. |
| 2001/0001129 A1 | 5/2001 | McKay et al. |
| 2001/0005796 A1 | 6/2001 | Zdeblick et al. |
| 2001/0010021 A1 | 7/2001 | Boyd |
| 2001/0016777 A1 | 8/2001 | Biscup |
| 2001/0020186 A1 | 9/2001 | Boyee et al. |
| 2001/0031254 A1 | 10/2001 | Bianchi et al. |
| 2001/0039456 A1 | 11/2001 | Boyer, II et al. |
| 2001/0041941 A1 | 11/2001 | Boyer, II et al. |
| 2002/0004683 A1 | 1/2002 | Michelson et al. |
| 2002/0010511 A1 | 1/2002 | Michelson |
| 2002/0016595 A1 | 2/2002 | Michelson |
| 2002/0022843 A1 | 2/2002 | Michelson |
| 2002/0029084 A1 | 3/2002 | Paul et al. |
| 2002/0065517 A1 | 5/2002 | Paul |
| 2002/0082597 A1 | 6/2002 | Fraser |
| 2002/0082603 A1 | 6/2002 | Dixon et al. |
| 2002/0091447 A1 | 7/2002 | Shimp et al. |
| 2002/0095155 A1 | 7/2002 | Michelson |
| 2002/0099376 A1 | 7/2002 | Michelson |
| 2002/0099378 A1 | 7/2002 | Michelson |
| 2002/0106393 A1 | 8/2002 | Bianchi et al. |
| 2002/0111680 A1 | 8/2002 | Michelson |
| 2002/0128717 A1 | 9/2002 | Alfaro et al. |
| 2002/0147450 A1 | 10/2002 | LeHuec et al. |
| 2002/0169508 A1 | 11/2002 | Songer et al. |
| 2002/0193880 A1 | 12/2002 | Fraser |
| 2003/0045939 A1 | 3/2003 | Casutt |
| 2003/0078668 A1 | 4/2003 | Michelson |
| 2003/0125739 A1 | 7/2003 | Bagga et al. |
| 2003/0135277 A1 | 7/2003 | Bryan et al. |
| 2003/0153975 A1 | 8/2003 | Byrd |
| 2003/0167092 A1 | 9/2003 | Foley |
| 2003/0195626 A1 | 10/2003 | Huppert |
| 2003/0195632 A1 | 10/2003 | Foley et al. |
| 2003/0199881 A1 | 10/2003 | Bonutti |
| 2003/0199983 A1 | 10/2003 | Michelson |
| 2004/0078078 A1 | 4/2004 | Shepard |
| 2004/0078081 A1 | 4/2004 | Ferree |
| 2004/0092929 A1 | 5/2004 | Zindrick |
| 2004/0093084 A1 | 5/2004 | Michelson |
| 2004/0102848 A1 | 5/2004 | Michelson |
| 2004/0126407 A1 | 7/2004 | Falahee |
| 2004/0133278 A1 | 7/2004 | Marino et al. |
| 2004/0143270 A1 | 7/2004 | Zucherman et al. |
| 2004/0176853 A1 | 9/2004 | Sennett et al. |
| 2004/0199254 A1 | 10/2004 | Louis et al. |
| 2004/0210219 A1 | 10/2004 | Bray |
| 2004/0210310 A1 | 10/2004 | Trieu |
| 2004/0210314 A1 | 10/2004 | Michelson |
| 2004/0249377 A1 | 12/2004 | Kaes et al. |
| 2004/0254644 A1 | 12/2004 | Taylor |
| 2005/0015149 A1 | 1/2005 | Michelson |
| 2005/0021143 A1 | 1/2005 | Keller |
| 2005/0033433 A1 | 2/2005 | Michelson |
| 2005/0049593 A1 | 3/2005 | Duong et al. |
| 2005/0049595 A1 | 3/2005 | Suh et al. |
| 2005/0065605 A1 | 3/2005 | Jackson |
| 2005/0065607 A1 | 3/2005 | Gross |
| 2005/0065608 A1 | 3/2005 | Michelson |
| 2005/0071008 A1 | 3/2005 | Kirschman |
| 2005/0085913 A1 | 4/2005 | Fraser et al. |
| 2005/0101960 A1 | 5/2005 | Fiere et al. |
| 2005/0149193 A1 | 7/2005 | Zucherman et al. |
| 2005/0154391 A1 | 7/2005 | Doherty et al. |
| 2005/0159813 A1 | 7/2005 | Molz |
| 2005/0159818 A1 | 7/2005 | Blain |
| 2005/0159819 A1 | 7/2005 | McCormick et al. |
| 2005/0171607 A1 | 8/2005 | Michelson |
| 2005/0177236 A1 | 8/2005 | Mathieu et al. |
| 2005/0240267 A1 | 10/2005 | Randall et al. |
| 2005/0240271 A1 | 10/2005 | Zubock et al. |
| 2005/0261767 A1 | 11/2005 | Anderson et al. |
| 2006/0020342 A1 | 1/2006 | Feree et al. |
| 2006/0030851 A1 | 2/2006 | Bray et al. |
| 2006/0079901 A1 | 4/2006 | Ryan et al. |
| 2006/0079961 A1 | 4/2006 | Michelson |
| 2006/0085071 A1 | 4/2006 | Lechmann et al. |
| 2006/0089717 A1 | 4/2006 | Krishna |
| 2006/0129240 A1 | 6/2006 | Lessar et al. |
| 2006/0136063 A1 | 6/2006 | Zeegers |
| 2006/0142765 A9 | 6/2006 | Dixon et al. |
| 2006/0195189 A1 | 8/2006 | Link et al. |
| 2006/0206208 A1 | 9/2006 | Michelson |
| 2006/0229725 A1 | 10/2006 | Lechmann et al. |
| 2007/0088441 A1 | 4/2007 | Duggal et al. |
| 2007/0093819 A1 | 4/2007 | Albert |
| 2007/0106384 A1 | 5/2007 | Bray et al. |
| 2007/0118125 A1 | 5/2007 | Orbay et al. |
| 2007/0123987 A1 | 5/2007 | Bernstein |
| 2007/0162130 A1 | 7/2007 | Rashbaum et al. |
| 2007/0168032 A1 | 7/2007 | Muhanna et al. |
| 2007/0219635 A1 | 9/2007 | Mathieu et al. |
| 2007/0225806 A1 | 9/2007 | Squires et al. |
| 2007/0225812 A1 | 9/2007 | Gill |
| 2007/0250167 A1 | 10/2007 | Bray et al. |
| 2007/0270961 A1 | 11/2007 | Ferguson |
| 2008/0033440 A1* | 2/2008 | Moskowitz et al. ............ 606/72 |
| 2008/0051890 A1 | 2/2008 | Waugh et al. |
| 2008/0082169 A1* | 4/2008 | Gittings ............... A61B 17/025 623/17.16 |
| 2008/0119933 A1 | 5/2008 | Aebi et al. |
| 2008/0133013 A1 | 6/2008 | Duggal et al. |
| 2008/0161925 A1 | 7/2008 | Brittan et al. |
| 2008/0177307 A1 | 7/2008 | Moskowitz et al. |
| 2008/0200984 A1 | 8/2008 | Jodaitis et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0269806 A1 | 10/2008 | Zhang et al. |
| 2008/0275455 A1 | 11/2008 | Berry et al. |
| 2008/0306596 A1 | 12/2008 | Jones et al. |
| 2009/0076608 A1 | 3/2009 | Gordon et al. |
| 2009/0105830 A1 | 4/2009 | Jones et al. |
| 2009/0192613 A1 | 7/2009 | Wing et al. |
| 2009/0210062 A1 | 8/2009 | Thalgott et al. |
| 2009/0210064 A1 | 8/2009 | Lechmann et al. |
| 2009/0234455 A1 | 9/2009 | Moskowitz et al. |
| 2009/0326580 A1 | 12/2009 | Anderson et al. |
| 2010/0016901 A1 | 1/2010 | Robinson |
| 2010/0125334 A1 | 5/2010 | Krueger |
| 2010/0145459 A1 | 6/2010 | McDonough et al. |
| 2010/0145460 A1 | 6/2010 | McDonough et al. |
| 2011/0118843 A1 | 5/2011 | Mathieu et al. |
| 2011/0295371 A1 | 12/2011 | Moskowitz et al. |
| 2012/0101581 A1 | 4/2012 | Mathieu et al. |
| 2012/0109309 A1 | 5/2012 | Mathieu et al. |
| 2012/0109310 A1 | 5/2012 | Mathieu et al. |
| 2012/0109311 A1 | 5/2012 | Mathieu et al. |
| 2012/0109312 A1 | 5/2012 | Mathieu et al. |
| 2012/0109313 A1 | 5/2012 | Mathieu et al. |
| 2012/0179259 A1 | 7/2012 | McDonough et al. |
| 2013/0073046 A1 | 3/2013 | Zaveloff et al. |
| 2013/0073047 A1 | 3/2013 | Laskowitz et al. |
| 2013/0166032 A1 | 6/2013 | McDonough et al. |
| 2013/0173013 A1 | 7/2013 | Anderson et al. |
| 2014/0025168 A1 | 1/2014 | Klimek et al. |
| 2014/0121777 A1 | 5/2014 | Rosen et al. |
| 2014/0180422 A1 | 6/2014 | Klimek et al. |

(56) References Cited

U.S. PATENT DOCUMENTS

| | | |
|---|---|---|
| 2014/0257487 A1 | 9/2014 | Lawson et al. |
| 2014/0336770 A1 | 11/2014 | Petersheim et al. |
| 2014/0371859 A1 | 12/2014 | Petersheim et al. |

FOREIGN PATENT DOCUMENTS

| | | |
|---|---|---|
| DE | 2821678 A | 11/1979 |
| DE | 3042003 | 7/1982 |
| DE | 3933459 | 4/1991 |
| DE | 4242889 | 6/1994 |
| DE | 4409392 | 9/1995 |
| DE | 4423257 | 1/1996 |
| DE | I9504867 CI | 2/1996 |
| DE | 29913200 | 9/1999 |
| DE | 202004020209 | 5/2006 |
| EP | 0179695 | 4/1986 |
| EP | 0425542 B1 | 5/1991 |
| EP | 0505634 | 9/1992 |
| EP | 0517030 | 9/1992 |
| EP | 0517030 A3 | 4/1993 |
| EP | 0577178 | 1/1994 |
| EP | 0639351 | 2/1995 |
| EP | 0639351 A3 | 3/1995 |
| EP | 0641547 B1 | 3/1995 |
| EP | 504346 B1 | 5/1995 |
| EP | 0517030 B1 | 9/1996 |
| EP | 0505634 B1 | 8/1997 |
| EP | 897697 A1 | 2/1999 |
| EP | 0906065 | 4/1999 |
| EP | 0966930 | 12/1999 |
| EP | 0968692 | 1/2000 |
| EP | 0974319 | 1/2000 |
| EP | 0974319 A2 | 1/2000 |
| EP | 1033941 | 9/2000 |
| EP | 1051133 | 11/2000 |
| EP | 1103236 | 5/2001 |
| EP | 1402836 | 3/2004 |
| EP | 1124512 | 9/2004 |
| EP | 1459711 | 7/2007 |
| EP | 1194087 | 8/2008 |
| FR | 2552659 | 4/1985 |
| FR | 2697996 | 5/1994 |
| FR | 2700947 | 8/1994 |
| FR | 2703580 A1 | 10/1994 |
| FR | 2727003 | 5/1996 |
| FR | 2747034 A1 | 10/1997 |
| FR | 2753368 | 3/1998 |
| GB | 157668 A | 1/1921 |
| GB | 265592 A | 8/1927 |
| GB | 2148122 | 5/1985 |
| GB | 2207607 | 2/1989 |
| GB | 2239482 A | 7/1991 |
| GB | 2266246 A | 10/1993 |
| JP | 3505416 | 11/1991 |
| JP | 9-280219 | 10/1997 |
| JP | 2006/513752 | 4/2006 |
| RU | 2229271 | 5/2004 |
| RU | 2244527 | 1/2005 |
| RU | 2307625 | 10/2007 |
| SU | 1465040 | 3/1989 |
| WO | WO 88/03417 | 5/1988 |
| WO | WO 88/10100 | 12/1988 |
| WO | WO 89/09035 | 10/1989 |
| WO | WO 90/00037 | 1/1990 |
| WO | WO 92/01428 | 2/1992 |
| WO | WO 92/06005 | 4/1992 |
| WO | WO 93/01771 | 2/1993 |
| WO | WO 95/08964 | 4/1995 |
| WO | WO 95/15133 | 6/1995 |
| WO | WO 95/20370 | 8/1995 |
| WO | WO 95/21053 | 8/1995 |
| WO | WO 95/26164 | 10/1995 |
| WO | WO 96/39988 | 12/1996 |
| WO | WO 96/40015 | 12/1996 |
| WO | WO 97/20526 | 6/1997 |
| WO | WO 97/23175 A | 7/1997 |
| WO | WO 97/25941 | 7/1997 |
| WO | WO 97/25945 | 7/1997 |
| WO | WO 97/37620 | 10/1997 |
| WO | WO 97/39693 | 10/1997 |
| WO | WO 98/17208 | 4/1998 |
| WO | WO 98/17209 | 4/1998 |
| WO | WO 98/55052 | 12/1998 |
| WO | WO 98/56319 | 12/1998 |
| WO | WO 98/56433 | 12/1998 |
| WO | WO 99/09896 | 3/1999 |
| WO | WO 99/09903 | 3/1999 |
| WO | WO 99/27864 | 6/1999 |
| WO | WO 99/29271 | 6/1999 |
| WO | WO 99/32055 | 7/1999 |
| WO | WO 99/38461 | 8/1999 |
| WO | WO 99/38463 | 8/1999 |
| WO | WO 99/56675 | 11/1999 |
| WO | WO 99/63914 | 12/1999 |
| WO | WO 00/07527 | 2/2000 |
| WO | WO 00/07528 | 2/2000 |
| WO | WO 00/25706 | 5/2000 |
| WO | WO 00/30568 | 6/2000 |
| WO | WO 00/40177 | 7/2000 |
| WO | WO 00/41654 | 7/2000 |
| WO | WO 00/59412 | 10/2000 |
| WO | WO 00/66044 | 11/2000 |
| WO | WO 00/66045 | 11/2000 |
| WO | WO 00/74607 | 12/2000 |
| WO | WO 01/08611 | 2/2001 |
| WO | WO 01/56497 | 8/2001 |
| WO | WO 01/62190 | 8/2001 |
| WO | WO 01/80785 | 11/2001 |
| WO | WO 01/56497 A3 | 12/2001 |
| WO | WO 01/93742 | 12/2001 |
| WO | WO 01/95837 | 12/2001 |
| WO | WO 01/95837 A1 | 12/2001 |
| WO | WO 01/56497 B1 | 3/2002 |
| WO | WO 01/93742 A3 | 9/2002 |
| WO | WO 2004/069106 | 8/2004 |
| WO | WO 2005/007040 A | 1/2005 |
| WO | WO 2005/020861 | 3/2005 |
| WO | WO 2006/138500 | 12/2006 |
| WO | WO 2007/098288 | 8/2007 |
| WO | WO 2008/014258 | 1/2008 |
| WO | WO 2008/082473 | 7/2008 |
| WO | WO 2008/124355 | 10/2008 |
| WO | WO 2008/154326 | 12/2008 |
| WO | WO 2009/064644 | 5/2009 |
| WO | WO 2010/054181 | 5/2010 |
| WO | WO 2010/054208 | 5/2010 |
| WO | WO 2012/088238 | 6/2012 |

OTHER PUBLICATIONS

Chadwick et al., "Radiolucent Structural Materials for Medical Application", www.mddionline.com/print/238, Jun. 2001, accessed Jul. 31, 2012, 9 pages.

Japanese Patent Application No. 2011-534926: Office Action dated Oct. 30, 2013, 7 pages.

Japanese Patent Application No. 2011-534928: Office Action dated Sep. 30, 2013, 11 pages.

Russian Patent Application No. 2011-1122797: Decision to Grant dated Oct. 9, 2013, 20 pages.

U.S. Appl. No. 60/988,661, filed Nov. 16, 2007, Kueenzi et al.

U.S. Appl. No. 61/535,726, filed Sep. 16, 2011, Zaveloff.

Appendix 1 to Joint Claim Construction Brief; Synthes' Exhibits A-9, In the United States District Court for the District of Delaware Civil Action No. 1:11-cv-00652-LPS, Jun. 8, 2012, 192 pages.

Appendix 2 to Joint Claim Construction Brief; Globus' Exhibits A-F, In the United States District Court for the District of Delaware Civil Action No. 1:11-cv-00652-LPS, Jun. 8, 2012, 146 pages.

Appendix 3 to Joint Claim Construction Brief; Exhibits A-C, In the United States District Court for the District of Delaware Civil Action No. 1:11-cv-00652-LPS, Jun. 8, 2012, 38 pages.

Expert Report of Dr. Domagoj Carie Regarding the Invalidity of U.S. Pat. Nos. 7,846,207, 7,862,616 and 7,875,076, In the United States

(56) References Cited

OTHER PUBLICATIONS

District Court for the District of Delaware, Civil Action No. 1:11-cv-00652-LPS, Nov. 5, 2012, 149 pages.
Expert Report of John F. Hall, M.D., United States District Court for the District of Delaware, Civil Action No. 1:11-cv-00652-LPS, Dec. 14, 2012, 27 pages.
Expert Report of Paul Ducheyne, Ph.D. Concerning Patent Validity, United States District Court District of Delaware, Civil Action No. 1:11-cv-00652-LPS, Dec. 13, 2012, 155 pages.
Expert Report of Richard J. Gering, Ph.D., CLP In the United States District Court for the District of Delaware, Civil Action No. 1:11-cv-00652-LPS, Dec. 14, 2012, 39 pages.
International Patent Application No. PCT/CH2003/00089, International Search Report dated Dec. 2, 2003, 3 pgs.
International Search Report, completed Aug. 16, 2007 for International Application No. PCT/US2007/005098, filed Feb. 27, 2007.
Joint Claim Construction Brief, In the United States District Court for the District of Delaware, Civil Action No. 1:11-cv-00652-LPS, Jun. 14, 2012, 97 pages.
Jonbergen et al., "Anterior CervicalInterbody fusion with a titanium box cage: Early radiological assessment of fusion and subsidence", The Spine Journal 5, Jul. 2005, 645-649.
Jury Verdict Form, United States District Court District of Delaware, Civil Action No. 1:11-cv-00652-LPS, Jun. 14, 2013, 20 pages.
Marcolongo et al., "Trends in Materials for Spine Surgery", Biomaterials and Clinical Use, 6, 2011, 21 pages.
Memorandum Opinion, United States District Court District of Delaware, Civil Action No. 1:11-cv-00652-LPS, May 7, 2013, 33 pages.
Order, United States District Court District of Delaware, Civil Action No. 1:11-cv-00652-LPS, May 15, 2013, 4 pages.
Order, United States District Court District of Delaware, Civil Action No. 1:11-cv-00652-LPS, May 7, 2013, 7 pages.
Parlov et al., "Anterior Lumbar Interbody Fusion with Threaded Fusion Cages and Autologous Grafts", Eur. Spine J., 2000, 9, 224-229.
Plaintiffs' Responses and Objections to Defendant Globus Medical, Inc.'s First Set of Interrogatories (Nos. 1-11), United States District Court for the District of Delaware, Civil Action No. 1:11-cv-00652-LPS, Nov. 14, 2011, 18 pages.
Plaintiffs' Supplemental Responses and Objections to Defendant Globus Medical Inc.'s Interrogatories Nos. 6-10 and Second Supplemental Responses and Objections to Interrogatory No. 5, United States District Court for the District of Delaware, Civil Action No. 11-cv-652-LPS, Sep. 1, 2012, 12 pages.
Redacted version of "Defendant Globus Medical, Inc.'s Answering Brief in Opposition to Plaintiff's Motion for Summary Judgment of No Anticipation by the Kozak and Michelson References", Mar. 12, 2013, 233 pages.
Redacted version of "Opening Brief in Support of Plaintiffs' Motion for Summary Judgment of No Anticipation by the Kozak and Michelson References", United States District Court District of Delaware, Civil Action No. 1:11-cv-00652-LPS, Feb. 13, 2013, 66 pages.
Redacted version of "Plaintiff's Reply Brief in Support of Plaintiff's Motion for Summary Judgment of No Anticipation by the Kozak and Michelson References", Mar. 21, 2013, 11 pages.
Reply Report of Dr. Domagoj Carie Regarding the Invalidity of U.S. Pat. Nos. 7,846,207, 7,862,616 and 7,875,076, In the United States District Court for the District of Delaware, Civil Action No. 1:11-cv-00652-LPS, Jan. 4, 2013, 81 pages.
Schleicher et al., "Biomechanical Comparison of Two Different Concepts for Stand-alone anterior lumbar interbody fusion", Eur. Spine J., Sep. 2008, 17, 1757-1765.
Scholz et al., "A New Stand-Alone Cervical Anterior Interbody Fusion Device", Spine, Jan. 2009, 34(2), 6 pages.
Second Expert Report of Wilson C. Hayes, Ph.D., United States District Court for the District of Delaware, Civil Action No. 1:11-cv-00652-LPS, Dec. 14, 2012, 22 pages.
Spruit et al., "The in Vitro Stabilizing Effect of Polyether-etherketone Cages Versus a Titanium Cage of similar design for anterior lumbar interbody fusion", Eur. Spine J., Aug. 2005, 14 752-758.
Trial Transcript, United States District Court District of Delaware, Civil Action No. 1:11-cv-00652-LPS, Jun. 10, 2013, 114 pages.
Trial Transcript, United States District Court District of Delaware, Civil Action No. 1:11-cv-00652-LPS, Jun. 11, 2013, 98 pages.
Trial Transcript, United States District Court District of Delaware, Civil Action No. 1:11-cv-00652-LPS, Jun. 12, 2013, 75 pages.
Trial Transcript, United States District Court District of Delaware, Civil Action No. 1:11-cv-00652-LPS, Jun. 13, 2013, 94 pages.
Trial Transcript, United States District Court District of Delaware, Civil Action No. 1:11-cv-00652-LPS, Jun. 14, 2013, 26 pages.
Trial Transcript, United States District Court District of Delaware, Civil Action No. 1:11-cv-00652-LPS, Jun. 3, 2013, 98 pages.
Trial Transcript, United States District Court District of Delaware, Civil Action No. 1:11-cv-00652-LPS, Jun. 4, 2013, 110 pages.
Trial Transcript, United States District Court District of Delaware, Civil Action No. 1:11-cv-00652-LPS, Jun. 5, 2013, 99 pages.
Trial Transcript, United States District Court District of Delaware, Civil Action No. 1:11-cv-00652-LPS, Jun. 6, 2013, 80 pages.
Trial Transcript, United States District Court District of Delaware, Civil Action No. 1:11-cv-00652-LPS, Jun. 7, 2013, 97 pages.
U.S. Appl. No. 11/199,599: Amendment/Request for Reconsideration after Non-Final Rejection, dated Sep. 29, 2009, 30 pages.
U.S. Appl. No. 11/199,599: Appeal Brief, dated Apr. 15, 2010, 51 pages.
U.S. Appl. No. 11/199,599: Final Rejection, dated Dec. 24, 2009, 21 pages.
U.S. Appl. No. 11/199,599: Interview Summary included Draft Amendments, dated Sep. 24, 2009, 16 pages.
U.S. Appl. No. 11/199,599: Non-Final Rejection, dated Apr. 1, 2009, 20 pages.
U.S. Appl. No. 11/199,599: Preliminary Amendment, dated Jan. 9, 2008, 11 pages.
Synthes Spine, "SynFix-LR System. Instruments and Implants for Stand-Alone Anterior Lumbar Interbody Fusion (ALIF)", Technique Guide dated 2008, pp. 2-40, Published by Synthes Spine (USA).
Synthes Spine, "Zero-P Instruments and Implants. Zero-Profile Anterior Cervical Interbody Fusion (ACIF) device", Technique Guide dated 2008, pp. 2-32, Published by Synthes Spine (USA).
Bray, "InterPlate Spine Fusion Device: Subsidence Control Without Stress Shielding", Orthopaedic Product News, Sep./Oct. 2006, pp. 22-25.
International Search Report, Mailed Mar. 20, 2009, for PCT International Application No. PCT/US80/82473, filed Nov. 5, 2008.
Written Opinion, Mailed Mar. 20, 2009, for PCT International Application No. PCT/US08/82473, filed Nov. 5, 2008.
Synthes Spine, "CorticoCancellous ACF Spacer. An allograft space or anterior fusion of the cervical spine," brochure, Musculoskeletal Transplant Foundationm, 2003, 6 pages.
International Patent Application PCT/US2011/066421, International Search Report dated Jun. 14, 2012, 31 pages.
U.S. Appl. No. 60/068,205, filed Dec. 19, 1997, Urbahns.
U.S. Appl. No. 60/071,527, filed Jan. 15, 1998, Urbahns.
Synthes History and Evolution of LBIF Brochure; Nov. 2015, 30 pages.
Synthes Spine Cervical Stand-Alone Devices Presentation Brochure; 2010, 40 pages.
DePuy Motech Surgical Titanium Mesh Brochure; 1998, 13 pages.
AcroMed Carbon Fiber Interbody Fusion Devices; Jan. 1998, 8 pages.
Carbon Fiber Composite Ramps for Lumbar Interbody Fusion; Apr. 1997, 2 pages.
Al-Sanabani, Application of Calcium Phosphate Materials in Dentistry, vol. 2013, Int. J. Biomaterials, 1-12, 2013.
Bailey, Stabilzation of the Cervical Spine by Anterior Fusion, 42-A(4), J. Bone Joint Surg., 565-594, Jun. 1960.
Banward, Iliac Crest Bone Graft Harvest Donor Site Morbidity, 20 (9) Spine 1055-1060, May 1995.
Benezech, L'arthrodese Cervicale Par Voie Anterieure a L'Aide de Plaque-Cage P.C.B., 9(1) Rachis 1, 47, 1997 (w/Translation).
Brantigan I/F Cage for PLIF Surgical Technique Guide; Apr. 1991, 22 pages.
Brantigan, A Carbon Fiber Implant to Aid Interbody Lumbar Fusion, 16(6S) Spine S277-S282, Jul. 1991.

(56) References Cited

OTHER PUBLICATIONS

Brantigan, Compression Strength of Donor Bone for Posterior Lumbar Interbody Fusion, 18(9) Spine 1213-1221, 1993.
Brantigan, Interbody Lumbar Fusion Using a Carbon Fiber Cage Implant Versus Allograft Bone, 19(13) Spine 1436-1444, 1994.
Brantigan, Intervertebral Fusion, Chapter 27, Posterior Lumbar Interbody Fusion Using the Lumbar Interbody Fusion Cage, 437-466, 2006.
Brantigan, Pseudarthrosis Rate After Allograft Posterior Lumbar Interbody Fusion with Pedicle Screw and Plate Fixation, 19(11) Spine 1271-1280, Jun. 1994.
Cloward, Gas-Sterilized Cadaver Bone Grafts for Spinal Fusion Operations, 5(1) Spine 4-10 Jan./Feb. 1980.
Cloward, The Anterior Approach for Removal of Ruptured Cervical Disks, vol. 15, J. Neuro. 602-617, 1958.
Delecrin, Morbidite du Prelevement de Greffons osseuz au Niveau des Cretes Iliaques dans la Chirurgie Du Rachis; Justification du recours aux substituts osseuz, 13(3) Rachis 167-174, 2001 (w/Translation).
Dereymaeker, Nouvelle Cure neuro-Chirurgicale de discopathies Cervicales, 2 Neurochirurgie 226-234; 1956 (w/Translation).
Dickman, Internal Fixation and Fusion of the Lumbar Spine Using Threaded Interbody Cages, 13(3) Barrow Quarterly (1997); http://www.thebarrow.org/Education_And_Resources/Barrow_Quarterly/204837.
Enker, Interbody Fusion and Instrumentation, No. 300 Clin. Orth. Rel. Res. 90-101, Mar. 1994.
Fassio, Use of Cervical Plate-Cage PCB and Results for Anterior Fusion in Cervical Disk Syndrome, 15(6) Rachis 355-361, Dec. 2003 Translation.
Fowler, Complications Associated with Harvesting Autogenous Iliac Bone Graft, 24(12) Am. J. Ortho. 895-904, Dec. 1995.
Fuentes, Les Complications de la Chirurgie Par Voie Anterieure du Rachis Cervical, 8(1) Rachis 3-14, 1996 (w/Translation).
Germay, Resultats Cliniques de Ceramiques D'hydroxyapatite dans les arthrodeses Inter-somatiques du Rachis Cervical Par Voie Anterieure. Etude Retrospective a Propose de 67 cas. 13(3), Rachis 189-195, 2001 (w/Translation).
Graham, Lateral Extracavitary Approach to the Thoracic and Thoracolumbar Spine, 20(7) Orthopedics, 605-610, Jul. 1997.
Gunatillake, Biodegradable Synthetic Polymers for Tissue Engineering, vol. 5, Eur. Cells Materials, 1-16, 2003.
Huttner, Spinal Stenosis & Posterior Lumbar Interbody Fusion, No. 193, Clinical Ortho Rel. Res. 103-114, Mar. 1985.
Jost, Compressive Strength of Interbody Cages in the Lumbar Spine: the Effect of Cage Shape, Posterior Instrumentation and Bone Density, 7 Eur. Spine J. 132-141, 1998.
Kastner, Advanced X-Ray Tomographic Methods for Quantitative Charecterisation of Carbon Fibre Reinforced Polymers, 4th Annual Intern. Symposium on NDT in Aerospace, 2012, 9 pages.
Khan, Chapter 2—Implantable Medical Devices, Focal Controlled Drug Delivery, Advances in Delivery Science and Technology, A.J. Domb and W. Khan (eds.) 2014.
Kozak, Anterior Lumbar Fusion Options, No. 300, Clin. Orth. Rel. Res., 45-51, 1994.
Kroppenstedt, Radiological Comparison of Instrumented Posterior Lumbar Interbody Fusion with One or Two Closed-Box Plasmapore Coated Titanium Cages, 33(19) Spine, 2083-2088, Sep. 2008.
Lund, Interbody Cage Stabilisation in the Lumbar Spine, 80-B(2) J Bone Joint Surg., 351-359, Mar. 1998.
Lyu, Degradability of Polymers for Implantable Biomedical Devices, 10, Int. J. Mol. Sci., 4033-4065, 2009.
Malca, Cervical Interbody Xenograft with Plate Fixation, 21(6) Spine, 685-690, Mar. 1996.
McAfee, Minimally Invasive Anterior Retroperitoneal Approach to the Lumbar Spine, 21(13) Spine, 1476-1484, 1998.
Nasca, Newer Lumbar Interbody Fusion Techniques, 22(2) J. Surg. Ortho. Advances, 113-117, 2013.
PCB Evolution Surgical Technique Guide 2010.
Polysciences Inc. Info Sheet 2012.
Porex Website, http://www.porex.com/technologies/materials/porous-plastics, Porous Plastic Materials, accessed Aug. 21, 2015, 2 pages.
Samandouras, A New Anterior Cervical Instrumentation System Combining an Intradiscal Cage with an Integrated Plate, 26(10) Spine, 1188-1192, 2001.
Sonntag, Controversy in Spine Care, Is Fusion Necessary After Anterior Cervical Discectomy 21(9) Spine, 1111-1113, May 1996.
Tamariz, Biodegradation of Medical Purpose Polymeric Materials and Their Impact on Biocompatibility, Chapter 1, Intech-bio degradation Life of Science, 2013; 28 pages.
Tan, A Modified Technique of Anterior Lumbar Fusion with Femoral Cortical Allograft, 5(3) J. Ortho. Surg. Tech., 83-93, 1990.
Verbiest H., La Chirurgie Anterieure et Laterale du Rachis Cervical,16(S2) Neurochirurgie 1-212; 1970 (w/Translation).
Wang, Increased Fusion Rates with Cervical Plating for Two-Level Anterior Cervical Discectomy and Fusion, 25(1) Spine 41-45, Jan. 2000.
Watters, Anterior Cervical Discectomy with and without Fusion, 19(20) Spine 2343-2347 Oct. 1994.
Weiner, Spinde Update Lumbar Interbody Cages, 23(5) Spine, 634-640, Mar. 1998.
White, Relief of Pain by Anterior Cervical-Spine Fusion for Spondylosis, 55-A(3) J. Bone Joint Surg. 525-534, Apr. 1973.
Whitesides, Lateral Approach to the Upper Cervical Spine for Anterior Fusion, vol. 59, South Med J, 879-883, Aug. 1966.
Wilson, Anterior Cervical Discectomy without Bone Graft, 47(4) J. Neurosurg. 551-555, Oct. 1977.
Younger, Morbidity at Bone Graft Donor Sites, 3(3) J. Orth. Trauma, 192-195, 1989.
Dabrowski, Highly Porous Titanium Scaffolds for Orthopaedic Applications, J. Biomed Mater. Res. B. Appl. Biomat. Oct;95(1):53-61, 2010.
Takahama, A New Improved Biodegradable Tracheal Prosthesis Using Hydroxy Apatite and Carbon Fiber 35(3) ASAIO Trans, 291-293, Jul.-Sep. 1989.
Wang, Determination of Cortical Bone Porosity and Pore Size Distribution using a Low Field Pulsed NMR Approach, J. Orthop Res., Mar; 21(2):312-9 Mar. 2003.

* cited by examiner

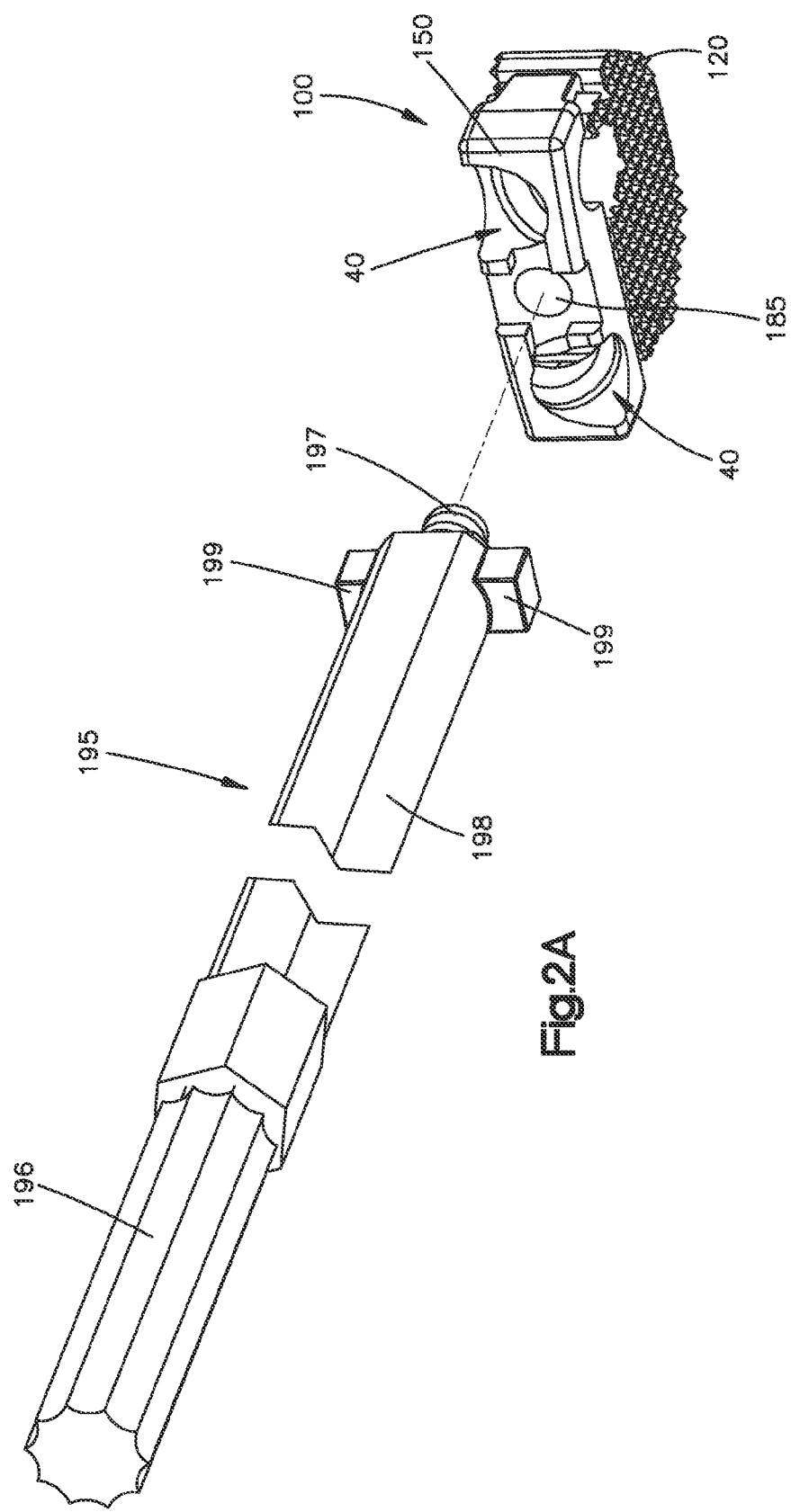

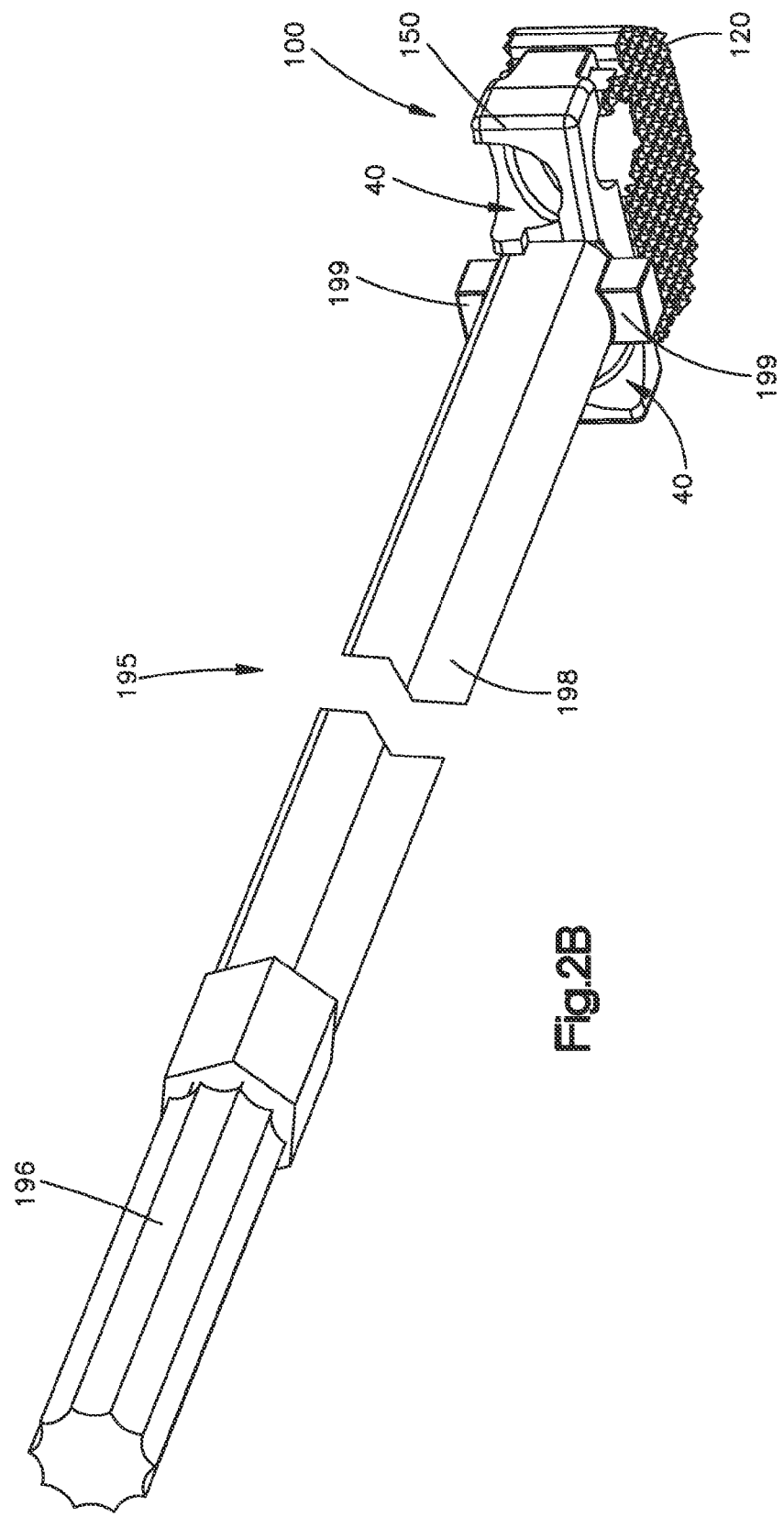

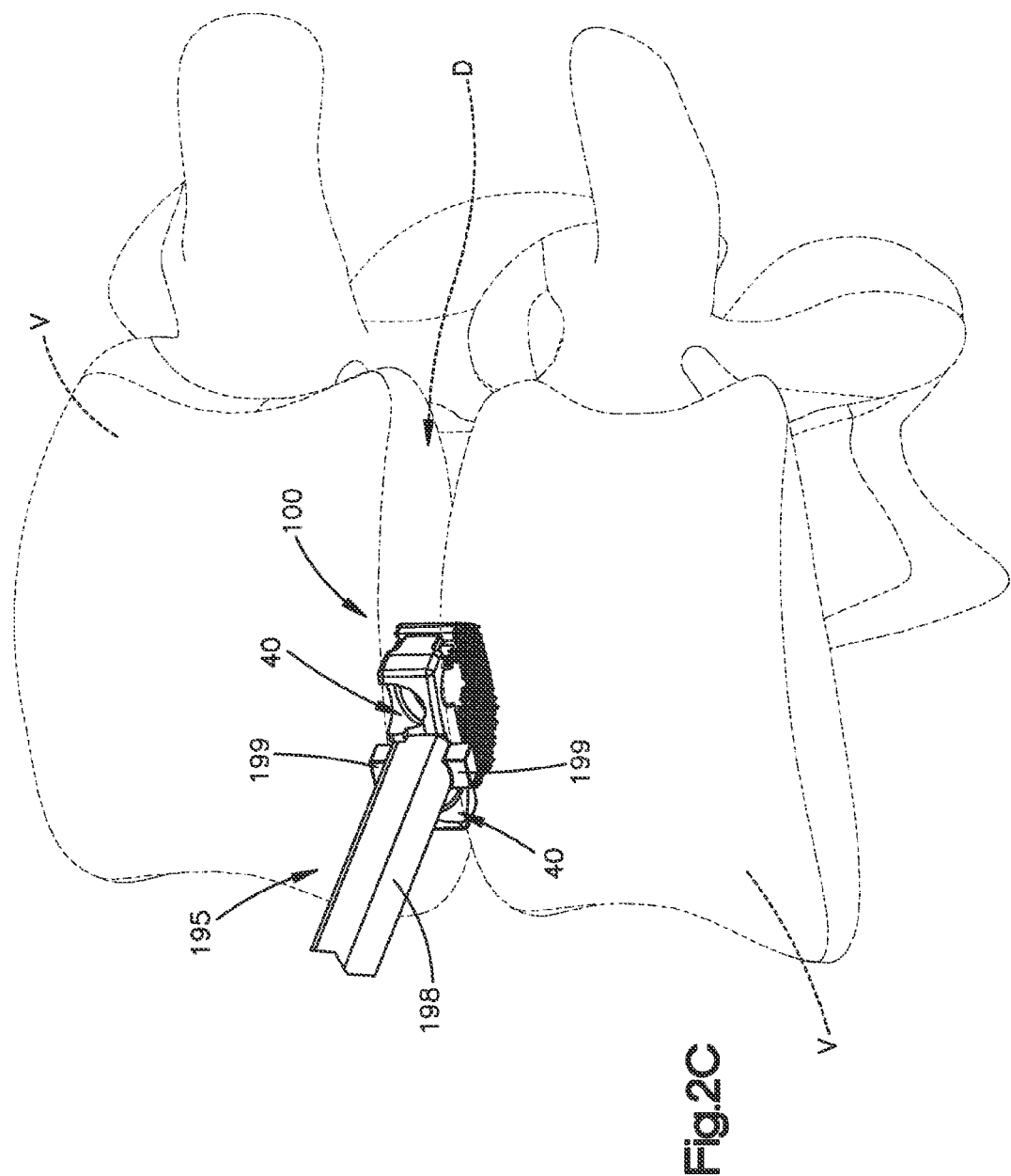

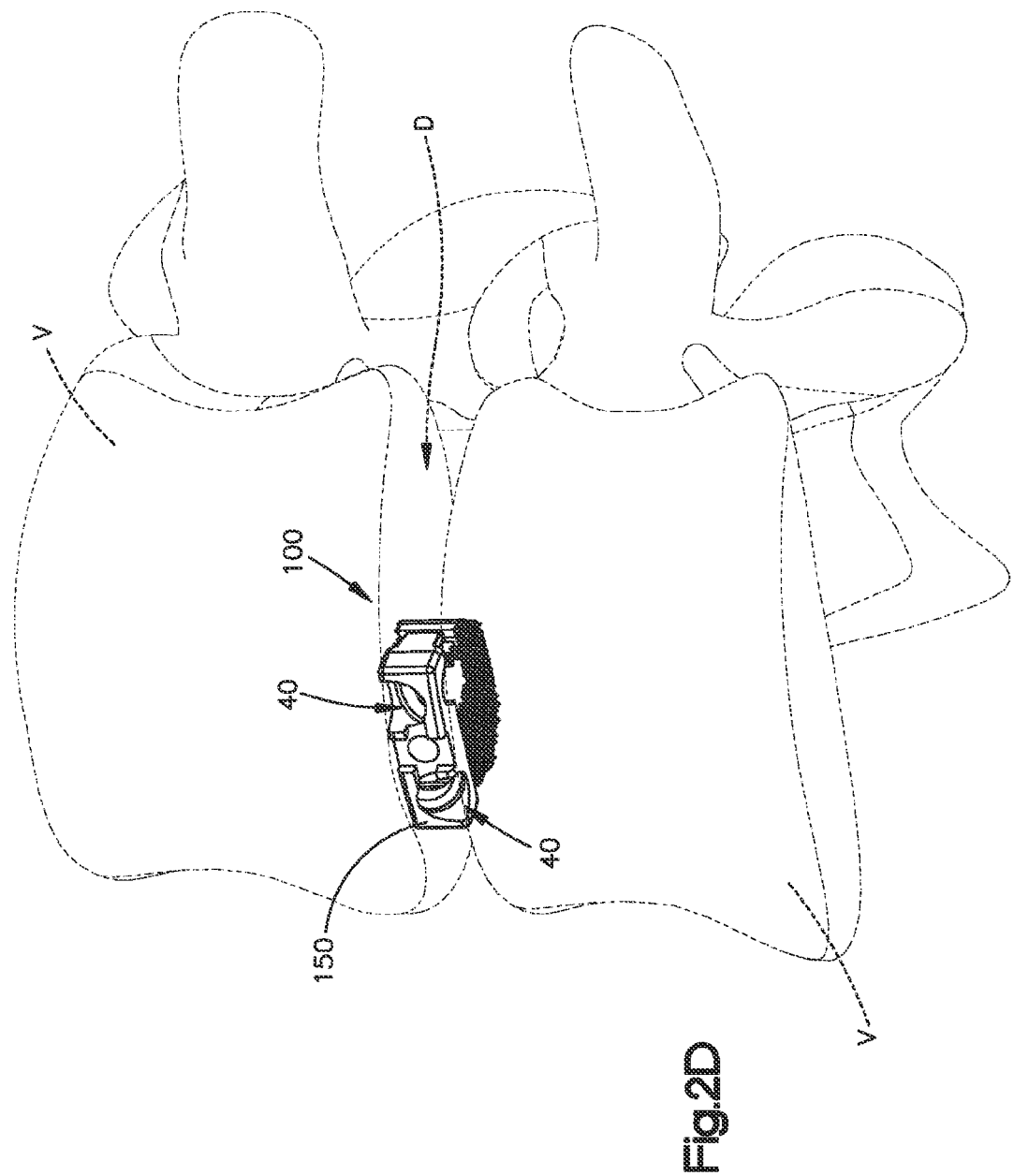

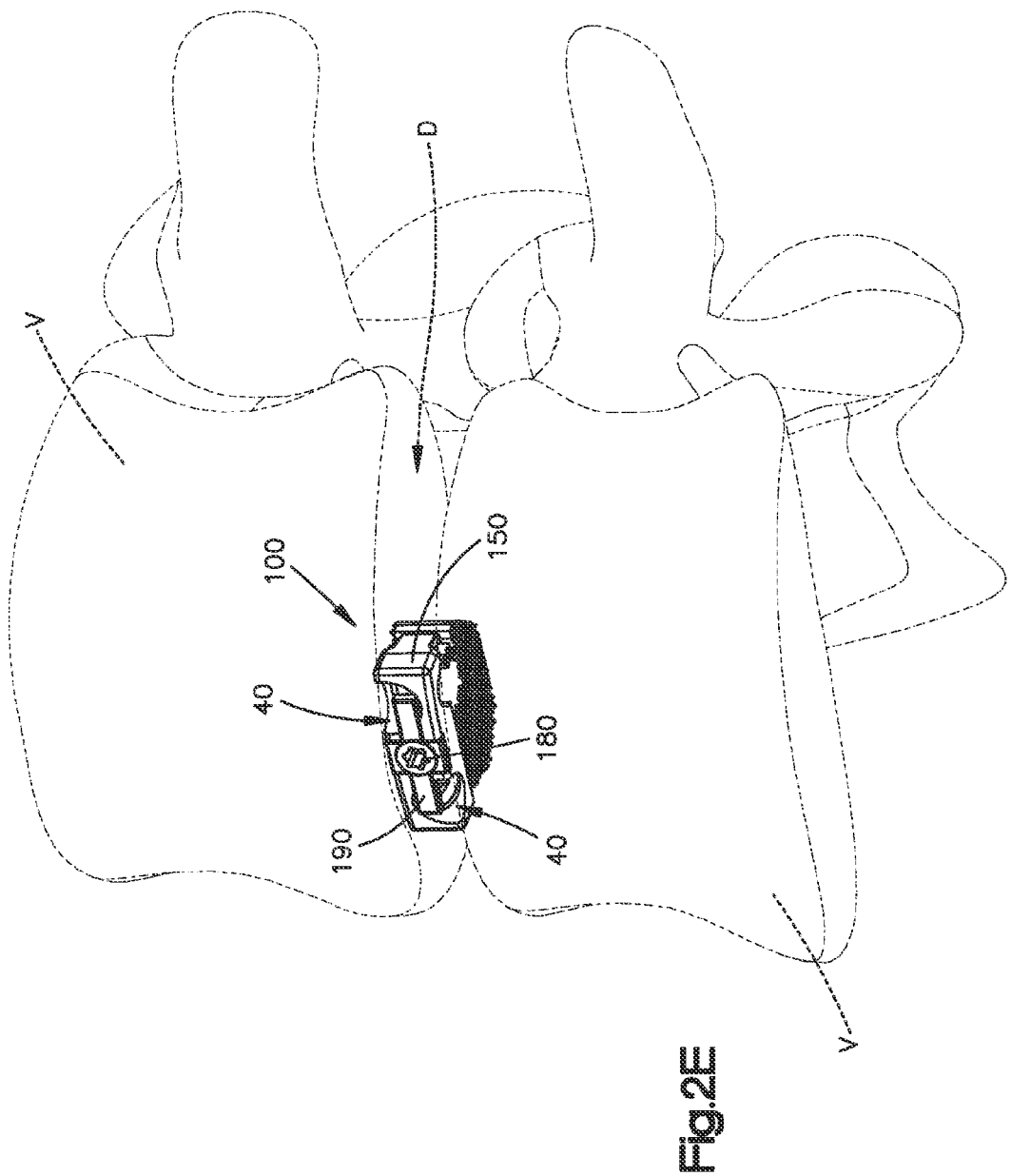

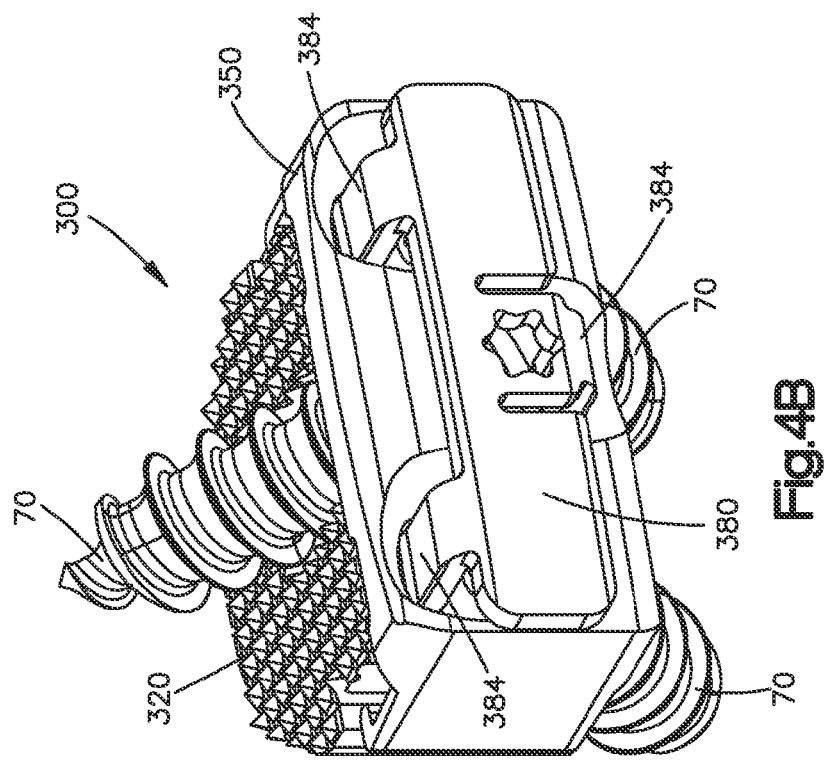
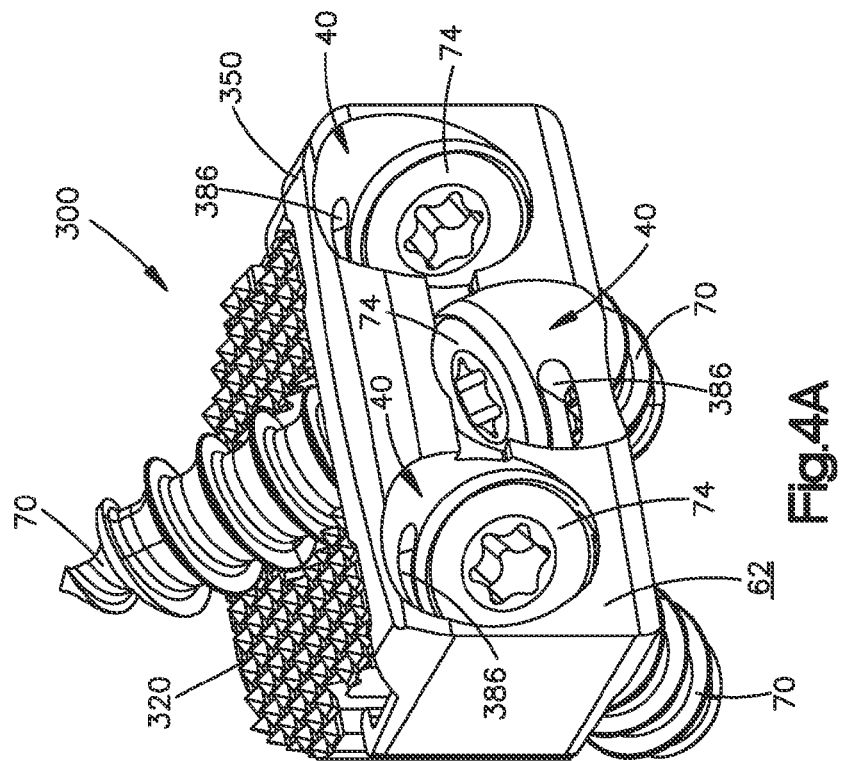

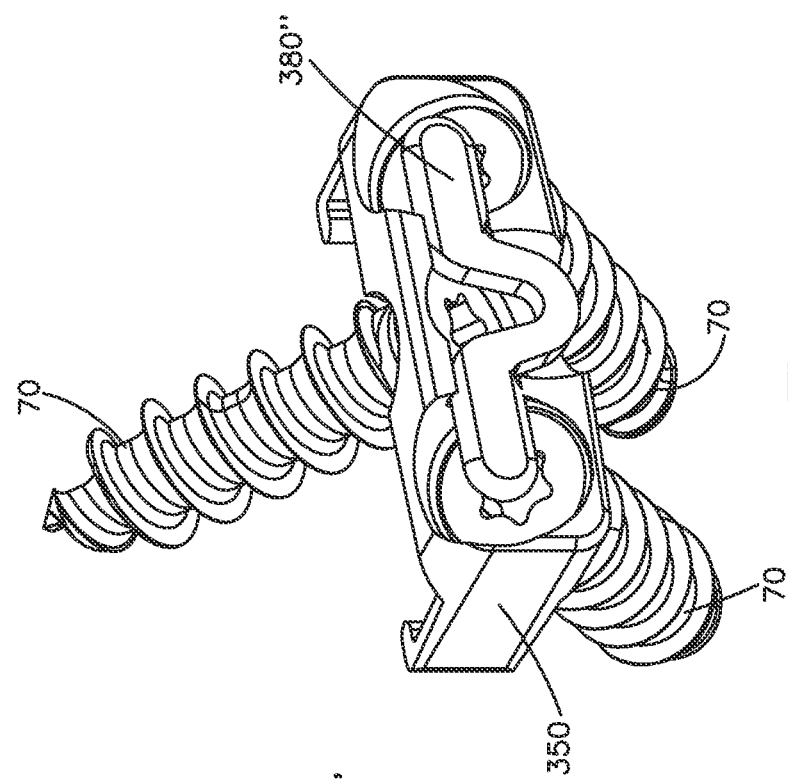
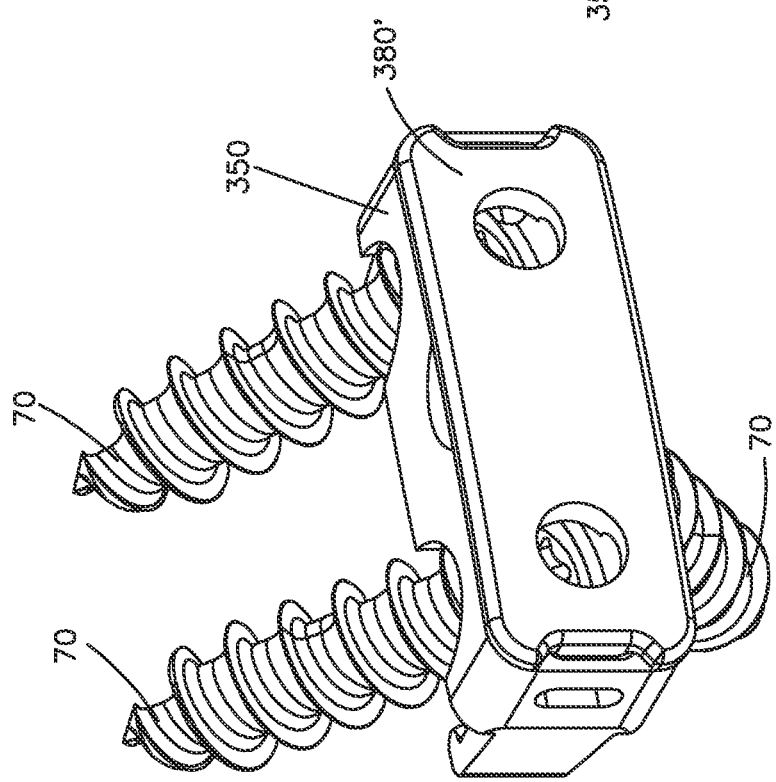

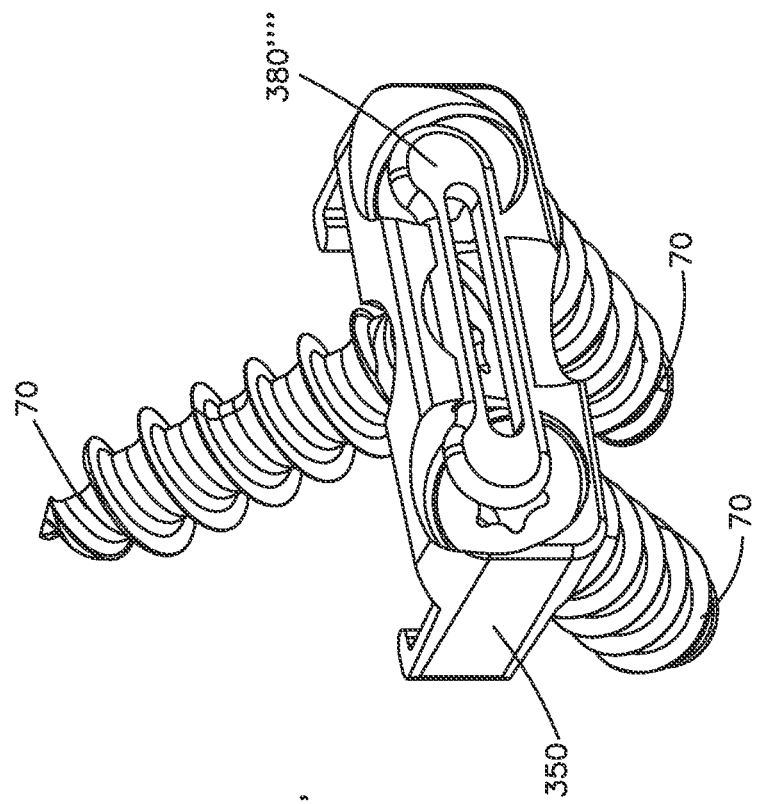
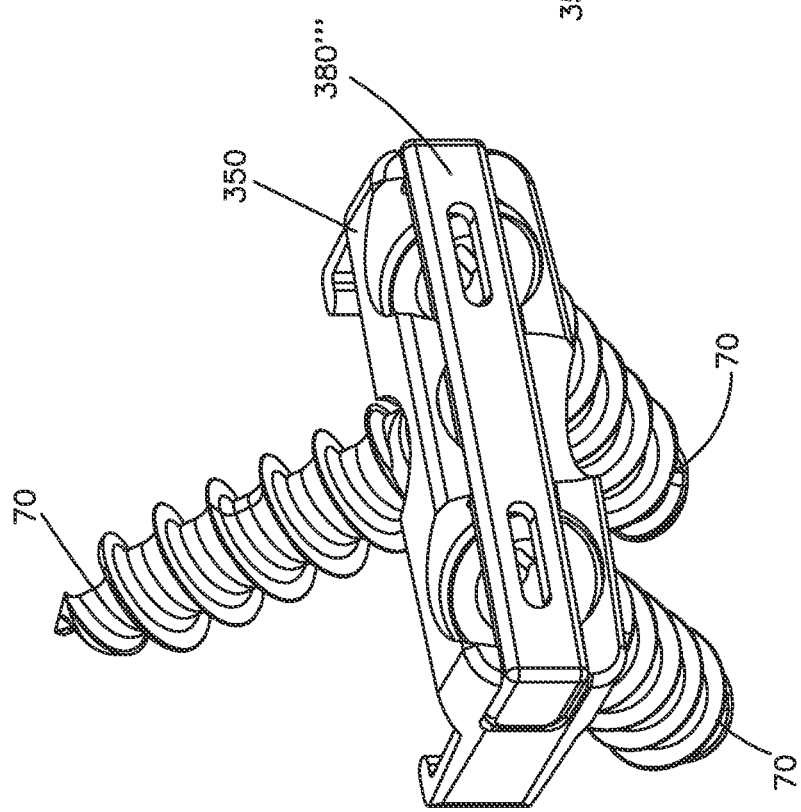

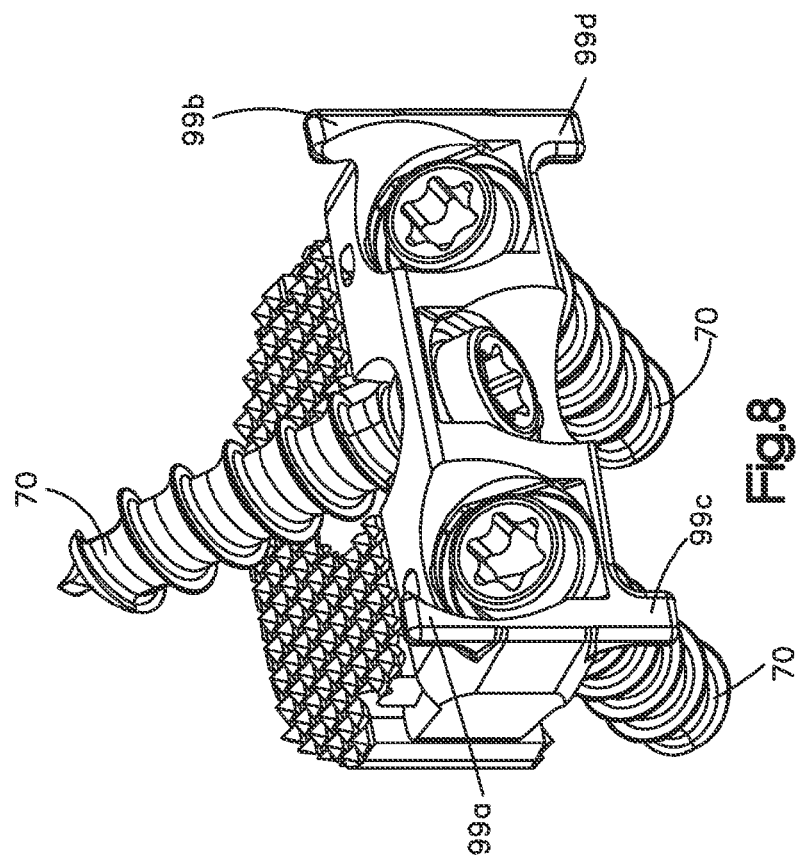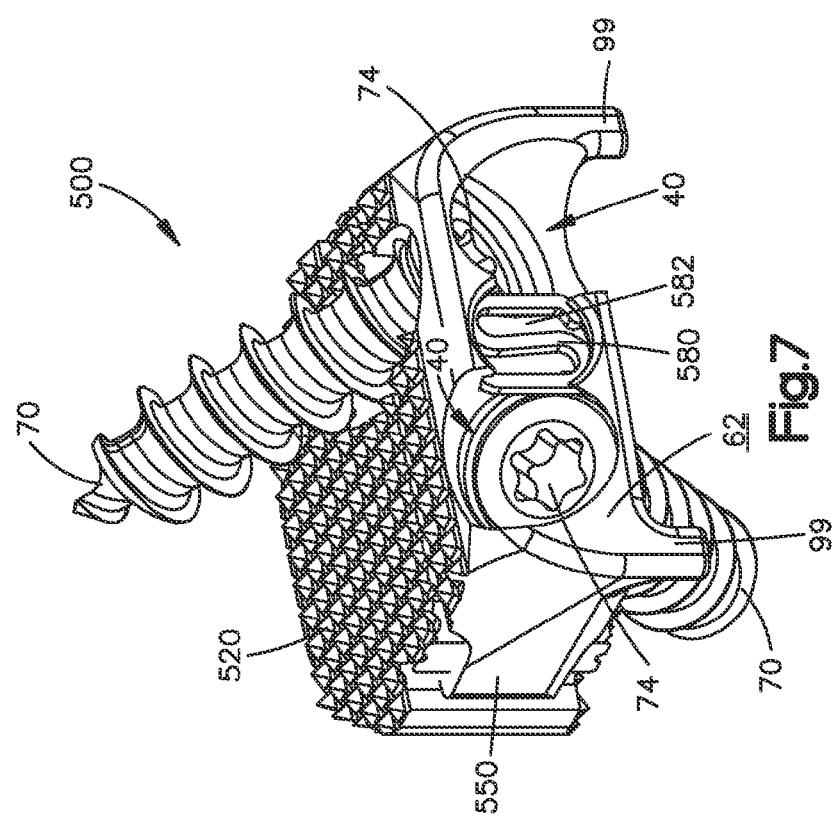

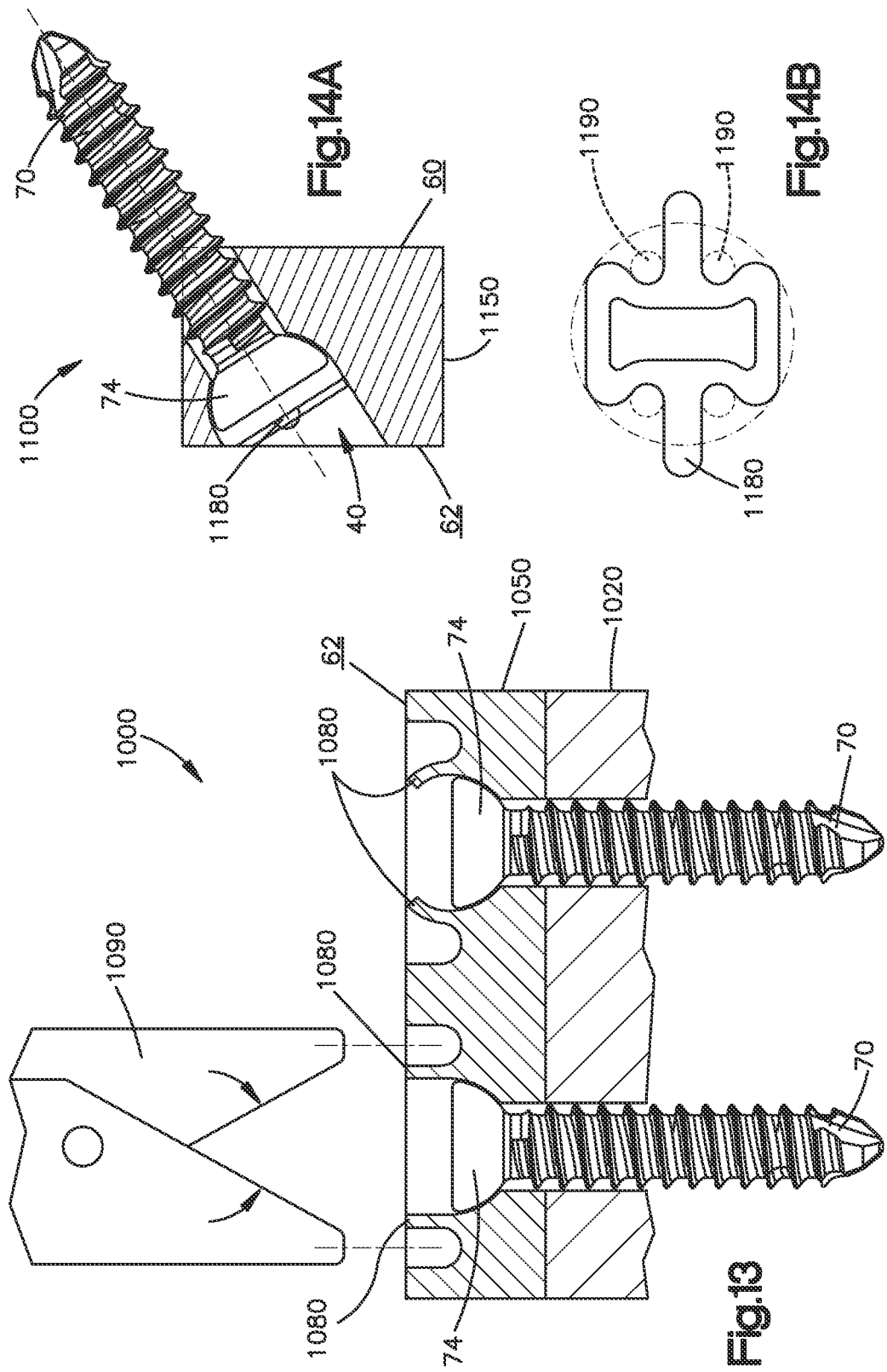

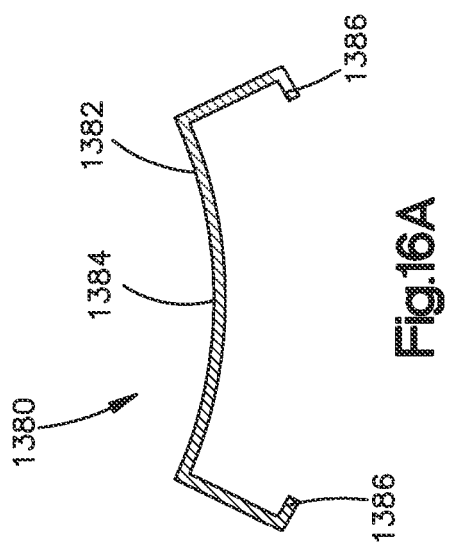
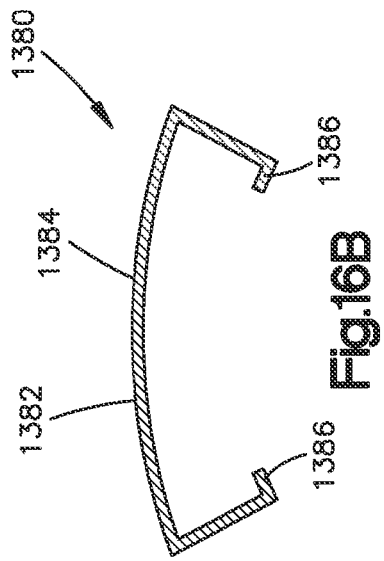
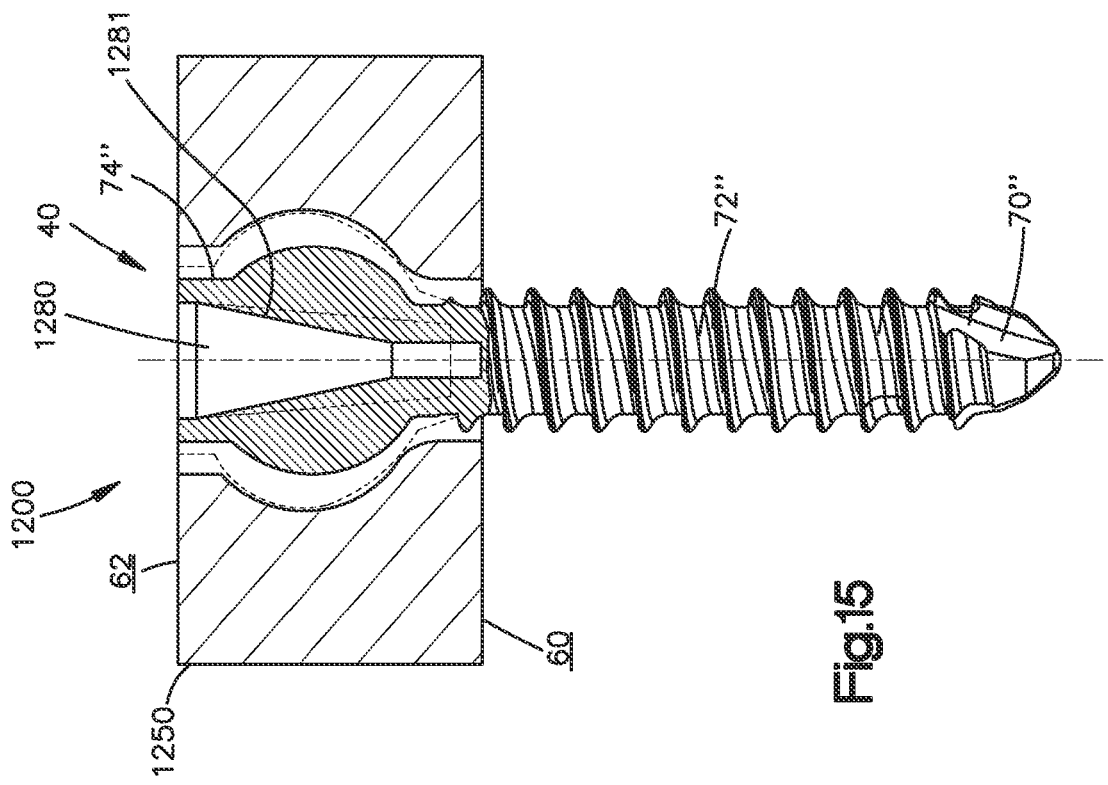

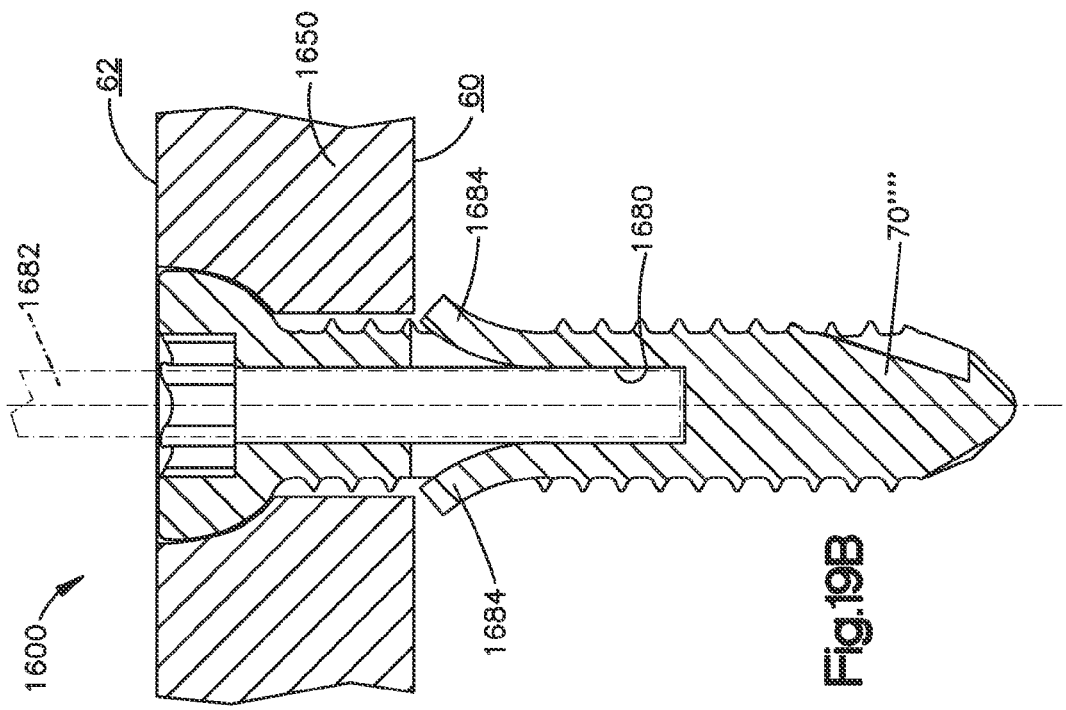
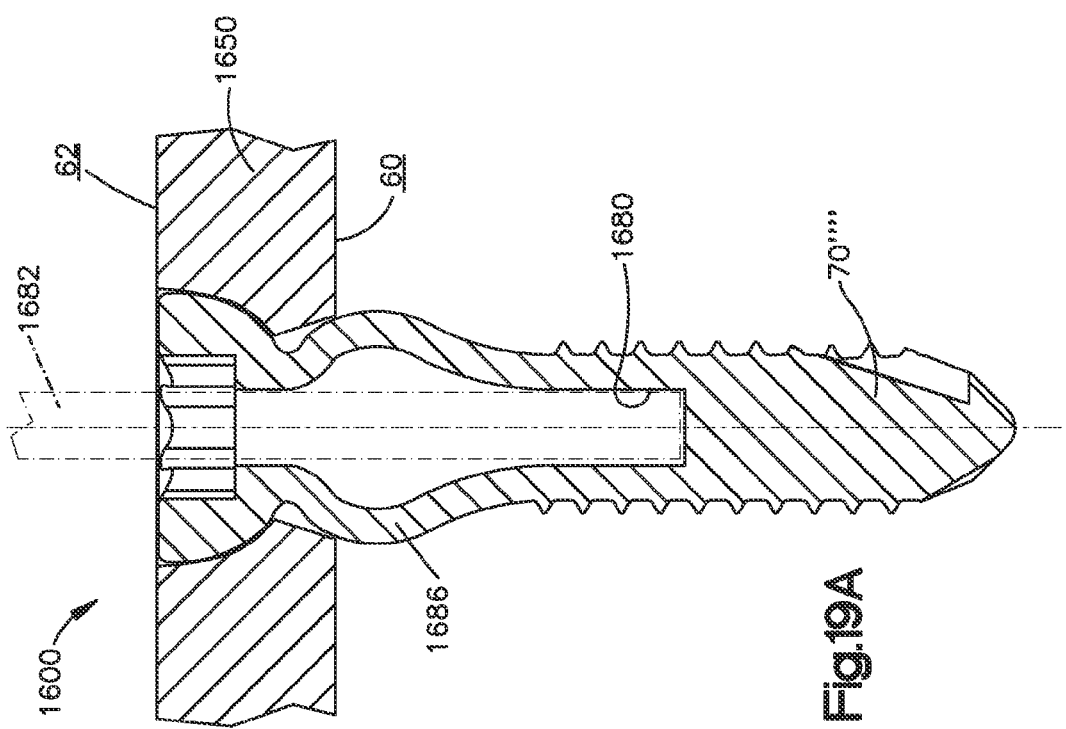

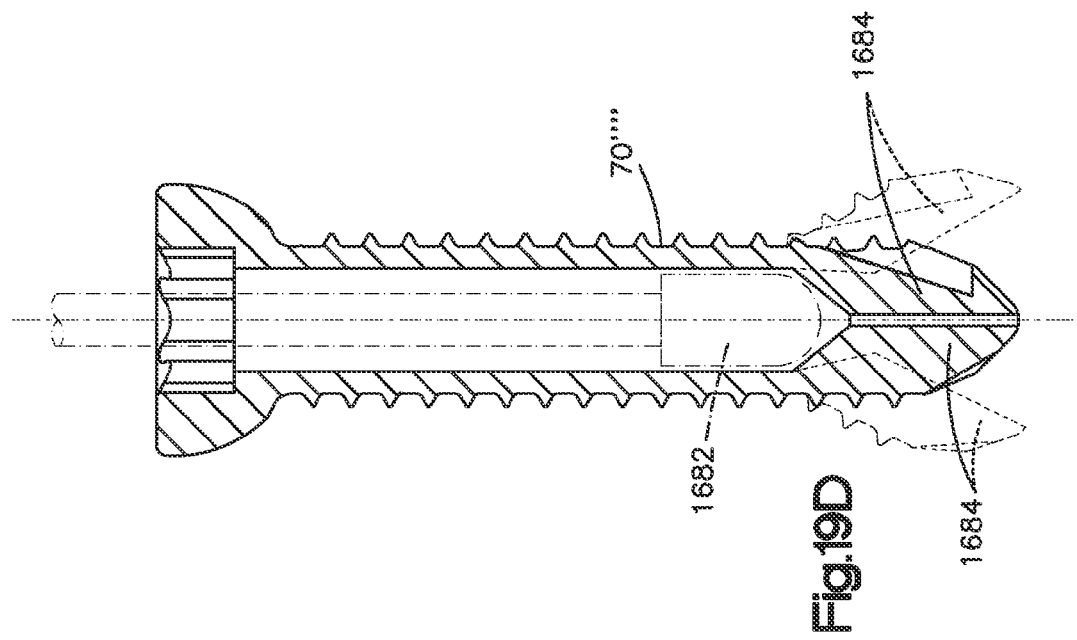
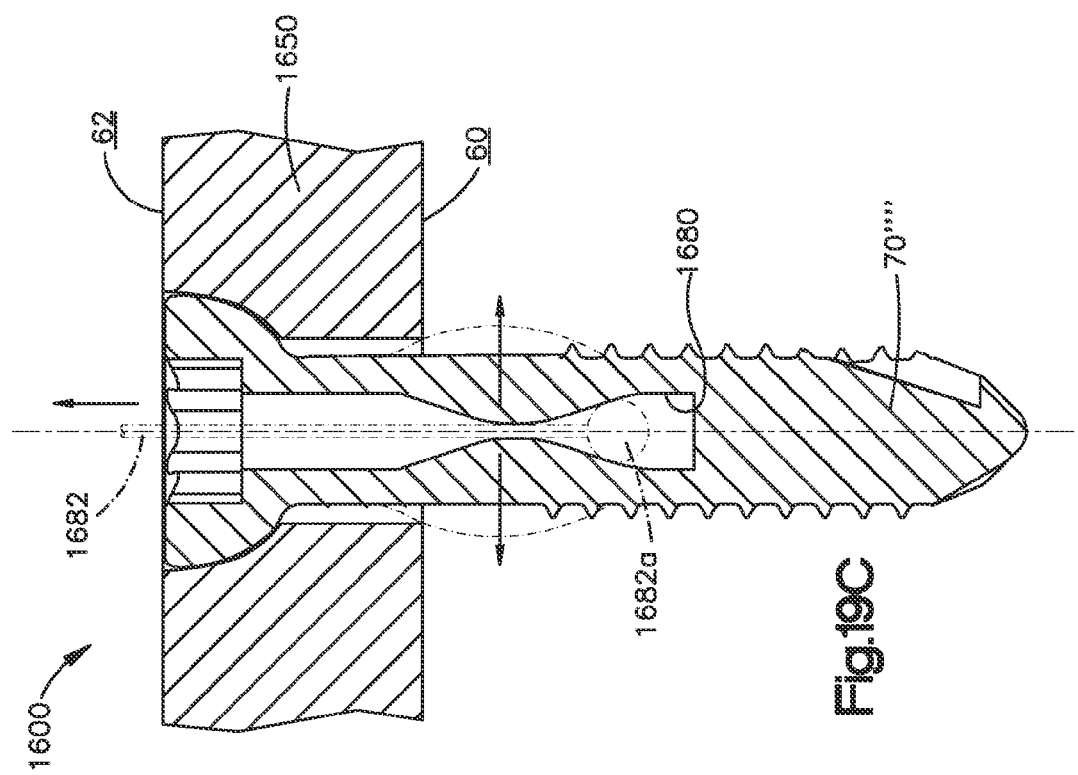

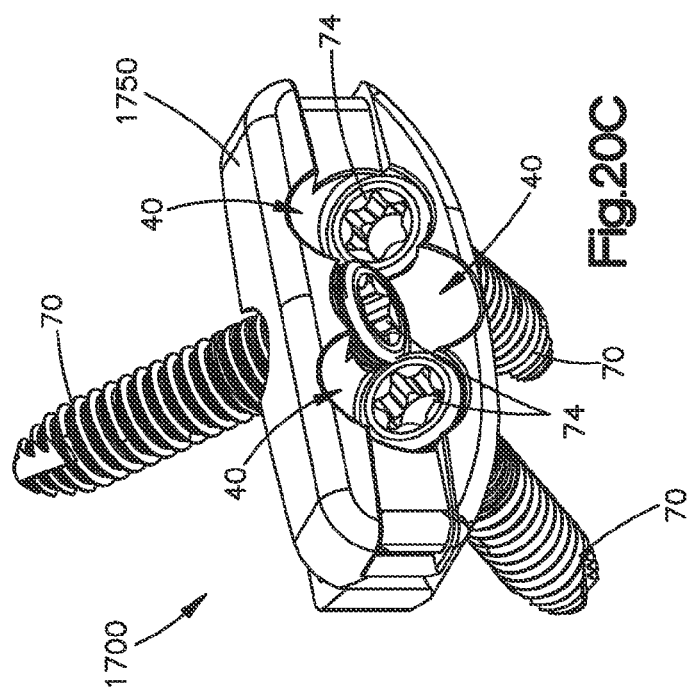
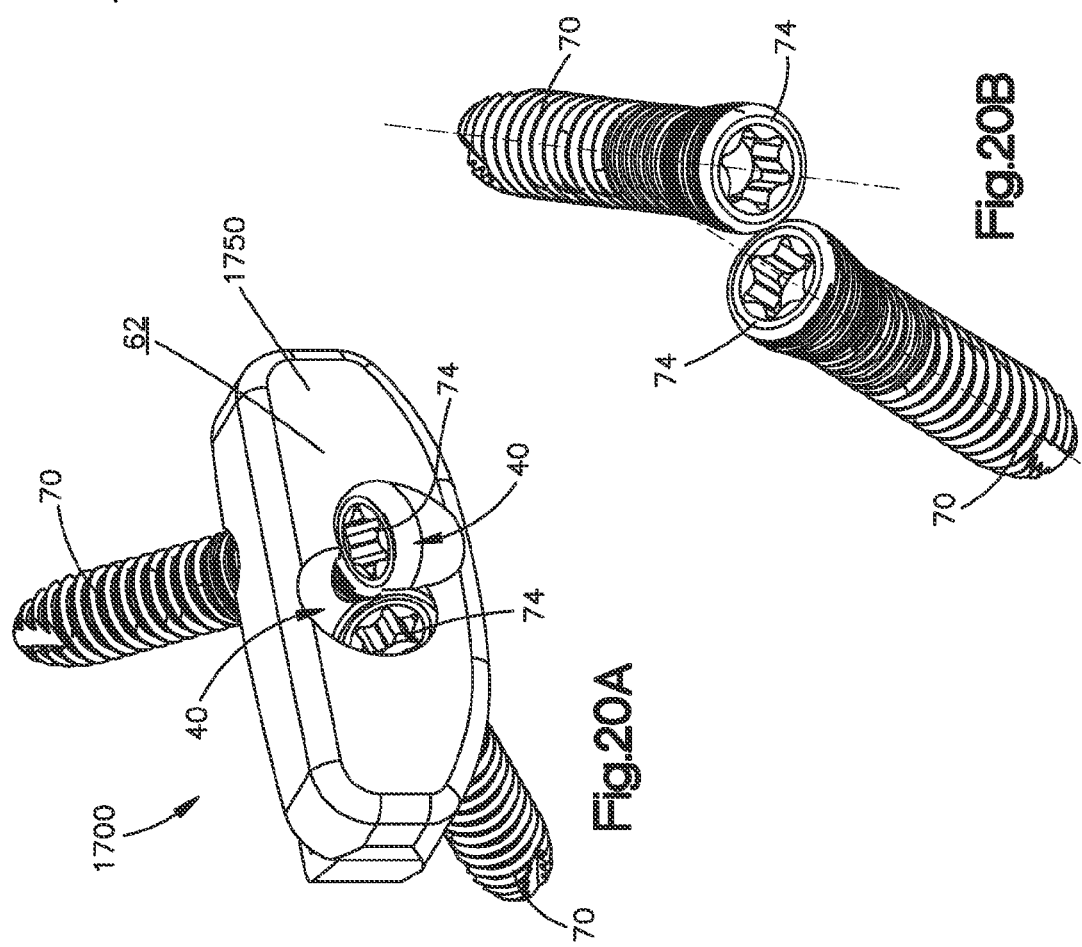

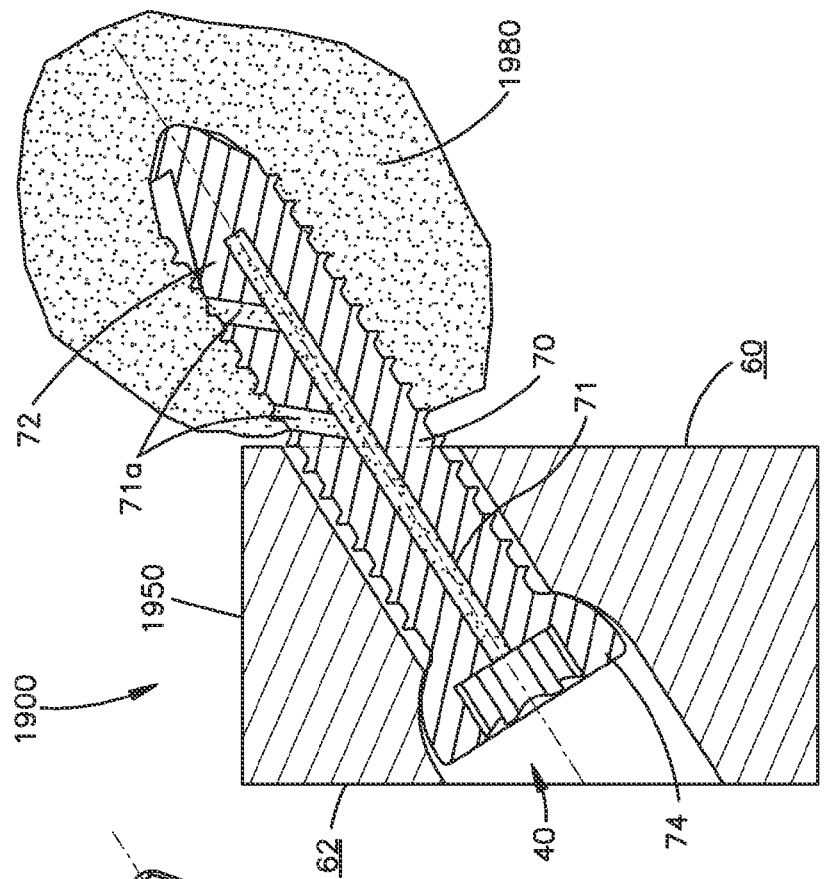
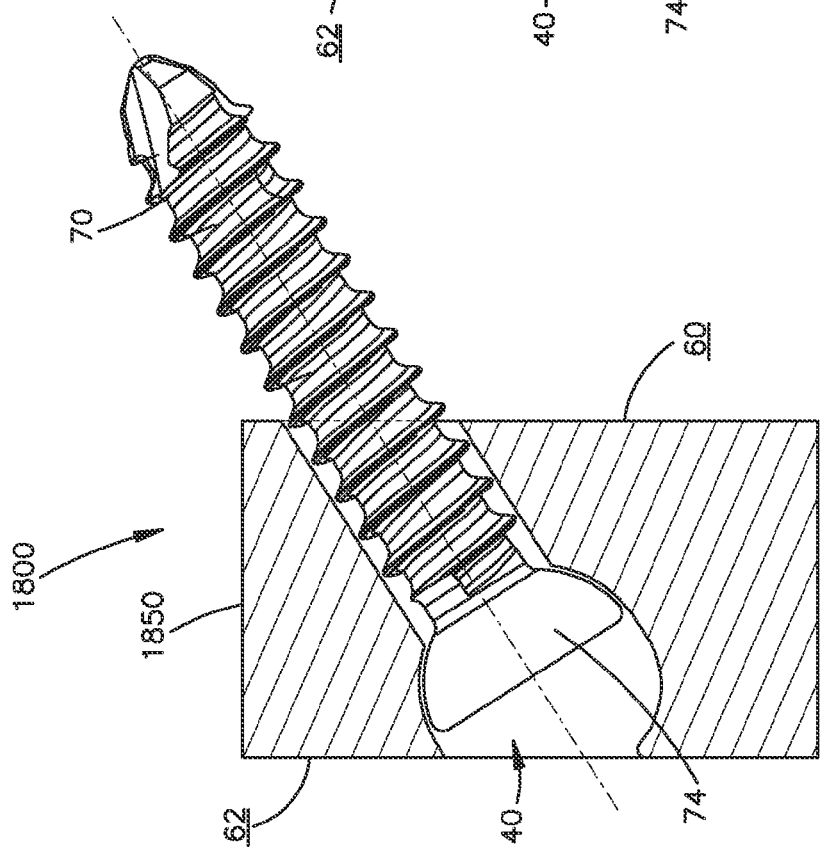

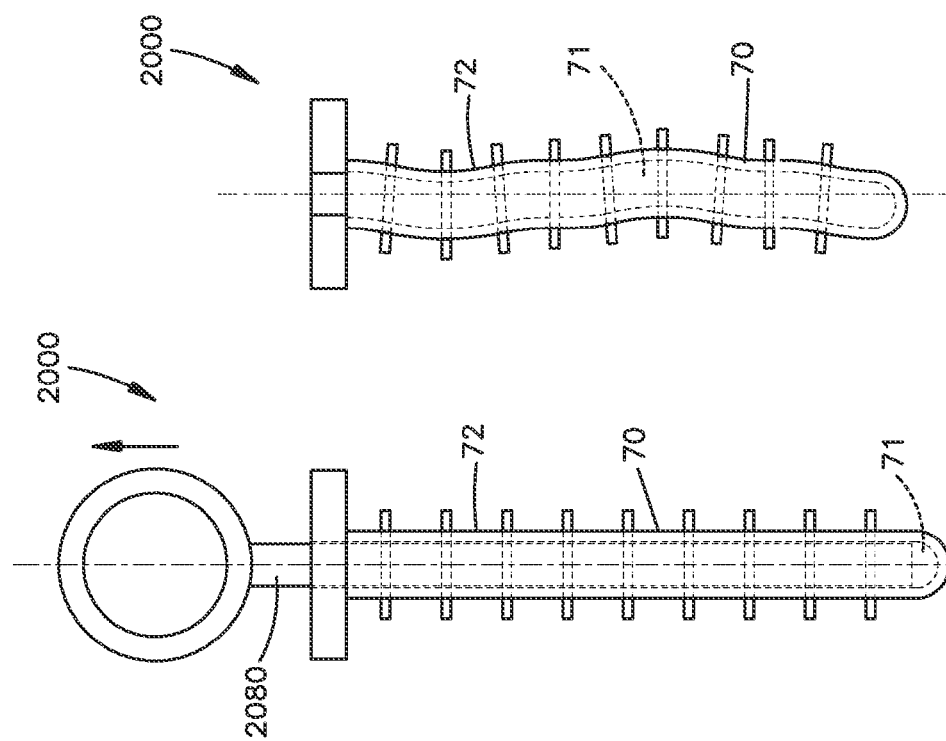
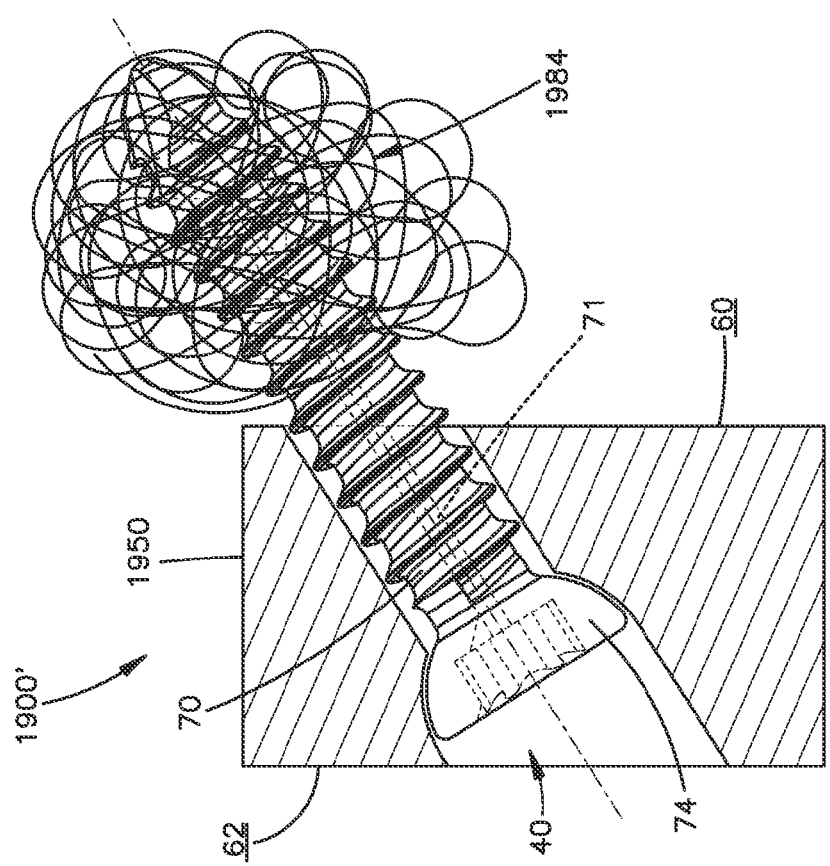

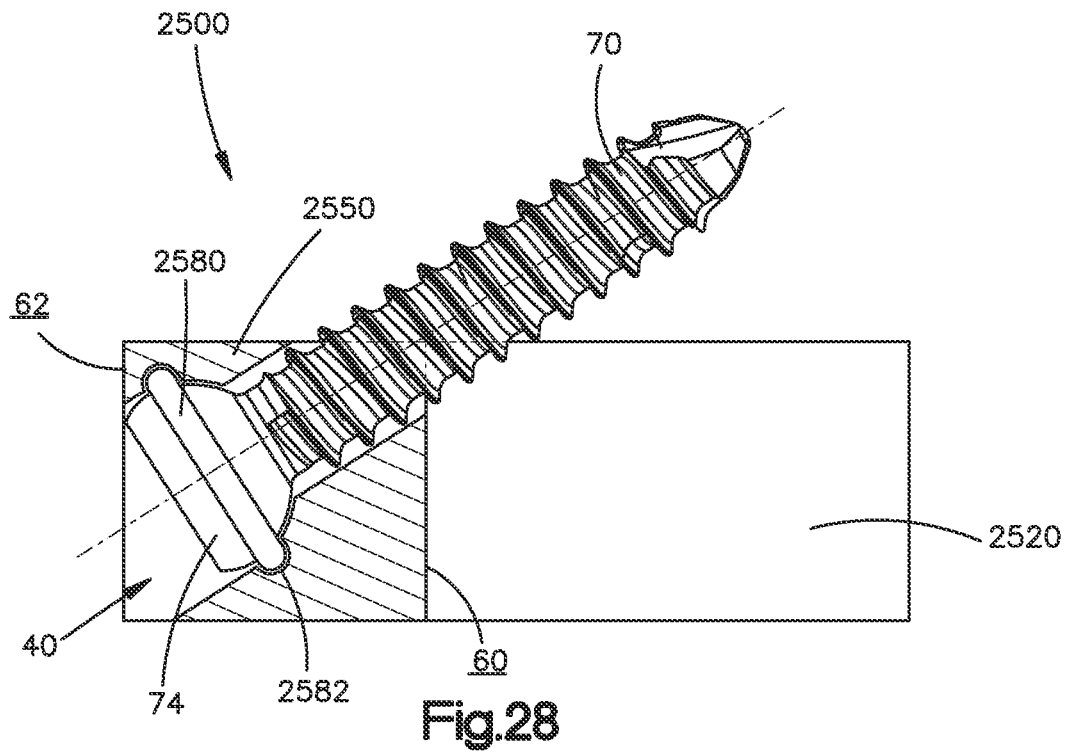
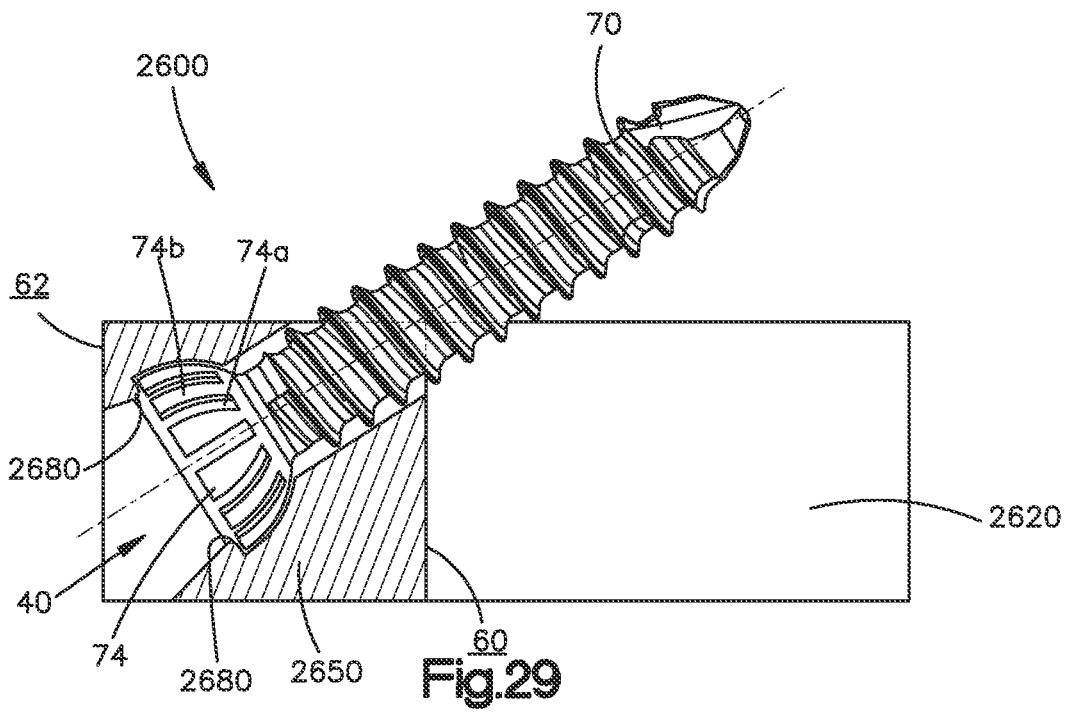

US 9,402,735 B2

ZERO-PROFILE INTERBODY SPACER AND COUPLED PLATE ASSEMBLY

CROSS REFERENCE TO RELATED APPLICATIONS

This application is a continuation of U.S. patent application Ser. No. 12/614,082, filed Nov. 6, 2009, entitled Zero-Profile Interbody Spacer and Coupled Plate Assembly, which claims priority to U.S. Provisional Patent Application No. 61/112,441, filed Nov. 7, 2008, entitled "Zero-Profile Interbody Spacer and Coupled Plate Assembly" and U.S. Provisional Patent Application No. 61/139,920, filed Dec. 22, 2008, entitled "Screw and Plate Locking Mechanisms for Smaller Bone Plates", the contents of which are hereby incorporated by reference in their entirety.

BACKGROUND OF THE INVENTION

Intervertebral implants including interbody spacer portions and mechanically coupled plate portions are known in the art for restoring disc height, allowing fusion to occur between the adjacent vertebral bodies, and for providing stable fixation during healing.

It is desirable to construct a zero-profile implant wherein the bone fixation elements that secure the implant to the vertebral bodies are blocked from backing-out of the bone and/or plate. Additionally, it is desirable to construct a zero-profile implant that includes polyaxial bone fixation element couplings and features that prevent the implant from being implanted too deeply into a prepared disc space. Both screw back-out and over-insertion of the implant into a prepared disc space can have an adverse impact on the performance of the implant.

BRIEF SUMMARY OF THE INVENTION

The present invention relates generally to a spinal implant. More specifically, the present invention relates to a zero profile interbody spacer and coupled plate assembly for insertion into a disc space between adjacent superior and inferior vertebral bodies. Preferably, the implant is sized and configured for use in the cervical region of the spine, where a very limited amount of space is available.

The implant preferably includes a spacer portion, a plate portion coupled to the spacer portion, a plurality of bone fixation elements for engaging the vertebral bodies and a retention mechanism for preventing the bone fixation elements from postoperatively uncoupling from the implant.

The spacer portion preferably includes a top surface for contacting the superior vertebral body, a bottom surface for contacting the inferior vertebral body, a first side surface, a second side surface, a leading surface and a trailing surface. The plate portion includes a top surface, a bottom surface, a first side surface, a second side surface, a leading surface, a trailing surface and one or more bone fixation holes for receiving the one or more bone fixation elements. Preferably, the implant includes at least two bone fixation holes for receiving at least two bone fixation elements. The first bone fixation hole is angled so that the first bone fixation element engages the superior vertebral body while the second bone fixation hole is angled so that the second bone fixation element engages the inferior vertebral body.

The retention mechanism may be in the form of any of the numerous retention mechanisms disclosed herein. The retention mechanism generally operates to engage or block subsequent movement of the bone fixation elements in order to prevent the bone fixation elements from backing-out of the bone fixation holes formed in the plate portion (e.g., from postoperatively uncoupling from the implant).

The implant preferably also includes one or more stops, more preferably first and second stops, to prevent over-insertion of the implant during implantation and to assist in securing a position of the implant during insertion of the bone fixation elements. The first stop preferably extends superiorly of the top surface of the plate portion for contacting the superior vertebral body while the second stop extends inferiorly of the bottom surface of the plate portion for contacting the inferior vertebral body. The first and second stops are preferably integrally formed with the plate portion.

BRIEF DESCRIPTION OF THE SEVERAL VIEWS OF THE DRAWINGS

The foregoing summary, as well as the following detailed description of preferred embodiments of the application, will be better understood when read in conjunction with the appended drawings. For the purposes of illustrating the implant of the present application, there is shown in the drawings preferred embodiments. It should be understood, however, that the application is not limited to the precise arrangements and instrumentalities shown. In the drawings:

FIGS. 2A-2E illustrate various perspective views of an implant according to a second preferred embodiment, the implant being inserted into an intervertebral disc space between adjacent vertebral bodies via an exemplary implant inserter instrument.

FIG. 4A illustrates an anterior perspective view of an implant according to a fourth preferred embodiment of the present application;

FIG. 4B illustrates an anterior perspective view of the implant of FIG. 4A with a blocking plate retention mechanism coupled thereto;

FIGS. 5A-5D illustrate various perspective views of additional blocking plate geometries and securing mechanisms;

FIG. 7 illustrates a partial anterior perspective view of an implant according to a sixth preferred embodiment of the present application, the implant incorporating first and second stops;

FIG. 8 illustrates an alternate anterior perspective view of the implant of FIG. 7, the implant incorporating first, second, third and fourth stops;

FIG. 13 illustrates a cross-sectional view of an implant according to an eleventh preferred embodiment of the present invention;

FIG. 14A illustrates a partial cross-sectional elevational view of a plate portion, a bone fixation element and a retention mechanism of an implant according to a twelfth preferred embodiment of the present invention;

FIG. 14B illustrates an elevational view of the retention mechanism of the implant of FIG. 14A, the retention mechanism being illustrated in a deformed, reduced configuration;

FIG. 15 illustrates a partial cross-sectional view of a plate portion, a bone fixation element and a retention mechanism of an implant according to a thirteenth preferred embodiment of the present invention;

FIG. 16A illustrates an elevational view of a retention mechanism of an implant according to a fourteenth preferred embodiment, the retention mechanism being illustrated in an open, enlarged configuration;

FIG. 16B illustrates an elevational view of the retention mechanism of FIG. 16A, the retention mechanism being illustrated in a closed, biased configuration;

FIG. 19A illustrates a partial cross-sectional view of a plate portion, a bone fixation element and a retention mechanism of an implant according to a seventeenth preferred embodiment of the present invention;

FIG. 19B illustrates an alternate partial cross-sectional view of a plate portion, a bone fixation element and a retention mechanism of the implant of FIG. 19A;

FIG. 19C illustrates an alternate partial cross-sectional view of a bone fixation element and a retention mechanism of the implant of FIG. 19A;

FIG. 19D illustrates a side elevational view of a bone fixation element and a retention mechanism of the implant of FIG. 19A;

FIG. 20A illustrates a partial anterior, perspective view of a plate portion, a bone fixation element and a retention mechanism of an implant according to an eighteenth preferred embodiment of the present invention;

FIG. 20B illustrates a cross-sectional view of the bone fixation elements and retention mechanism of the implant of FIG. 20A;

FIG. 20C illustrates an alternate partial anterior, perspective view of a plate portion, a bone fixation element and a retention mechanism of the implant of FIG. 20A;

FIG. 21 illustrates a partial cross-sectional elevational view of a plate portion, a bone fixation element and a retention mechanism of an implant according to a nineteenth preferred embodiment of the present invention;

FIG. 22 illustrates a partial cross-sectional elevational view of a plate portion, a bone fixation element and a retention mechanism of an implant according to a twentieth preferred embodiment of the present invention;

FIG. 22A illustrates an alternate partial cross-sectional elevational view of a plate portion, a bone fixation element and a retention mechanism of the implant of FIG. 22;

FIG. 23A illustrates a cross-sectional view of a bone fixation element and a retention mechanism of an implant according to a twenty-first preferred embodiment of the present invention, the bone fixation element and retention mechanism being illustrated in a first insertion configuration;

FIG. 23B illustrates a cross-sectional view of the bone fixation element of FIG. 23A, the bone fixation element being illustrated in a second inserted configuration;

FIG. 28 illustrates a cross-sectional elevational view of a spacer portion, a plate portion, a bone fixation element and a retention mechanism of an implant according to a twenty-sixth preferred embodiment of the present invention;

FIG. 29 illustrates a partial cross-sectional elevational view of a spacer portion, a plate portion, a bone fixation element and a retention mechanism of an implant according to a twenty-seventh preferred embodiment of the present invention;

DETAILED DESCRIPTION OF THE INVENTION

Figure 1:
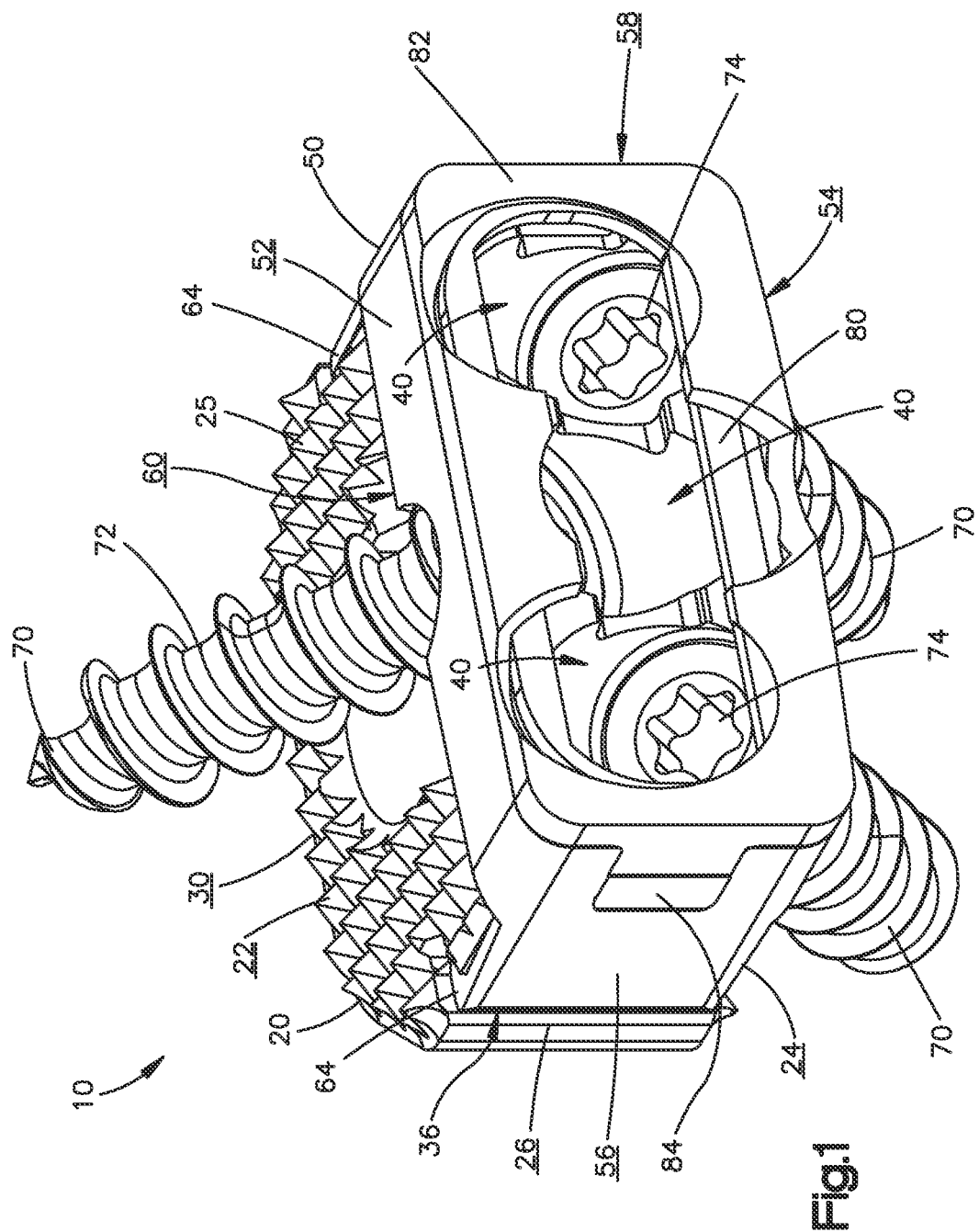
FIG. 1 illustrates an anterior perspective view of an implant according to a first preferred embodiment of the present application.

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the geometric center of the implant and related parts thereof. The words, "anterior", "posterior", "superior," "inferior" and related words and/or phrases designate preferred positions and orientations in the human body to which reference is made and are not meant to be limiting. The terminology includes the above-listed words, derivatives thereof and words of similar import.

Similar reference numerals will be utilized throughout the application to describe similar or the same components of each of the preferred embodiments of the implant described herein and the descriptions will focus on the specific features of the individual embodiments that distinguish the particular embodiment from the others.

Preferred embodiments of the present application are directed to an implant 10-2800. It should be understood that while the various embodiments of the implant 10-2800 will be described in connection with spinal surgery, those skilled in the art will appreciate that the implant 10-2800, as well as the components thereof, may be used for implantation into other parts of the body, including, for example, long bones or bones in the knee, hip, shoulder, or other joint replacement or for bone augmentation.

The various embodiments of the implant 10-2800 are preferably sized and configured to be implanted between adjacent vertebral bodies V. The implant 10-2800 may be sized and configured to replace all or substantially all of an intervertebral disc space D between adjacent vertebral bodies V or only part of the intervertebral disc space D. In addition, the preferred implant 10-2800 may be configured to replace an entire vertebral body V and related disc spaces D or multiple disc spaces D in a patient's spine, as would be apparent to one having ordinary skill in the art based upon a review of the present application. The implant 10-2800 may be adapted for use in the anterior, anterolateral, direct lateral, extra-foraminal, transforaminal, and posterior approaches for insertion into the spine.

The implant 10-2800 of each of the preferred embodiments includes an interbody spacer portion 20-2820 and a plate portion 50-2850. The spacer portion 20-2820 is preferably sized and configured for implantation into the intervertebral disc space D between adjacent vertebral bodies V. The spacer portion 20-2820 of each of the preferred embodiments includes a top surface 22, a bottom surface 24, a first side surface 26, a second side surface 28, a leading surface 30 and a trailing surface 32. The top and bottom surfaces 22, 24 are suitable for contacting and are adapted for being secured relative to the end plates of adjacent vertebral bodies V. The spacer portion 20-2820 is preferably sized and configured to maintain and/or restore a desired intervertebral disc height between the adjacent vertebral bodies V. Accordingly, the top and bottom surfaces 22, 24 may include a series of teeth, ridges, spikes or other similar projections 25 to aid in securing the implant 10-2800 to the endplates of the adjacent vertebral bodies V.

The top and bottom surfaces 22, 24 may also include a curved or a tapered surface to help provide an anatomical shape for mating with the patient's spine or to orient the endplates of the adjacent vertebral bodies V in a desired manner. The particular surface shape and curvature, taper or alternate surface feature in the anterior-posterior direction, as well as the particular surface shape and curvature, taper or alternate surface feature in the medial-lateral direction will depend upon the location where the implant 10-2800 is intended to be implanted and/or surgeon preferences or whether the implant 10-2800 is utilized in another area in the body.

The spacer portion 20-2820 may also include one or more boreholes, openings, windows or channels for receiving bone graft material. For example, the implant 10-2800 may include one or more vertical openings, windows or channels extending through the spacer portion from the top surface 22 to the bottom surface 24 for insertion of bone graft material, such that bone growth is promoted through the vertical openings, windows or channels following implantation of the implant 10-2800. One or more boreholes, openings, windows or channels is especially preferred if the spacer portion 20-2820 is constructed of a non-allograft or non-bone-growth material, such as Polyetheretherketone ("PEEK").

The plate portion 50-2850 is preferably coupled to the spacer portion 20-2820 to provide increased implant stability during healing as well as to optimally orient the trajectory of bone fixation elements 70 during implantation.

The plate portion 50-2850 of each of the preferred embodiments includes a top surface 52, a bottom surface 54, a first side surface 56, a second side surface 58, a leading surface 60 and a trailing surface 62. The plate portion 50-2850 preferably contacts the trailing surface 32 of the spacer portion 20-2820 and preferably does not extend beyond or does not increase greatly the vertical or lateral perimeter of the spacer portion 20-2820. In this manner, the implant 10-2800 has a low profile. Additionally, in this manner, the plate portion 50-2850 is preferably entirely implanted within the intervertebral disc space D between the adjacent vertebral bodies V such that the plate portion 50-2850 has little or no external profile (e.g., the plate portion 50-2850 does not extend anterior beyond an edge of the disc space D). In this manner, little or no structure protrudes outside of the bounds of the disc space D or the profile of the vertebral bodies V, thereby limiting dysphasia and patient discomfort. In use, the plate portion 50-2850 may be sized and configured so that the top and bottom surfaces 52, 54 of the plate portion 50-2850 contact the endplates of the adjacent vertebral bodies V. Alternatively, the plate portion 50-2850 may be sized and configured so that only the spacer portion 20-2820 contacts the adjacent vertebral bodies V. For example, the height of the plate portion 50-2850 may be small enough so that it does not contact the vertebral bodies V when connected to the spacer portion 20-2820 in an implanted position.

The plate portion 50-2850 may be coupled to the spacer portion 20-2820 by any coupling mechanism now or hereafter known. For example, the spacer portion 20-2820 may include one or more recesses 36 formed in the side or trailing surfaces for engaging one or more projections 64 extending from the plate portion 50-2850. Preferably the spacer portion 20-2820 includes a recess 36 formed in each of the side surfaces 26, 28 thereof for engaging projections 64 extending from the plate portion 50-2850. The recesses 36 may extend completely from the top surface 22 to the bottom surface of the spacer portion 20-2820 or may extend only partially from either the top or bottom surface 20, 22. Other coupling mechanisms for coupling the plate portion 50-2850 to the spacer portion 20-2820 are disclosed in International Application No. PCT/US2008/082473 filed on Nov. 5, 2008 and entitled, "Low Profile Intervertebral Implant", the contents of which are hereby incorporated by reference in their entirety.

The trailing surface 62 of the plate portion 50-2850 preferably includes a tool engagement feature (not shown) for engaging one or more insertion tools. The tool engagement feature may be in any form now or hereafter known for such purpose including one or more recesses (not shown) formed in the trailing surface 62 of the plate portion 50-2850, the recesses extending from top and bottom surfaces 52, 54, respectively, for engaging arms of the insertion tool (not shown). Alternatively, the tool engagement feature may be a threaded bore (not shown) formed in the trailing surface 62 of the plate portion 50-2850 for engaging a threaded stem extending from the insertion tool, etc.

The implant 10-2800 preferably includes one or more bone fixation holes 40 for receiving one or more bone fixation elements 70, preferably bone screws so that, in use, after the implant 10-2800 has been inserted into the intervertebral disc space D between adjacent vertebral bodies V, the implant 10-2800 may be secured to the adjacent vertebral bodies V. The bone fixation elements 70 preferably include a threaded shaft 72 and a partially spherical head portion 74 that is generally smooth where it contacts the bone fixation hole 40. The threaded shaft 72 may be self-drilling, i.e. does not necessitate the drilling of pilot holes, but are not so limited. The bone fixation elements 70 are not limited to bone screws 70 and may be comprised of a helical nail, a distally expanding nail or screw, etc. The bone fixation holes 40 are preferably sized and configured so that the head portion 74 of the bone fixation elements 70 do not protrude proximally beyond the trailing surface 62 of the plate portion 50, when the bone fixation elements 70 have been fully implanted.

The bone fixation holes 40 preferably include a curved or frusta-spherical surface for contacting an underside of the generally smooth or frustaspherical surface of the head portion 74 of the bone fixation elements 70 so that the bone fixation elements 70 can polyaxially rotate with respect to the plate portion 50-2850 and a variety of trajectory angles can be chosen for the bone fixation elements 70 according to surgeons' preferences or needs as well as to enable the implant 10-2800 to settle during healing. Post implantation, the bone fixation elements 70 are preferably free to toggle to allow for settling during postoperative healing. If a surgeon decides the placement of the implant 10-2800 is not optimal, adjustments can be made by moving the retention mechanism (as will be described in greater detail below) with, for example a blunt instrument, to allow the bone fixation elements 70 to be removed.

The plate portion 50-2850 preferably includes at least first and second bone fixation holes 40 for receiving at least first and second bone fixation elements 70 with the first bone fixation element 70 being angled upwardly for engaging the superior vertebral body V and the second bone fixation element 70 being angled downwardly for engaging the inferior vertebral body V. That is, the bone fixation holes 40 preferably have a longitudinal axis that is oriented obliquely with respect to the implant 10-2800 so that the bone fixation elements 70 form a fastener angle with respect to the top and bottom surfaces 22, 24 of the spacer portion 20-2820 wherein bone fixation angle may be in the range between twenty degrees (20°) and sixty degrees (60°), and more preferably between thirty degrees (30°) and fifty degrees (50°). The bone fixation angle may be the same for all of the holes 40 or may be different for each of the holes 40. In addition, the bone fixation holes 40 may be directed inwardly toward the center of the implant 10-2800 or outwardly away from the center of the implant 10-2800, preferably at a lateral bone fixation angle α so that the bone fixation elements 70 extend laterally inward toward a center plane of the implant 10-2800 or laterally outward away from the center plane of the implant 10-2800. The lateral bone fixation angle α may be in the range between plus sixty degrees (60°) and minus sixty degrees)(−60°, preferably between zero degrees (0°) and plus or minus thirty degrees (30°), and more preferably about plus or minus fifteen degrees (15°). The lateral bone fixation angle α may be the same for all holes 40 or may be different for each hole 40. However, as would be understood by one of ordinary skill in the art based upon a reading of this disclosure, a plurality of potential angles is possible since the bone fixation elements 70 are polyaxial, as will be described in greater detail below.

It should be understood however that the implant 10-2800 may include any number of bone fixation holes 40 configured to receive a corresponding number of bone fixation elements 70 in any number of configurations. In addition, the number of bone fixation elements 70 extending from the top and bottom surfaces 22, 24 may be varied and the number of bone fixation elements 70 extending from the top surface 22 need not equal the number of bone fixation elements 70 extending from the bottom surface 24.

Exit openings for the bone fixation holes 40 preferably are formed at least partially in the top or bottom surfaces 52, 54 of the plate portion 50-2850. The exit openings may also be formed at least partially or entirely in the top or bottom surfaces 22, 24 of the spacer portion 20-2820. The bone fixation holes 40 may also include a partially spherical interior volume to accommodate the partially spherical geometry of the head portion 74 of the bone fixation elements 70 to enable a range of polyaxial orientations to be chosen for the bone fixation elements 70 with respect to the vertebral bodies V.

The implant 10-2800 preferably includes a retention mechanism for reducing the likelihood that the bone fixation elements 70 may postoperatively uncouple from the implant 10-2800 and migrate from the disc space D. In use, the retention mechanism preferably engages or contacts the bone fixation element 70 or blocks or covers at least a portion of the bone fixation holes 40 and hence the bone fixation elements 70 to prevent the bone fixation elements 70 from backing-out, as will be described in greater detail below.

The implant 10-2800 including the spacer portion 20-2820 and the plate portion 50-2850 may be constructed of any suitable biocompatible material or combination of materials including, but not limited to one or more of the following metals such as titanium, titanium alloys, stainless steel, aluminum, aluminum alloy, magnesium, etc., polymers such as, PEEK, porous PEEK, carbon fiber PEEK, resorbable polymers, PLLA, etc., allograft, synthetic allograft substitute, ceramics in the form of bioglass, tantalum, Nitinol, or alternative bone growth material or some composite material or combination of these materials.

The spacer portion 20-2820 may be formed of a different material than the plate portion 50-2850. For example, the plate portion 50-2850 may be formed of a metallic material such as, a titanium or a titanium alloy, and the spacer portion 20-2820 may be formed of a non-metallic material such as, a polymer such as, PEEK, an allograft, a bioresorbable material, a ceramic, etc. Alternatively, the plate portion 50-2850 and the spacer portion 20-2820 may be formed from the same material. In addition, the plate portion 50-2850 and spacer portion 20-2820 may be integrally formed, pre-assembled or separately provided to a surgeon and assembled in the operating room.

As will be appreciated by one of ordinary skill in the art, the implant 10-2800, or portions thereof, may also be coated with various compounds to increase bony on-growth or bony in-growth, to promote healing or to allow for revision of the implant 10-2800, including hydroxyapatite, titanium-nickel, vapor plasma spray deposition of titanium, or plasma treatment to make the surface hydrophilic.

Referring to FIG. 1, the intervertebral implant 10 of a first preferred embodiment includes the interbody spacer portion 20, the plate portion 50, first, second and third bone fixation elements 70 and the retention mechanism. In the first preferred embodiment, the retention mechanism is in the form of a retaining clip 80 coupled to the plate portion 50 via a blocking plate 82. Alternatively, the implant 10 may include a plurality of retaining clips 80 coupled to the plate portion 50 via the blocking plate 82. The retaining clip 80 is preferably coupled to the blocking plate 82 before the blocking plate 82 is coupled to the plate portion 50.

The blocking plate 82 preferably includes a pair of elastically deflectable spring fingers 84 extending distally therefrom for engaging corresponding recesses formed in the side surfaces 56, 58 of the plate portion 50. The blocking plate 82 preferably is sized and configured to snap over the trailing surface 62 of the plate portion 50 so that, in operation, the retaining clip 80 is coupled to the blocking plate 82 and the blocking plate 82 and the retaining clip 80 assembly is coupled to, e.g., snapped over, the trailing surface 62 of the plate portion 50. The implant 10 is then inserted into the disc space D and the bone fixation elements 70 are inserted. Alternatively, the blocking plate 82 and the retaining clip 80 assembly may be coupled to the plate portion 50 subsequent to the insertion of the bone fixation elements 70 through the boreholes 40 formed in the plate portion 50. Alternatively, a variety of other now or hereafter developed coupling mechanisms may be used for coupling the blocking plate 82 to the plate portion 50 including snap-locks, screw(s) and borehole(s), etc.

Referring to FIGS. 2A-2E, the intervertebral implant 100 of a second preferred embodiment includes the spacer portion 120, the plate portion 150, first and second bone fixation elements (not shown) and the retention mechanism. In the second preferred embodiment, the retention mechanism is in the form of an externally threaded retaining screw 180, a threaded borehole 185 formed in the plate portion 150 preferably between the bone fixation holes 40 and a blocking plate 190 for covering, contacting and/or interacting with at least a portion of the first and second bone fixation elements to block the first and second bone fixation elements and limit the first and second bone fixation elements from backing-out of the bone fixation holes 40.

The implant 100 may further include an implant inserter instrument 195 including an inner shaft 196 having a set of external threads 197 protruding from a distal end thereof for threadably engaging the threaded borehole 185 formed in the plate portion 150 of the implant 100. The implant inserter instrument 195 preferably also includes an outer tubular member 198 housed concentrically around the inner shaft 196 and configured to enable the inner shaft 196 to rotate with respect thereto.

The implant inserter instrument 195, and more particularly, the outer tubular member 198 preferably includes one or more stops 199 for preventing over-insertion of the implant 100. More preferably, the implant inserter instrument 195 includes first and second stops 199, the first stop 199 protruding superiorly for contacting the superior vertebral body V while the second stop 199 protrudes inferiorly for contacting the inferior vertebral body V. Incorporation of more or less stops 199 is envisioned. Incorporation of the first and second stops 199 facilitates fully seating the implant 100 with respect to the adjacent vertebral bodies V regardless of the irregular anatomy of a patient's spine, which often characterizes the outer surface of the vertebral bodies V.

In use, the stops 199 are configured to abut the anterior aspects of the vertebral bodies V during implantation, although the stops 199 may abut the lateral or antero-lateral aspects of the vertebral bodies V depending upon the surgical procedure and insertion path being utilized. The stops 199 assist in preventing over-insertion of the implant 100 during implantation and assist in securing the position of the implant 100 during insertion of the bone fixation elements, as will be described in greater detail below.

In operation, the implant inserter instrument 195 is coupled to the implant 100 via threadably mating the threads 197 formed on the distal end of the inner shaft 196 with the threaded borehole 185 formed in the plate portion 150. The implant inserter instrument 195 is then used to insert the implant 100 into the disc space D between the adjacent vertebral bodies V until the stops 199 abut the anterior (or lateral or antero-lateral) aspects of the vertebral bodies V. The first and second bone fixation elements are then inserted through the boreholes 40 and into the vertebral bodies V while lagging of the implant 100 is limited by interaction of the stops 199 with the anterior aspects of the vertebral bodies V. That is, advancement of the bone fixation elements into the bone fixation holes 40 causes the head portion of the bone fixation elements to contact the inner spherical portions of the bone fixation holes 40 and tends to draw the vertebral bodies V into alignment as opposed to resulting in the over-insertion of the implant 100 since the stops 199 guide the movement of the vertebral bodies V during bone fixation manipulation. That is, because the stops 199 contact the adjacent vertebral bodies V and prevents over-insertion of the implant 100 into the disc space D, advancement of the bone fixation elements tends to pull and/or reposition the adjacent vertebral bodies V together to promote fusion.

The position of the implant 100 can be adjusted with respect to the disc space D by rotating the inner shaft 196, e.g., by rotating a handle portion of the inner shaft 196. The bone fixation elements are inserted through the boreholes 40 and into the vertebral bodies V, while the implant inserter instrument 195 remains coupled to the implant 100 such that the stops 199 remain abutted to the anterior aspects of the vertebral bodies V to limit movement of the implant 100 while the bone fixation elements are being inserted. The implant inserter instrument 195 may then be decoupled from the implant 100 and the blocking plate 190 may be coupled to the plate portion 150 via the retaining screw 180 to block the bone fixation elements from backing-out.

Figure 3B:
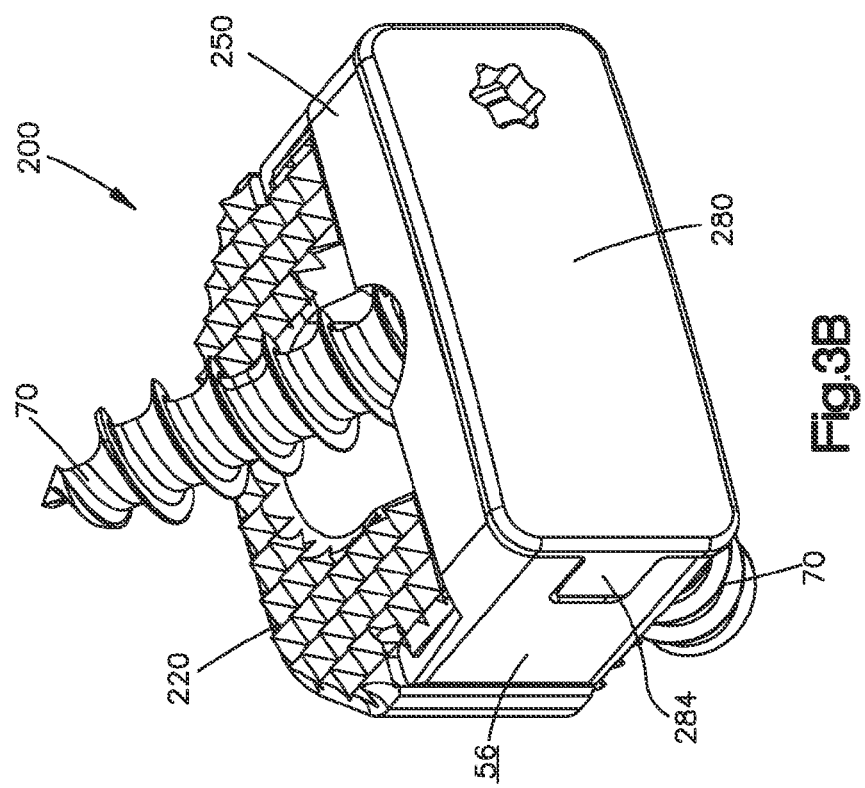
FIG. 3B illustrates an anterior perspective view of the implant of FIG. 3A with a blocking plate retention mechanism coupled thereto.
Figure 3A:
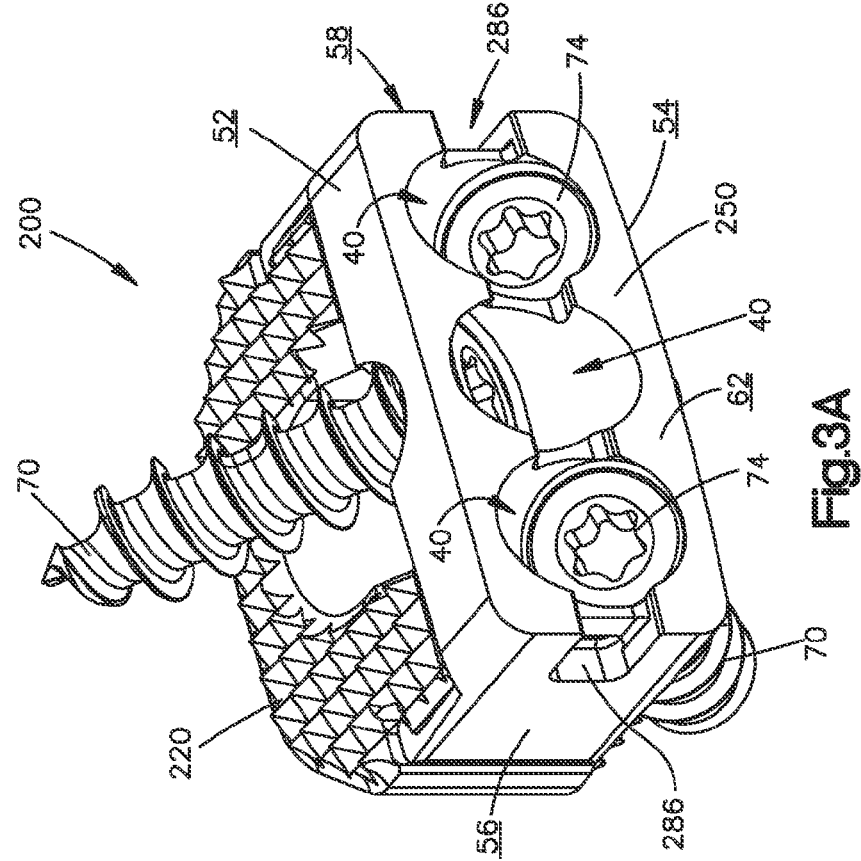
FIG. 3A illustrates an anterior perspective view of an implant according to a third preferred embodiment of the present application.

Referring to FIGS. 3A and 3B, the intervertebral implant 200 of a third preferred embodiment includes the interbody spacer portion 220, the plate portion 250, first, second and third bone fixation elements 70 and the retention mechanism. In the third preferred embodiment, the retention mechanism includes a blocking plate 280 having a pair of elastically deflectable spring fingers 284 extending distally therefrom for engaging corresponding recesses 286 formed in the side surfaces 56, 58 of the plate portion 250. The blocking plate 280 is preferably sized and configured to snap over the trailing surface 62 of the plate portion 250 so that, in operation, the blocking plate 280 may be coupled to the plate portion 250 subsequent to the insertion of the bone fixation elements 70 to limit back-out of the bone fixation elements 70.

Referring to FIGS. 4A and 4B, the intervertebral implant 300 of a fourth preferred embodiment includes the interbody spacer portion 320, the plate portion 350, first, second and third bone fixation elements 70 and the retention mechanism. In the fourth preferred embodiment, the retention mechanism includes a blocking plate 380 having a plurality of elastically deflectable spring fingers 384 extending distally therefrom for engaging corresponding recesses or indentations 386 formed in the plate portion 350. More preferably, the recesses or indentations 386 are formed within the bone fixation holes 40 formed in the plate portion 350. The blocking plate 380 is sized and configured to snap onto the trailing surface 62 of the plate portion 350 so that, in operation, the blocking plate 380 is operatively coupled to the plate portion 350 subsequent to the insertion of the bone fixation elements 70 to limit back-out of the bone fixation elements 70.

It should be understood that additional blocking plate geometries and securing mechanisms are envisioned. For example, referring to FIGS. 5A-5D, a variety of additional blocking plate geometries and securing mechanisms 380', 380", 380''', 380'''' are provided for use with the preferred implant assemblies and their configuration and operation will be apparent to one having ordinary skill in the art from the above-listed descriptions of the implants, assemblies and blocking plates. The additional blocking plate configurations may be constructed of rigid or flexible materials and may be coupled to the plate portions before or after insertion of the bone fixation elements.

Figure 6A:
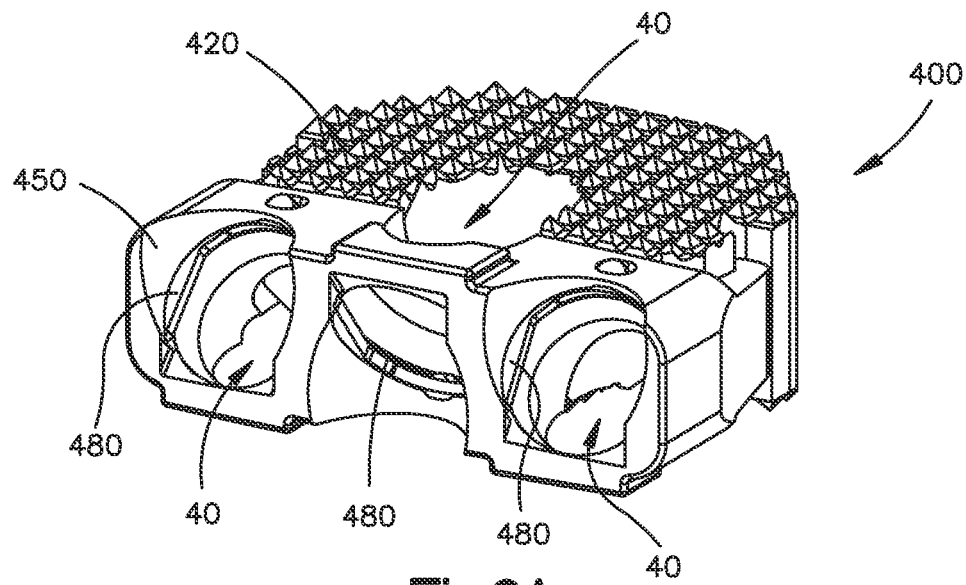
FIG. 6A illustrates an anterior perspective view of an implant according to a fifth preferred embodiment of the present application.
Figure 6B:
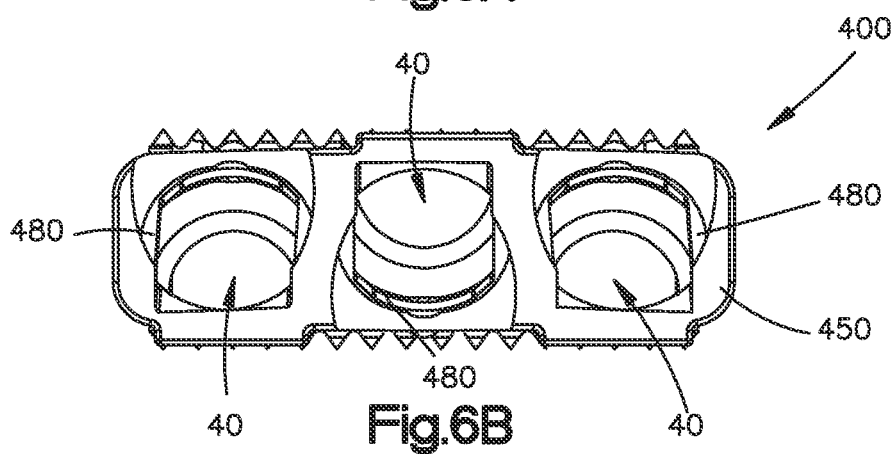
FIG. 6B illustrates an anterior elevational view of the implant of FIG. 6A.
Figure 6C:
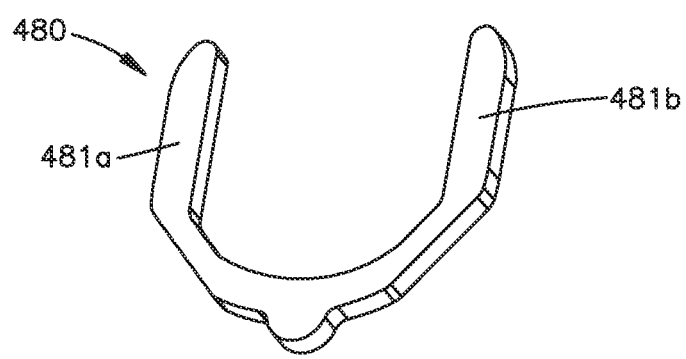
FIG. 6C illustrates a perspective view of the retention mechanism of the implant of FIG. 6A.

Referring to FIGS. 6A-6C, the intervertebral implant 400 of a fifth preferred embodiment includes the interbody spacer portion 420, the plate portion 450, first, second and third bone fixation holes 40 for receiving first, second and third bone fixation elements (not shown) and the retention mechanism. In the fifth preferred embodiment, the retention mechanism includes first, second and third unidirectional retaining clips 480 positioned inside the first, second and third bone fixation holes 40. The retaining clips 480 are preferably in the form of a wishbone clip formed of, for example, elgiloy, although other shapes and material are envisioned. The retaining clips 480 are mounted in the bone fixation holes 40 to assist in securing the bone fixation elements to the plate portion 450 by allowing insertion of the bone fixation elements into the holes 40 while preventing the bone fixation elements from backing-out of the holes 40. That is, the retaining clips 480 preferably permit unidirectional advancement of the head portion of the bone fixation elements distally into the bone fixation holes 40 and through the retaining clip 480 while limiting backing-out of the bone fixation elements by blocking its regression once the head portion has passed through the retaining clip 480.

In operation, the partially spherical head portion of the bone fixation elements passes distally into the bone fixation holes 40 and through the retaining clip 480 such that the tapered or partially spherical underside of the head portion of the bone fixation elements bear against the retaining clips 480 thereby urging the arms 481a, 481b of the retaining clips 480 to flex outwardly a slight amount to permit passage of the head portion therethrough.

Once the head portion of the bone fixation element has fully passed through the retaining clip 480, the arms 481a, 481b of the retaining clip 480 spring back to their original configuration, thereby covering and/or blocking the head portion of the bone fixation element. The bone fixation element is thereby prevented from backing-out due to the non-tapered (partially flat) aspect of the proximal surface of the head portion of the bone fixation element, which generally prevents the bone fixation element from passing back through the retaining clip 480. The retaining clip 480 may be manually flexed open by a tool to permit removal of the bone fixation elements from the implant 400, if desired.

Alternatively, the retention mechanism may take on any other form that facilitates unidirectional advancement of the bone fixation elements while limiting backing-out of the bone fixation elements. For example, the retention mechanism may be in the form of a blocking mechanism. For example, the plate portion 450 may be formed from a polymer such as PEEK and the retention mechanism may include one or more blocking mechanisms formed from a metal such as titanium. In use, the blocking mechanism is preferably disposed within the bone fixation hole 40 formed in the plate portion 450 and is configured in such a way as to enable deformation of the blocking mechanism to allow the head portion of the bone fixation element to pass beyond the blocking mechanism. Once the head portion of the bone fixation element passes beyond the blocking mechanism, the blocking mechanism elastically return to its original shape to block and/or cover the head portion of the bone fixation element from backing-out from the plate portion 450. The polymeric plate portion 450 can be injection molded onto or around the blocking mechanism(s). The blocking mechanism can be any one of a number of configurations so long as the blocking mechanism deforms to enable the bone fixation element to pass therethrough and then radially expands to block and/or cover at least a portion of the bone fixation element. The blocking mechanism can be configured to block and/or cover a single bone fixation element or a plurality of bone fixation elements.

Referring to FIG. 7, the intervertebral implant 500 of a sixth preferred embodiment includes the interbody spacer portion 520, the plate portion 550, first and second bone fixation elements 70 and the retention mechanism. In the sixth preferred embodiment, the retention mechanism includes an unidirectional retaining clip 580 disposed in a recess 582, such as a blind borehole, formed in the plate portion 550 between the bone fixation holes 40. In use, a portion of the retaining clip 580 protrudes from the recess 582 into each of the bone fixation holes 40 to cover and/or block the head portions 74 of the bone fixation elements 70 in an implanted position. The retaining clip 580 preferably permits unidirectional advancement of the head portions 74 of the first and second bone fixation elements 70 distally into the bone fixation holes 40 and past the retaining clip 580 to limit backing-out of the bone fixation elements 70 by covering and/or blocking their regression once the head portions 74 of the bone fixation elements 70 have advanced past the retaining clip 580. The retaining clip 580 is otherwise substantially identical in operation to the retaining clip 480 discussed above.

It should be noted that while the retaining clip 580 is shown as having an S-shape on its side and retaining clip 480 is shown as having a wishbone shape, it is envisioned that a range of applicable geometries can be used. For example, retaining clip 580 may have a wishbone shape wherein a portion of each arm protrudes into each bone fixation hole 40. Accordingly, the retaining clips 480, 580 may have nearly any shape and/or configuration that permits engagement with the plate portion 450, 550, flexure out of the bone fixation holes 40 as the head portion 74 of the bone fixation elements 70 passes therethrough and spring back at least partially into the bone fixation holes 40 once the head portion 74 passes the retaining clip 480, 580.

Referring to FIG. 7, the implant 500, and any other implant 10-2800 described herein, may also incorporate one or more stops 99 that are preferably integrally formed on the plate portion 550. The stops 99 are configured to abut the anterior (or lateral or antero-lateral) aspects of the vertebral bodies V during implantation. In operation, the stops 99 assist in preventing over-insertion of the implant 500 during insertion into the disc space D and assist in securing the position of the implant 500 during insertion of the bone fixation elements 70.

As shown in FIG. 7, the implant 500 may include first and second stops 99a, 99b. Incorporation of first and second stops 99a, 99b is desirable in circumstances where it is difficult to fully seat the implant 500 due to an irregular anatomy of the patient's spine, which often characterizes the anterior (or lateral or antero-lateral) aspects of the vertebral bodies V. Due to the disposition of the stops 99, the implant 500 generally has a zero-profile external to the disc space D at least along a cranial-caudal midline, because the trailing surface 62 of the plate portion 550 can be designed to be convex to match the disc space D. The distal surfaces of the stops 99 can be configured to embed at least partially into the vertebral bodies V during impaction to further reduce the profile of the plate portion 550 exterior to the disc space D, if so desired. For example, the distal surface of the stops 99 may include one or more pyramid shaped projections, teeth, blades, etc. extending therefrom for embedding at least partially into the vertebral bodies V during impaction. Alternatively, as shown in FIG. 8, the implant may include four stops 99a-99d disposed at or near the four corners of the plate portion. It is envisioned that the implant may include any number of stops 99 in any configuration.

Figure 9A:
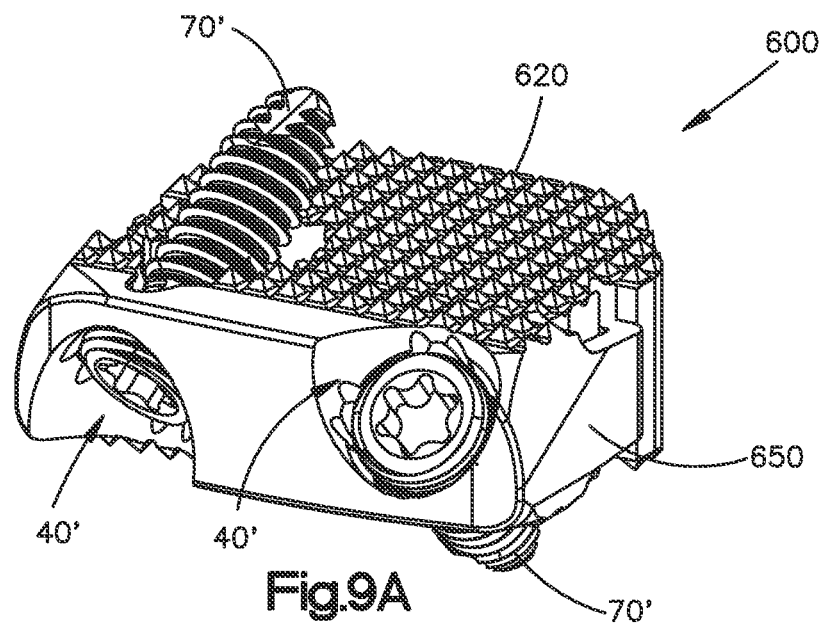
FIG. 9A illustrates an anterior perspective view of an implant according to a seventh preferred embodiment of the present application.
Figure 9B:
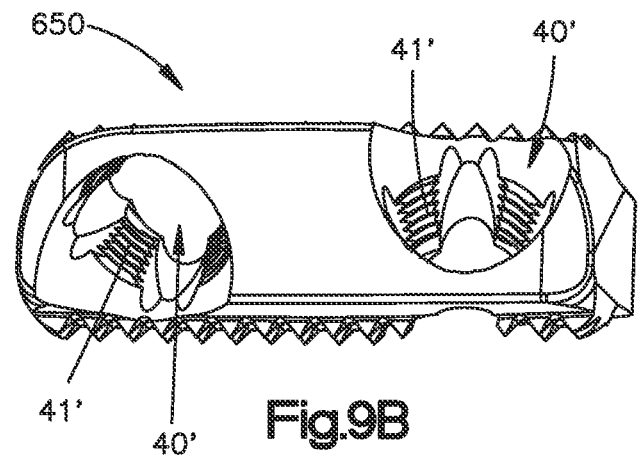
FIG. 9B illustrates an anterior elevational view of the plate portion of the implant of FIG. 9A.
Figure 9C:
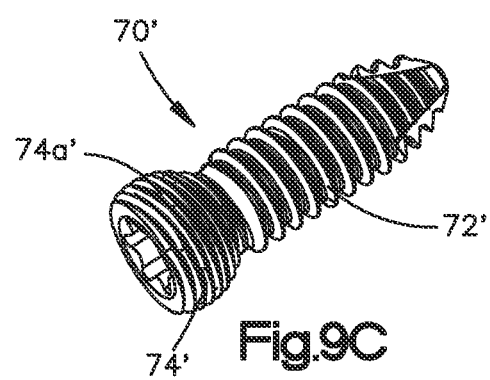
FIG. 9C illustrates a side elevational view of the bone fixation element of the implant of FIG. 9A.

Referring to FIGS. 9A-9C, the intervertebral implant 600 of a seventh preferred embodiment includes the interbody spacer portion 620, the plate portion 650, first and second bone fixation elements 70' and the retention mechanism. In the seventh preferred embodiment, the retention mechanism includes forming scallop-shaped threaded regions 41' on the inner surface of the bone fixation holes 40' for engaging external threads 74a' formed on the head portions 74' of the bone fixation elements 70'. In operation, the partially threaded scallop-shaped bone fixation holes 40' mate with the exterior threading 74a' formed on the head portions 74' of the bone fixation elements 70' to permit variable angle orientation of the bone fixation elements 70' with respect to the plate portion 650 as well as provide an interference fit between the head portions 74' of the bone fixation elements 70' and the interior of the bone fixation holes 40' to reduce the likelihood of backing-out. The geometry of the bone fixation holes 40' further enable a variety of different screw sizes and styles (variable angle screws, locking screws, locking variable angle screws, etc.) to be utilized in conjunction with the implant 600.

Figure 10:
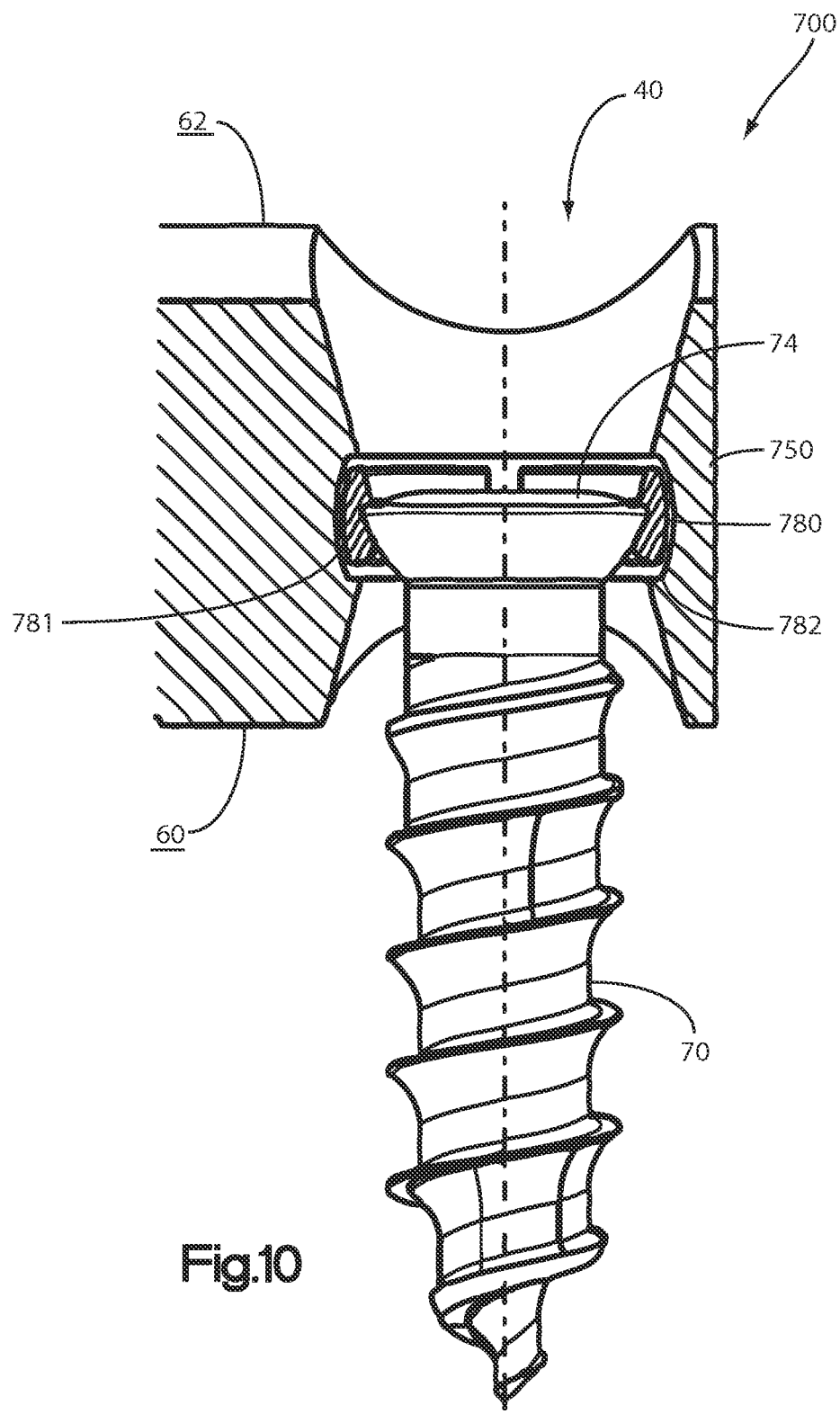
FIG. 10 illustrates a partial cross-sectional view of a plate portion, a bone fixation element and a retention mechanism of an implant according to an eighth preferred embodiment of the present invention.

Referring to FIG. 10, the intervertebral implant 700 of an eighth preferred embodiment includes the interbody spacer portion (not shown), the plate portion 750, a plurality of bone fixation elements 70 and the retention mechanism. In the eighth preferred embodiment, the retention mechanism includes a bushing 780 located within the bone fixation holes 40. More preferably, the bushing 780 is spring-loaded inside the bone fixation holes 40 formed in the plate portion 750. The bone fixation holes 40 preferably include an undercut or groove 782 for receiving and/or securing the bushing 780 therein. In use, the head portion 74 of the bone fixation element 70 bears against the bushing 780 during insertion of the bone fixation element 70, causing the bushing 780 to initially expand and then subsequently to collapse about the head portion 74 to thereby secure the bone fixation element 70 to the plate portion 750. The bushing 780 preferably includes a spherical or curvate outer surface 781 for mating with a corresponding spherical or curvate inner surface formed in the undercut or groove 782 so that the bushing 780, and hence the bone fixation element 70, can polyaxial rotate with respect to the plate portion 750.

Figure 11:
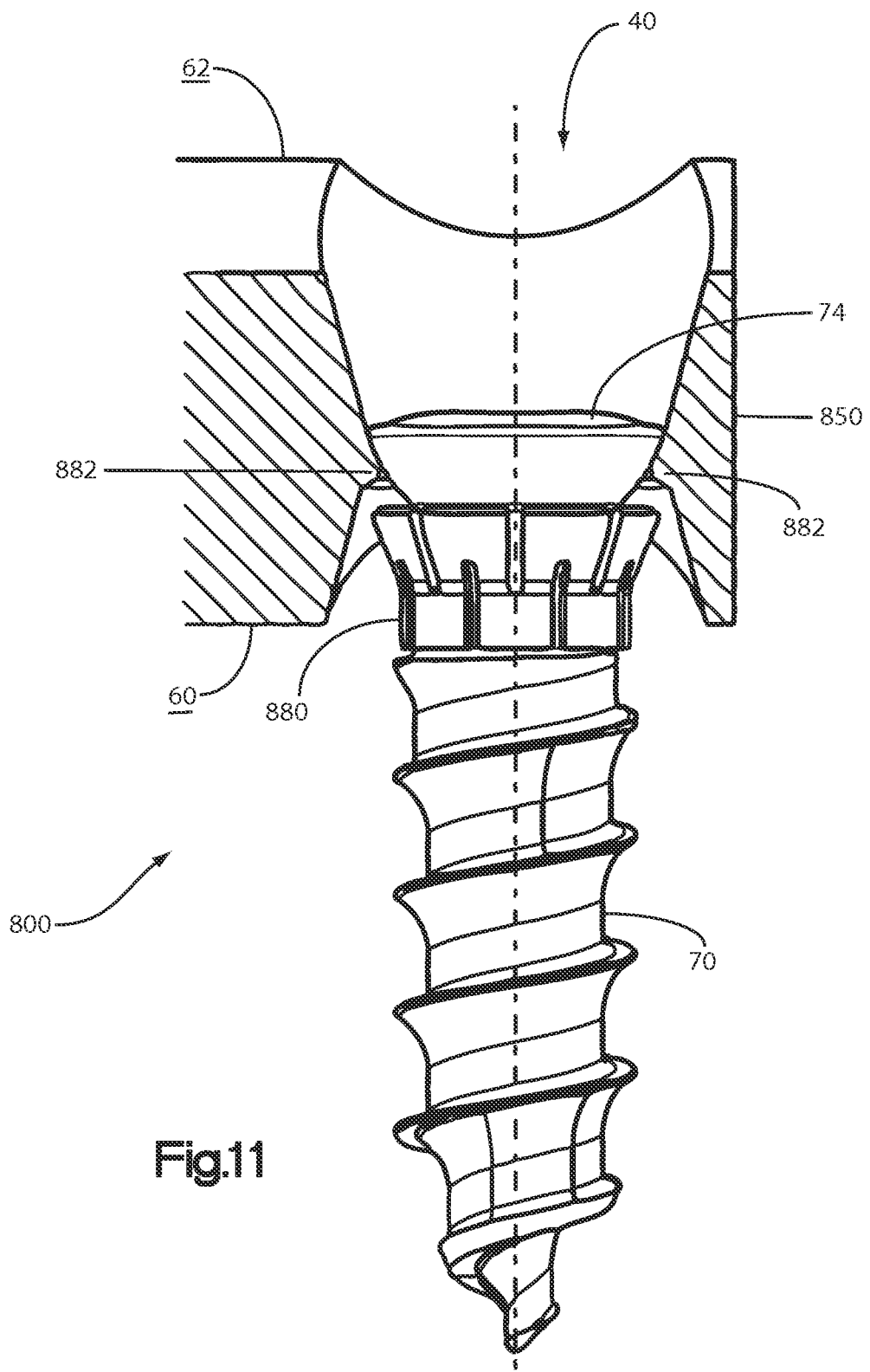
FIG. 11 illustrates a partial cross-sectional view of a plate portion, a bone fixation element and a retention mechanism of an implant according to a ninth preferred embodiment of the present invention.

Referring to FIG. 11, the intervertebral implant 800 of a ninth preferred embodiment includes the interbody spacer portion (not shown), the plate portion 850, a plurality of bone fixation elements 70 and the retention mechanism. In the ninth preferred embodiment, the retention mechanism includes a bushing 880 circumferentially disposed around the head portion 74 or neck portion of the bone fixation element 70. More preferably, the bushing 880 is spring-loaded around the head portion 74 or neck portion of the bone fixation element 70. The bone fixation hole 40 formed in the plate portion 850 preferably includes one or more projections 882 protruding therein so that, as the bushing 880 and bone fixation element 70 are advanced into the bone fixation hole 40, the bushing 880 interacts with the one or more projections 882 to compress the bushing 880. Upon passing the projections 882, the bushing 880 radially expands such that the diameter of the bushing 880 is larger than the diameter of the bone fixation hole 40 as measured at the projections 882 thereby limiting back-out of the bone fixation element 70.

Figure 12:
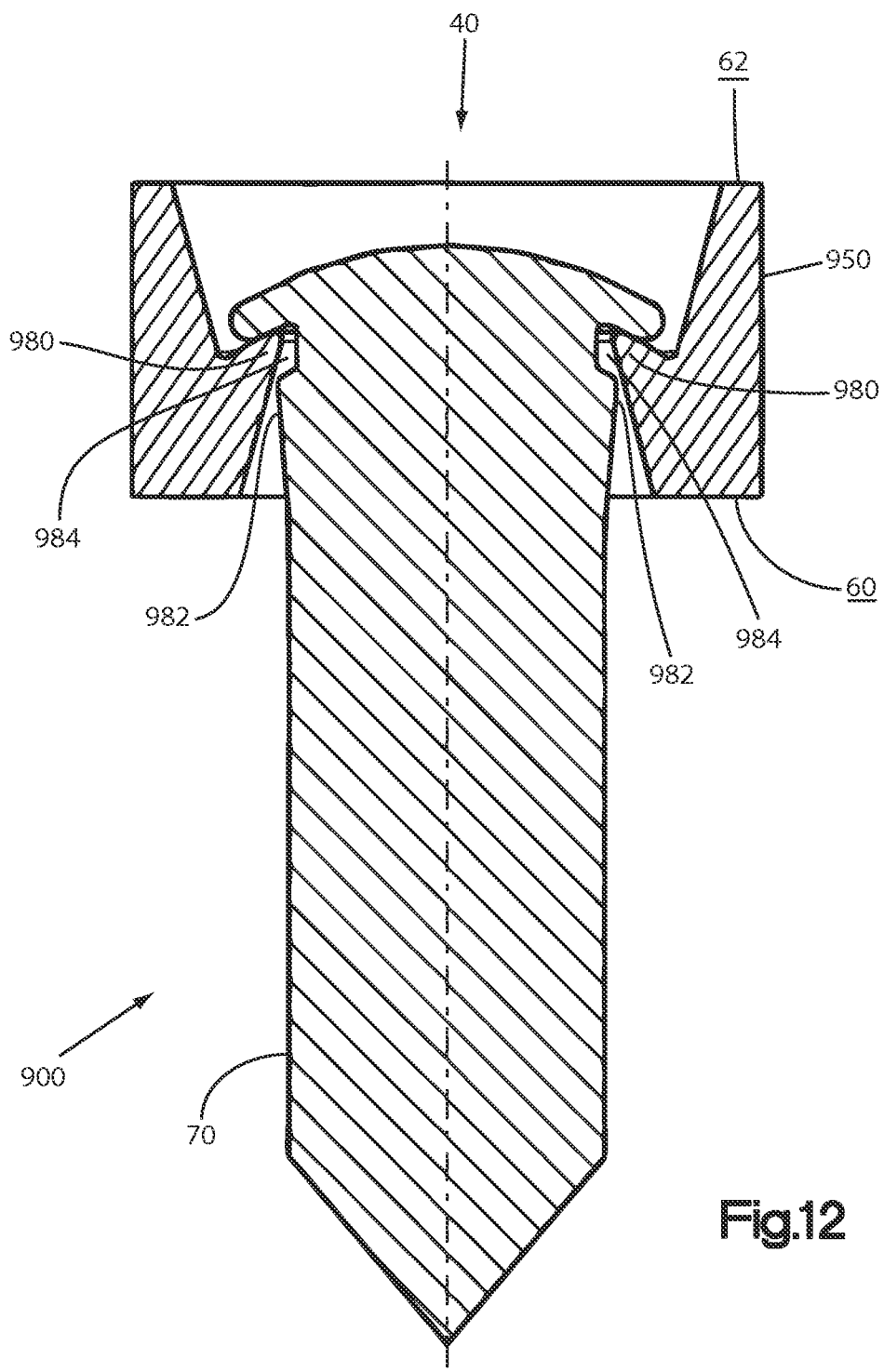
FIG. 12 illustrates a partial cross-sectional view of a plate portion, a bone fixation element and a retention mechanism of an implant according to a tenth preferred embodiment of the present invention.

Referring to FIG. 12, the intervertebral implant 900 of a tenth preferred embodiment includes the interbody spacer portion (not shown), the plate portion 950, a plurality of bone fixation elements 70 and the retention mechanism. In the tenth preferred embodiment, the retention mechanism includes one or more thin-walled projections 980 protruding into the bone fixation holes 40. The projections 980 being configured to deform as the bone fixation element 70 is advanced through the bone fixation hole 40. The bone fixation elements 70 preferably including a tapered flange 982 and a recess 984 formed on the head portion 74 or neck portion thereof. The flange 982 being configured to expand the projection 980 as the bone fixation element 70 is advanced through the bone fixation hole 40. Once the bone fixation element 70 is fully seated, the projection 980 contracts and is received within the recess 984 to thereby secure the bone fixation element 70 with respect to the plate portion 950.

Referring to FIG. 13, the intervertebral implant 1000 of an eleventh preferred embodiment includes the interbody spacer portion 1020, the plate portion 1050, first and second bone fixation elements 70 and the retention mechanism. In the eleventh preferred embodiment, the retention mechanism includes a plurality of deformable fingers, projections or thinned-walled lip members (collectively "fingers") 1080 that are preferably machined into the plate portion 1050 circumferentially about the bone fixation holes 40. Once the bone fixation element 70 is inserted through the bone fixation hole 40, a forceps-like instrument 1090 may be used to deform the plurality of fingers 1080 to at least partially cover and/or block the head portion 74 of the bone fixation element 70. The fingers 1080 may be machined to stand proud or lie flush with respect to the trailing surface 62 of the plate portion 1050 prior to deformation.

Referring to FIGS. 14A and 14B, the intervertebral implant 1100 of a twelfth preferred embodiment includes the interbody spacer portion (not shown), the plate portion 1150, a plurality of bone fixation elements 70 and the retention mechanism. In the twelfth preferred embodiment, the retention mechanism includes a spring clip 1180. The clip 1180 is preferably manufactured from an elastically deformable material so that the clip 1180 may be deformed to a reduced configuration. In use, the bone fixation element 70 is inserted into a bone fixation hole 40 formed in the plate portion 1150. The clip 1180 is then preferably deformed via a grasping or forceps-type instrument 1190 to the reduced configuration. After the bone fixation element 70 has been fully inserted, the instrument 1190 places the clip 1180 into the interior of the bone fixation hole 40 or a groove (not shown) formed on the trailing surface 62 of the plate portion 1150, and releases the spring clip 1180, at which point the spring clip 1180 expands and returns to its original shape, thereby locking to the groove or hole 40 and covering and/or blocking the head portion 74 of the bone fixation element 70.

Referring to FIG. 15, the intervertebral implant 1200 of a thirteenth preferred embodiment includes the interbody spacer portion (not shown), the plate portion 1250, a plurality of bone fixation elements 70" and the retention mechanism. In the thirteenth preferred embodiment, the bone fixation elements 70" are in the form of an expansion-headed screw and the retention mechanism includes a locking screw 1280 couplable to and advanceable within the expansion-head screw 70". That is, the head portion 74" of the expansion-head screw 70" preferably includes an internally threaded bore 1281 and optional slots (not shown) extending from a proximal end thereof. In use, the locking screw 1280 is actuated, e.g., rotated, into engagement with the internally threaded bore 1281 formed in the proximal end of the expansion-head screw 70" to radially expand the head portion 74" of the expansion-head screw 70" to thereby lock the expansion-head screw 70" within the bone fixation hole 40. The head portion 74" may include a partially spherical outer surface for mating with a corresponding partially spherical inner surface formed in the bone fixation hole 40 to enable variable angular placement of the expansion-head screw 70" with respect to the plate portion 1250", as well as angulation of the screw shaft 72" with respect to the plate portion 1250 after the screw 70" is locked to the plate portion 1250. The spherical dimensions of the head portion 74" of the expansion-head screw 70" can be chosen to allow an interference or rigid fit or to allow for a clearance or toggling fit between the expansion-head screw 70" and the plate portion 1250.

Many varieties of blocking plates are used in the art to limit back-out of bone fixation elements 70. Most of these blocking plates utilize an additional screw, rivet, or pin to secure the blocking plate in place. Referring to FIGS. 16A and 16B, the intervertebral implant of a fourteenth preferred embodiment includes the interbody spacer portion (not shown), the plate portion (not shown), a plurality of bone fixation elements (not shown) and the retention mechanism. In the fourteenth preferred embodiment, the retention mechanism includes a blocking plate 1380 formed from an elastic "spring-like" material that preferably enables the plate 1380 to be manufactured in a biased position. For example, the blocking plate 1380 may include a concave or convex trailing surface 1382 (as shown in FIG. 17A) that can be snapped or popped in the opposite direction by pushing on a center portion 1384 of the blocking plate 1380. This snapping movement forces the outside edges of the blocking plate 1380 to move inwardly or outwardly to increase or decrease the radius of the blocking plate 1380. The outside edges of the blocking plate 1380 can include fingers 1386 that are mateable with recesses (not shown) formed on the plate portion (not shown) such that a secure attachment between the blocking plate 1380 and the plate portion is achieved without the inclusion of additional components. Referring to FIG. 17B, applying a force to the center portion 1384 of the blocking plate 1380, when placed appropriately with respect to the plate portion, forces the blocking plate 1380 to pop inside out, increasing its radius and mating to the plate portion to at least partially cover the head portions 74 of the bone fixation elements 70.

Figure 17:
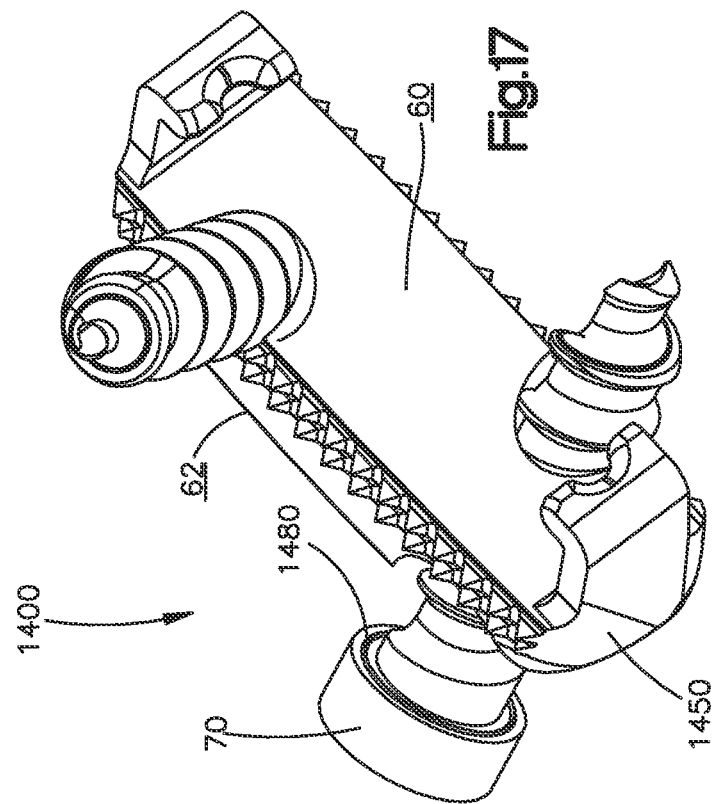
FIG. 17 illustrates a partial perspective view of a plate portion, a bone fixation element and a retention mechanism of an implant according to a fifteenth preferred embodiment of the present invention.

Referring to FIG. 17, the intervertebral implant 1400 of a fifteenth preferred embodiment includes the interbody spacer portion (not shown), the plate portion 1450, a plurality of bone fixation elements 70 and the retention mechanism. In the fifteenth preferred embodiment, the plate portion 1450 and the bone fixation elements 70 are manufactured from a polymer, such as PEEK, so that a welding process can be utilized to secure the bone fixation elements 70 to the plate portion 1450. That is, for example, the implant 1400 may include a ring 1480 or other protrusion inherent on the underside of the head portion 74 of the bone fixation elements 70. The plate portion 1450, the bone fixation elements 70 and the ring 1480 each being manufactured from PEEK or similar polymer. The ring 1480 creates a small surface area for heat or vibration to be transferred therethrough. In use, after the bone fixation elements 70 have been inserted through the plate portion 1450, an ultrasonic vibration or heat is applied to the head portion 74 of the bone fixation element 70 to thereby cause the ring 1480 and its interface with the plate portion 1450 to melt and fuse together, thereby locking the bone fixation element 70 to the plate portion 1450. The cross-sectional area of the ring 1480 adjacent to the plate portion 1450 is preferably relatively small to focus the vibrations and/or heat in these areas and to promote fusing of the ring 1480 to the plate portion 1450. Alternatively, the bone fixation element 70 can be a non-threaded pin so that the ultrasonic vibrations can be utilized to drive the pins into the bone before welding.

Figure 18:
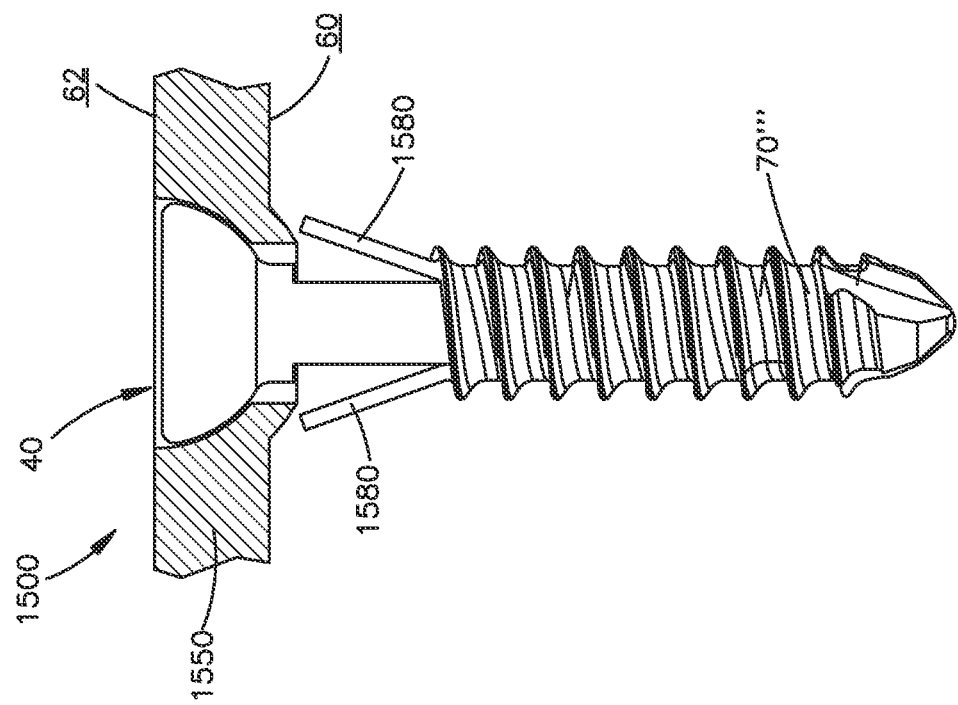
FIG. 18 illustrates a partial cross-sectional view of a plate portion, a bone fixation element and a retention mechanism of an implant according to a sixteenth preferred embodiment of the present invention.

The most common bone fixation element for securing an implant to bone is a bone screw, as is apparent to one having ordinary skill in the art. The threads on the shaft of the bone screw provide purchase, which allows lagging and fixation. The bone screw is preferably threaded into the bone by torquing the head of the bone screw. This method of fixation may be altered by eliminating the threading step and saving surgical time and effort. For example, referring to FIG. 18, the intervertebral implant 1500 of a sixteenth preferred embodiment includes the interbody spacer portion (not shown), the plate portion 1550, a plurality of bone fixation elements 70''' and the retention mechanism. In the sixteenth preferred embodiment, the bone fixation elements 70''' are in the form of non-threaded pins that include one or more projections 1580 extending from the neck or shaft portion of the pin 70'''. The projections 1580 preferably are biased to outwardly extend from the neck or shaft portion of the pin 70'''. The projections 1580 are preferably inwardly deflectable so that the projections 1580 can be advanced through the bone fixation holes 40 formed in the plate portion 1550. In use, once the non-threaded pins 70''' have been fully inserted, the projections 1580 expand. The outward expansion of the projections 1580 occurs interior to the bone and/or adjacent to the leading surface 60 of the plate portion 1550 adjacent to the bone fixation hole 40 to secure the pin 70''' into the bone and/or block the pin 70''' from backing-out of the plate portion 1550.

Referring to FIGS. 19A and 19B, the intervertebral implant 1600 of a seventeenth preferred embodiment includes the interbody spacer portion (not shown), the plate portion 1650, a plurality of bone fixation elements 70'''' and the retention mechanism. In the seventeenth preferred embodiment, the bone fixation elements 70'''' include a cannulated bore 1680 extending from a proximal end thereof. An instrument or mandrel 1682 is also provided for insertion into the cannulated bore 1680. In use, insertion of the mandrel or instrument 1682 into the cannulated bore 1680 expands one or more fingers or other expandable members 1684 on the shaft or neck portion of the bone fixation element 70''''. Alternatively, insertion of the mandrel or instrument 1682 into the cannulated bore 1680 creates a bulge 1686 along the shaft or near the neck of the bone fixation element 70''''. Alternatively, referring to FIG. 19C, the bone fixation elements 70'''' may be inserted into the patient's bone with the instrument or mandrel 1682 pre-inserted into the cannulated bore 1680. The instrument or mandrel 1682 including an enlarged distal end 1682a so that, in use, removal of the mandrel or instrument 1682 from the cannulated bore 1680 expands one or more fingers or other expandable members 1684 or creates a bulge 1686 along the shaft or near the neck of the bone fixation element 70''''. Alternatively, the bone fixation element 70''' can be configured so that insertion of the mandrel or instrument 1682 expands a distal end of the bone fixation element 70'''', as shown in FIG. 19D.

Referring to FIGS. 20A-20C, the intervertebral implant 1700 of an eighteenth preferred embodiment includes the interbody spacer portion (not shown), the plate portion 1750 and first and second bone fixation elements 70. In the eighteenth preferred embodiment, the trajectories of the bone fixation holes 40 formed in the plate portion 1750, and hence the trajectories of the first and second bone fixation elements 70, are configured so that the head portion 74 of the first bone fixation element 70 is blocked or covered by the head portion 74 of the second bone fixation element 70. Such a configuration limits the need to include additional retention mechanisms. Similarly, as shown in FIG. 20C, a third bone fixation element 70 can be utilized in a similar arrangement to at least partially cover the head portions 74 of the first and second bone fixation elements 70.

Referring to FIG. 21, the intervertebral implant 1800 of a nineteenth preferred embodiment includes the interbody spacer portion (not shown), the plate portion 1850, a plurality of bone fixation elements 70 and the retention mechanism. In the nineteenth preferred embodiment, the head portion 74 of the bone fixation element 70 is preferably at least partially spherical and the bone fixation hole 40 formed in the plate portion 1850 is at least partially spherical. The maximum diameter of the head portion 74 is slightly larger than the entry diameter of the bone fixation hole 40. An interior diameter of the bone fixation hole 40 is enlarged so that the interior diameter of the hole 40 accommodates the head portion 74 of the bone fixation element 70. As the bone fixation element 70 is inserted into the bone fixation hole 40, the spherical head portion 74 of the bone fixation element 70 snaps into the bone fixation hole 40 where it is polyaxially captured due to the maximum spherical diameter of the head portion 74 being larger than the entry diameter of the bone fixation hole 40.

Referring to FIG. 22, the intervertebral implant 1900 of a twentieth preferred embodiment includes the interbody spacer portion (not shown), the plate portion 1950, a plurality of bone fixation elements 70 and the retention mechanism. In the twentieth preferred embodiment, the bone fixation element 70 includes a cannulated bore 71 extending from a proximal end to an distal end of the bone fixation element 70 and one or more fenestrations 71a connecting the cannulated bore 71 to the exterior surface of the shaft portion 72 of the bone fixation element 70. In use, the bone fixation element 70 is inserted through the plate portion 1950 and into the patient's bone. Bone cement 1980 is then injected into the cannulated bore 71. The bone cement 1980 travels through the cannulated bore 71 and the fenestrations 71a and into the bone surrounding the shaft portion 72 of the bone fixation element 70. Upon curing, the bone cement 1980 secures the bone fixation elements 70 with respect to the bone. The fenestrations 71a may also be configured to direct cement outflow adjacent to the leading surface 60 of the plate portion 1950 to assist in securing the plate portion 1950 to the bone.

Alternatively, referring to FIG. 22A, a filament 1982 may be used in place of the bone cement 1980. In use, the filament 1982 is fed through the cannulated bore 71 after the bone fixation element 70 has been inserted into the patient's bone. The filament 1982 preferably is sized and configured to unwind after it is fed through the cannulated bore 71. The natural shape of the filament 1982 can be bent, spiral, or random, and an instrument can be used to unwind or straighten the filament 1982 as it is being fed through the cannulated bore 71. Once the filament 1982 is displaced out of the distal end of the bone fixation element 70, the filament 1982 returns to its original shape and forms a bulk of material 1984 which serves to enhance the anchoring of the bone fixation element 70 to the bone and a position of the cannulated bone fixation element 70 relative to the plate portion 1950.

Referring to FIGS. 23A and 23B, the intervertebral implant 2000 of a twenty-first preferred embodiment includes the interbody spacer portion (not shown), the plate portion (not shown), a plurality of bone fixation elements 70 and the retention mechanism. In the twenty-first preferred embodiment, the bone fixation element 70 includes a cannulated bore 71 and is configured to be at least partially flexible. The bone fixation element 70 can be manufactured from a shape memory alloy so that the shaft 72 assumes a geometry having at least one or more bends along its longitudinal axis. A mandrel 2080 is inserted into the cannulated bore 72. The mandrel 2080 serves to straighten the shaft 72 of the bone fixation element 70 so that the bone fixation element 70 can be inserted into the bone fixation hole formed in the plate portion and into the patient's bone (as shown in FIG. 23A). Thereafter, the mandrel 2080 is removed resulting in the bone fixation element 70 returning to its original, bent geometry, which acts to prevent the bone fixation element 70 from backing away from the bone and/or plate portion (as shown in FIG. 23B).

Figure 24A:
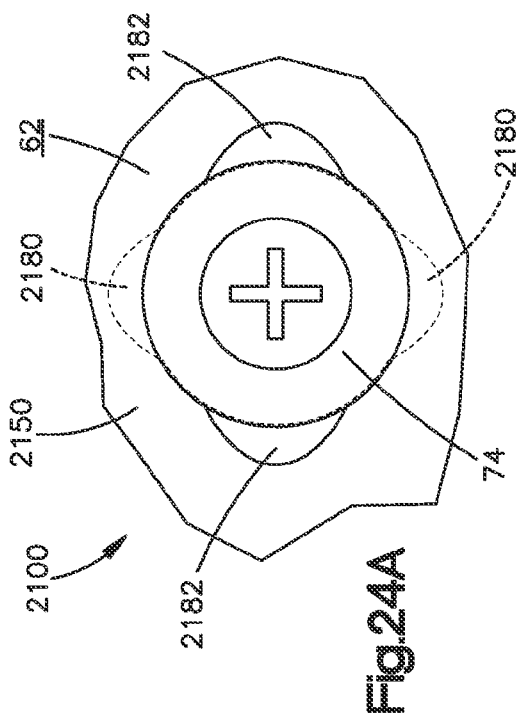
FIG. 24A illustrates a partial anterior view of a plate portion, a bone fixation element and a retention mechanism of an implant according to a twenty-second preferred embodiment of the present invention, the bone fixation element and retention mechanism being illustrated in a first insertion configuration.
Figure 24B:
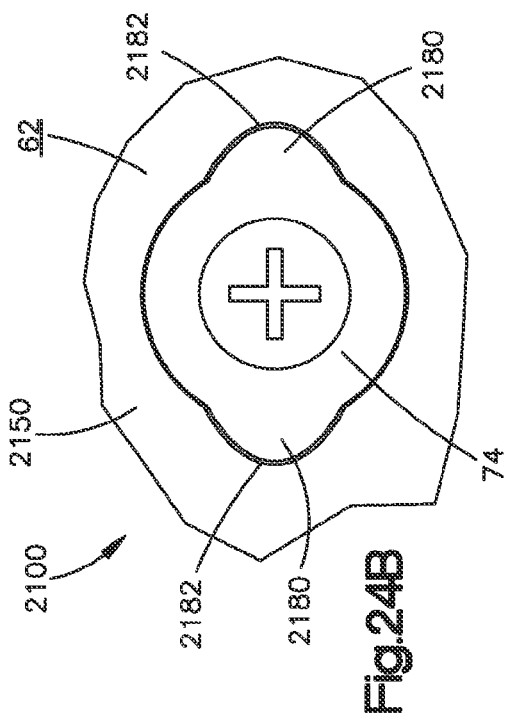
FIG. 24B illustrates a partial anterior view of the bone fixation element and retention mechanism of FIG. 24A, the bone fixation element being illustrated in a second inserted configuration.

Referring to FIGS. 24A and 24B, the intervertebral implant 2100 of a twenty-second preferred embodiment includes the interbody spacer portion (not shown), the plate portion 2150, a plurality of bone fixation elements 70 and the retention mechanism. In the twenty-second preferred embodiment, the retention mechanism includes an eccentric ring 2180 that is rotatably coupled to the head portion 74 of the bone fixation element 70. In use, the bone fixation element 70 is inserted into the bone fixation hole formed in the plate portion 2150 and into the patient's bone. Thereafter, the eccentric ring 2180 is rotated, e.g. 90 degrees, into a mating slot 2182 formed in the plate portion 2150 to block the head portion 74 of the bone fixation element 70.

Figure 25A:
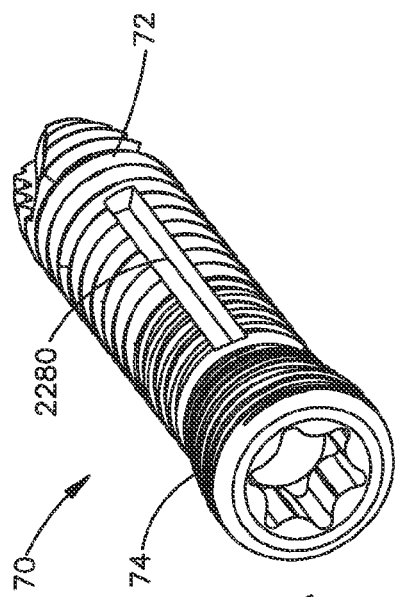
FIGS. 25A-25C illustrate various views of a bone fixation element and a retention mechanism of an implant according to a twenty-third preferred embodiment of the present invention.
Figure 25B:
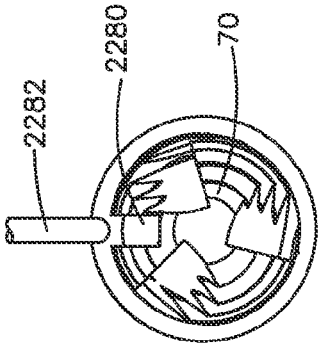
Figure 25C:
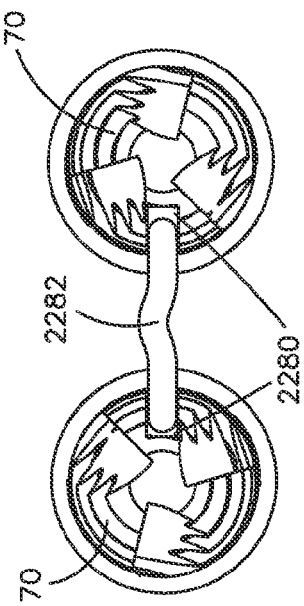

Referring to FIGS. 25A-25C, the intervertebral implant of a twenty-third preferred embodiment includes the interbody spacer portion (not shown), the plate portion (not shown) and a plurality of bone fixation elements 70. In the twenty-third preferred embodiment, the bone fixation elements 70 include one or more radial slots 2280 formed in the shaft 72 thereof. The plate portion includes an internal spring-loaded pin or spring tab 2282 that protrudes at least partially into the bone fixation holes 40. In use, advancement of the bone fixation elements 70 into the bone fixation holes 40 causes the spring-loaded tab 2282 to retract into an interior bore formed in the plate portion until the bone fixation element 70 is advanced a desirable amount with respect to the plate portion, at which point the spring-loaded tab 2282 expands into the bone fixation hole and engages the slot 2280 formed in the shaft portion 72 of the bone fixation element 70 to lock the bone fixation element 70 to the plate portion. The spring-loaded tab 2282 can extend along the interior of the plate portion and may be configured to protrude into a plurality of bone fixation holes so as to lock a plurality of bone fixation elements 70 simultaneously, as schematically represented in FIG. 25C.

Figure 26:
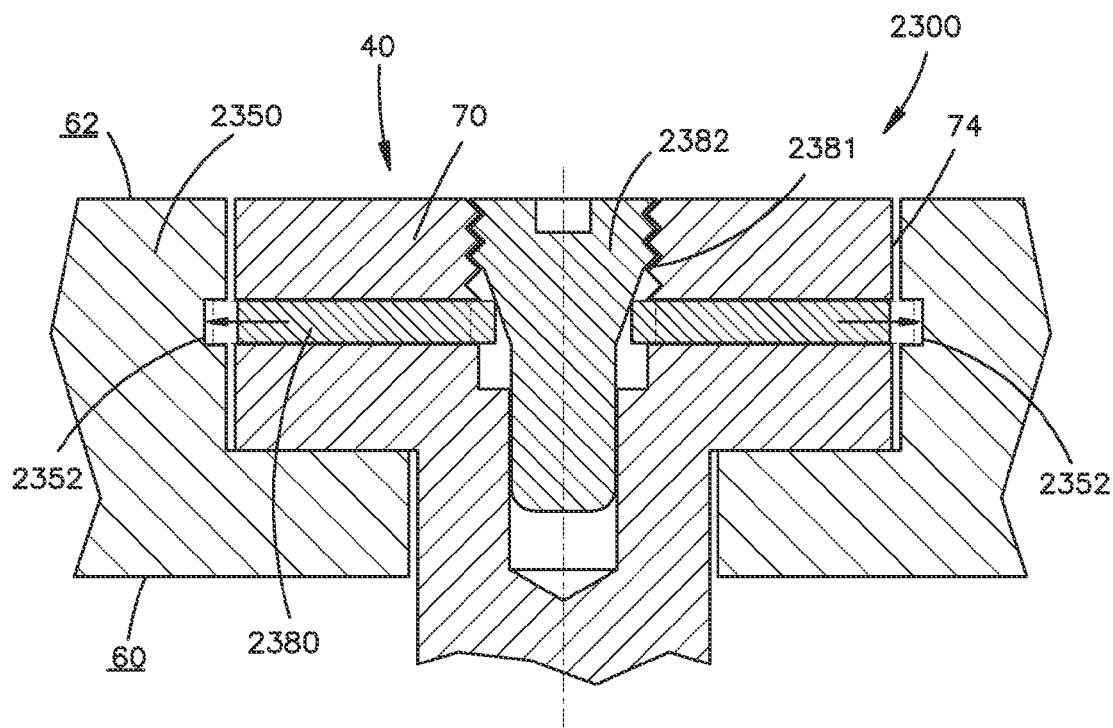
FIG. 26 illustrates a partial cross-sectional view of a plate portion, a bone fixation element and a retention mechanism of an implant according to a twenty-fourth preferred embodiment of the present invention.

Referring to FIG. 26, the intervertebral implant 2300 of a twenty-fourth preferred embodiment includes the interbody spacer portion (not shown), the plate portion 2350 and a plurality of bone fixation elements 70. In the twenty-fourth preferred embodiment, the bone fixation elements 70 include a spring member 2380 radially coupled to the head portion 74 thereof. In use, after the bone fixation element 70 has been inserted into the bone fixation hole 40 formed in the plate portion 2350 and into the patient's bone, a locking or set screw 2382 is inserted into a bore 2381 formed in the head portion 74 of the bone fixation element 70. The locking or set screw 2382 interacts with the spring member 2380 causing the spring member 2380 to radially expand into engagement with a groove 2352 formed in the bone fixation hole 40 to thereby secure the bone fixation element 70 to the plate portion 2350.

Figure 27:
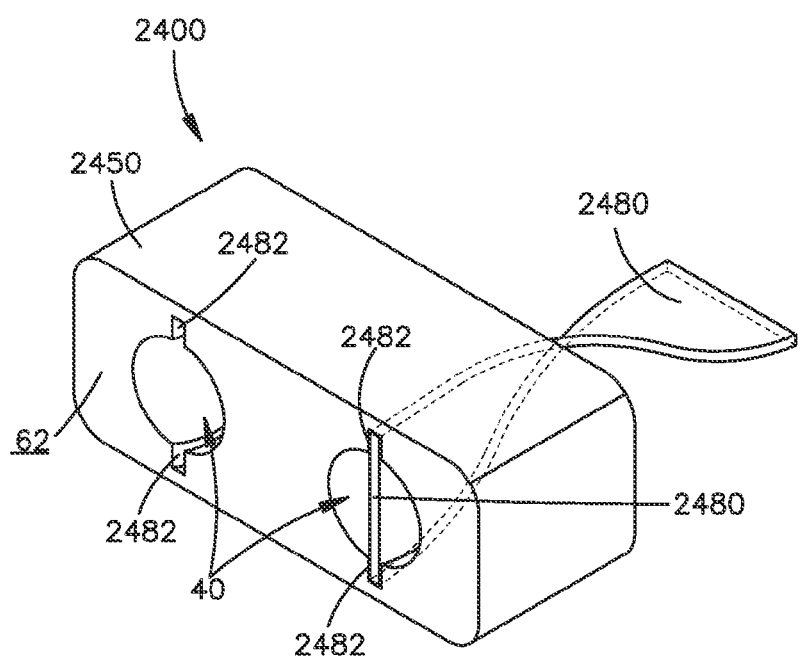
FIG. 27 illustrates a partial anterior perspective view of a plate portion, a bone fixation element and a retention mechanism of an implant according to a twenty-fifth preferred embodiment of the present invention.

Referring to FIG. 27, the intervertebral implant 2400 of a twenty-fifth preferred embodiment includes the interbody spacer portion (not shown), the plate portion 2450 and a plurality of bone fixation elements 70. In the twenty-fifth preferred embodiment, the bone fixation elements 70 are preferably in the form of a spiral blade 2480. The bone fixation holes 40 formed in the plate portion 2450 include one or more guide slots 2482 to enable the spiral blade 2480 to past therethrough. Due to its contorted shape, the spiral blade 2480 rotates as it is being inserted, which can be done by inserting the distal end of the spiral blade 2480 through the guide slots 2482 and impacting the proximal end of the spiral blade 2480 with a mallet or alternative instrument. The spiral blade 2480 rotates as it passes through the guide slots 2482 and cuts its way into bone. Once fully inserted, the guide slots 2482 and the helical arrangement of the spiral blade 2480 prevent the spiral blade 2480 from backing-out of the plate portion 2450.

Referring to FIG. 28, the intervertebral implant 2500 of a twenty-sixth preferred embodiment includes the interbody spacer portion 2520, the plate portion 2550 and a plurality of bone fixation elements 70. In the twenty-sixth preferred embodiment, the bone fixation elements 70 include an elastically deformable ring 2580. The elastically deformable ring 2580 is preferably disposed around the head portion 74 of the bone fixation element 70. In use, as the bone fixation element 70 is advanced into the bone fixation hole 40 formed in the plate portion 2550, the elastically deformable ring 2580 advances and is compressed until the ring 2580 aligns and expands within a groove 2582 formed in the bone fixation hole 40 to thereby secure the bone fixation element 70 to the plate portion 2550. Alternatively, the elastically deformable ring 2580 can be disposed within the groove 2582 formed in the bone fixation hole 40 of the plate portion 2550. The ring 2580 compresses as the bone fixation element 70 is advanced into the bone fixation hole 40 until the ring 2580 aligns and expands within a groove formed on the shaft, neck, or head portions of the bone fixation element 70.

Referring to FIG. 29, the intervertebral implant 2600 of a twenty-seventh preferred embodiment includes the interbody spacer portion 2620, the plate portion 2650 and a plurality of bone fixation elements 70. In the twenty-seventh preferred embodiment, the bone fixation elements 70 include a compressible head portion 74. The head portion 74 can be made compressible by counter boring and cutting radial slots 74a to create spring fingers 74b. The bone fixation holes 40 preferably include one or more inwardly extending projections 2680 so that during advancement of the bone fixation elements 70 into the bone fixation holes 40, the spring fingers 74b are compressed by the projections 2680. Once the head portion 74 is inserted past the projections 2680, the head portion 74 radially expands to limit the bone fixation element 70 from backing-out relative to the plate portion 2650.

Figure 30:
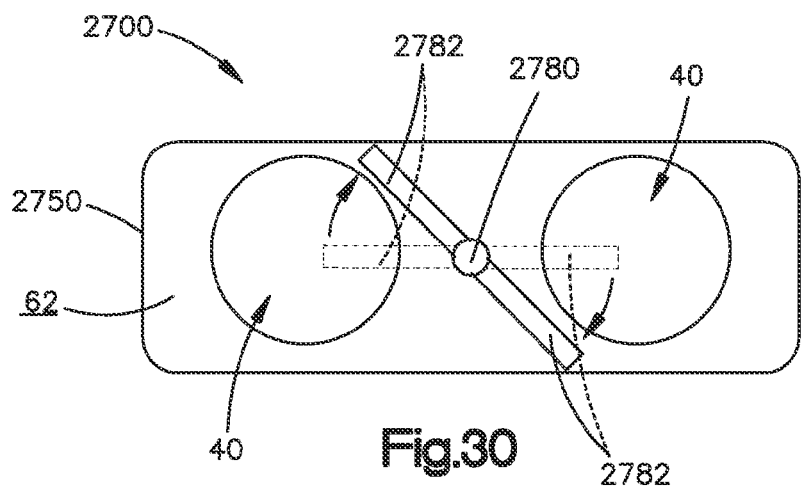
FIG. 30 illustrates an anterior elevational view of a plate portion and a retention mechanism of an implant according to a twenty-eight preferred embodiment of the present invention.

Referring to FIG. 30, the intervertebral implant 2700 of a twenty-eighth preferred embodiment includes the interbody spacer portion (not shown), the plate portion 2750, a plurality of bone fixation elements 70 and the retention mechanism. In the twenty-eighth preferred embodiment, the retention mechanism includes a rotational or torsional spring element 2780 rotatably coupled to the trailing surface 62 of the plate portion 2750. The rotational or torsional spring element 2780 includes one or more blocking pin portions 2782 attached thereto for at least partially covering the bone fixation holes 40. In use, as the bone fixation elements 70 are advanced into the bone fixation holes 40, the undersurface of the head portion 74 of the bone fixation 70 interacts with and pushes aside the blocking pins 2782 to allow the head portion 74 of the bone fixation element 70 to pass thereby. Once the head portion 74 is advanced past the blocking pin portions 2782, the rotational or torsional spring element 2780 returns the blocking pin portions 2782 to their original position at least partially covering the bone fixation holes 40. The rotational or torsional spring element 2780 is preferably configured to rotate out of the way to enable the bone fixation elements 70 to be inserted. The rotational or torsional spring element 2780 preferably snap back into place to at least partially cover the bone fixation holes 40 after the bone fixation elements 70 have been fully inserted. Alternatively, the retention mechanism may be in the form of a lead spring. Furthermore, linkages can be attached to the rotational or torsional spring element 2780 so that the linkages are pushed out of the way to enable the bone fixation element 70 to be inserted into the bone fixation holes 40 and return to at least partially cover the bone fixation holes 40. The rotational or torsional spring element 2780 can also be manually rotated to manipulate the linkages for locking and unlocking.

Figure 31A:
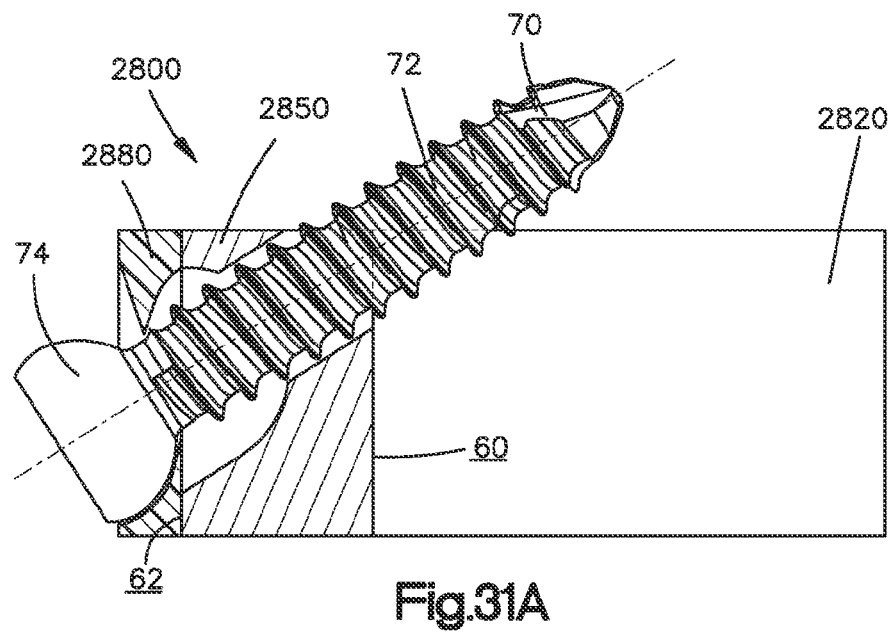
FIG. 31A illustrates a cross-sectional elevational view of a spacer portion, a plate portion, a bone fixation element and a retention mechanism of an implant according to a twenty-ninth preferred embodiment of the present invention.
Figure 31B:
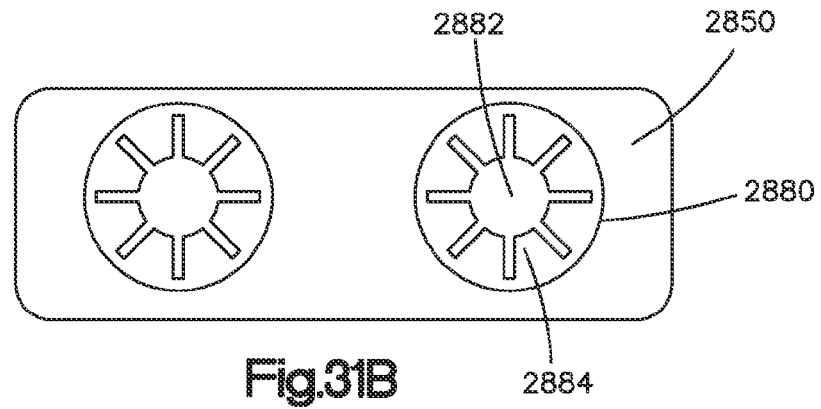
FIG. 31B illustrates a partial anterior elevational view the plate portion and the retention mechanism of the implant of FIG. 31A.

Referring to FIGS. 31A and 31B, the intervertebral implant 2800 of a twenty-ninth preferred embodiment includes the interbody spacer portion 2820, the plate portion 2850, a plurality of bone fixation elements 70 and the retention mechanism. In the twenty-ninth preferred embodiment, the retention mechanism includes a thin metallic web of material 2880. The metallic web of material 2880 having a hole 2882 and one or more slots or fingers 2884 radiating from the hole 2882. The metallic web of material 2880 being deformable so that in use, the metallic web of material 2880 deforms as the bone fixation element 70 is being advanced therethrough. The metallic web of material 2880 providing friction with the threaded shaft portion 72 of the bone fixation element 70 to prevent rotation and axial movement to thereby secure the bone fixation element 70 to the plate portion 2850. The metallic web of material 2880 can also be disposed interior to the spacer portion 2820 to interact with the threaded shaft portion 72 of the bone fixation element 70.

While the foregoing description and drawings represent the preferred embodiments of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

We claim:

1. A method of inserting an implant into an intervertebral disc space between first and second vertebrae using an intervertebral implant system that comprises an implant inserter instrument and the implant, the method comprising the steps of:
attaching the implant inserter instrument to the implant such that a contact region is defined, the contact region including all locations at which the implant inserter instrument contacts the implant;
inserting the implant into the intervertebral space along an insertion direction, such that: 1) a top surface of the implant contacts the first vertebra, and 2) a bottom surface of the implant contacts the second vertebra, the top surface opposite the bottom surface with respect to a second direction, the second direction being perpendicular to the insertion direction;
abutting a stop of the system with at least one of the first and second vertebrae, such that abutment of the stop with the at least one of the first and second vertebrae prevents further insertion of the implant into the intervertebral disc space in the insertion direction;
inserting a first bone fixation element through a first bone fixation hole of the implant and into the first vertebra, while the implant inserter instrument is attached to the implant;
inserting a second bone fixation element through a second bone fixation hole of the implant and into the second vertebra, while the implant inserter instrument is attached to the implant, the second bone fixation hole offset from the first bone fixation hole with respect to a third direction, the third direction being perpendicular to both the insertion direction and the second direction; and
detaching the implant inserter instrument from the implant;
wherein during the attaching step: 1) an entirety of the contact region is positioned between the first bone fixation hole and the second bone fixation hole with respect to the third direction, and 2) the contact region and the first bone fixation hole are each positioned with respect to the third direction such that a straight line drawn in the third direction intersects both the contact region and the first bone fixation hole, and
wherein the contact region defines a first width measured in the third direction such that no other width of the contact region measured in the third direction is greater than the first width, the implant defines a second width measured from the first bone fixation hole to the second bone fixation hole in the third direction such that no other width from the first bone fixation hole to the second bone fixation hole is less than the second width, and the first width is less than the second width.

2. The method of claim 1, wherein the step of inserting a first bone fixation element, and the step of inserting a second bone fixation element are both performed while the stop is abutting the at least one of the first and second vertebrae.

3. The method of claim 2, further comprising a step of repositioning at least one of the first and second vertebrae, such that a distance between the first and second vertebrae decreases.

4. The method of claim 1, wherein the attaching step further comprises rotating a handle portion of the implant inserter instrument to threadedly engage a threaded end of the implant inserter instrument with a threaded borehole of the implant.

5. The method of claim 4, further comprising, after the step of inserting the first bone fixation element, a step of blocking the first bone fixation element such that movement of the first bone fixation element in a direction opposite the insertion direction is prevented.

6. The method of claim 5, wherein the step of blocking the first bone fixation element comprises a step of coupling a retention mechanism to the implant such that the retention mechanism covers at least a portion of the first bone fixation element, thereby preventing back out of the first bone fixation element from the first bone fixation hole.

7. The method of claim 6, wherein the blocking step is performed after the detaching step, and the coupling step comprises threadedly engaging the retention mechanism with the threaded borehole of the implant.

8. The method of claim 1, further comprising after the step of inserting the first bone fixation element, a step of blocking the first bone fixation element such that movement of the first bone fixation element in a direction opposite the insertion direction is prevented.

9. The method of claim 8, wherein the step of blocking the first bone fixation element comprises a step of coupling a retention mechanism to the implant such that the retention mechanism covers at least a portion of the first bone fixation element, thereby preventing back out of the first bone fixation element from the first bone fixation hole.

10. The method of claim 8, further comprising, after the step of inserting the second bone fixation element, a step of blocking the second bone fixation element such that movement of the second bone fixation element in the direction opposite the insertion direction is prevented.

11. The method of claim 10, wherein the step of blocking the second bone fixation element comprises a step of coupling a retention mechanism to the implant such that the retention mechanism covers at least a portion of the second bone fixation element, thereby preventing back out of the second bone fixation element from the second bone fixation hole.

12. The method of claim 11, wherein the step of blocking the first bone fixation element comprises the step of coupling the retention mechanism to the implant such that the retention mechanism covers at least a portion of the first bone fixation element, thereby preventing back out of the first bone fixation element from the first bone fixation hole, and the step of blocking the second bone fixation element comprises the step of coupling the retention mechanism to the implant such that the retention mechanism covers at least a portion of the second bone fixation element, thereby preventing back out of the second bone fixation element from the second bone fixation hole.

13. The method of claim 1, wherein the implant inserter instrument comprises the stop, and the abutting step further comprises abutting the stop with one of the first and second vertebrae, such that the abutment of the stop with the one of the first and second vertebrae prevents further insertion of the implant in the insertion direction.

14. The method of claim 13, wherein the abutting step further comprises abutting the stop with the other of the first and second vertebrae, such that the abutment of the stop with the other of the first and second vertebrae prevents further insertion of the implant in the insertion direction.

15. The method of claim 1, wherein the stop is a first stop, the system comprises a second stop, and the abutting step further comprises abutting the first stop with one of the first and second vertebrae, and abutting the second stop with the other of the first and second vertebrae.

16. The method of claim 1, wherein the abutting step further comprises abutting the stop with a surface of the at least one of the first and second vertebrae that does not face the intervertebral space.

17. The method of claim 16, wherein the abutting step further comprises abutting the stop with at least one of an anterior aspect, a lateral aspect, and an anterior-lateral aspect of the at least one of the first and second vertebrae.

18. The method of claim 1, wherein the attaching step includes the steps of:
- abutting a first portion of the implant inserter instrument with a first recess defined by the implant; and
- abutting a second portion of the implant inserter instrument with a second recess defined by the implant.

19. The method of claim 1, wherein:
- during the step of inserting the implant, a trailing surface of the implant faces in a direction opposite the insertion direction, the trailing surface defines a first height measured in the second direction;
- after the attaching step and before the detaching step the implant inserter instrument defines a second height measured in the second direction, such that no other height of the implant inserter instrument is greater than the second height; and
- the second height is greater than the first height.

* * * * *